(12) United States Patent
Otterlei et al.

(10) Patent No.: US 8,871,724 B2
(45) Date of Patent: Oct. 28, 2014

(54) OLIGOPEPTIDIC COMPOUNDS AND USES THEREOF

(75) Inventors: Marit Otterlei, Trondheim (NO); Per Arne Aas, Trondheim (NO); Emadoldin Feyzi, Trondheim (NO)

(73) Assignee: Apim Therapeutics AS, Trondheim (NO)

( * ) Notice: Subject to any disclaimer, the term of this patent is extended or adjusted under 35 U.S.C. 154(b) by 603 days.

(21) Appl. No.: 12/918,797

(22) PCT Filed: Feb. 20, 2009

(86) PCT No.: PCT/GB2009/000489
§ 371 (c)(1),
(2), (4) Date: Oct. 15, 2010

(87) PCT Pub. No.: WO2009/104001
PCT Pub. Date: Aug. 27, 2009

(65) Prior Publication Data
US 2011/0020437 A1    Jan. 27, 2011

Related U.S. Application Data

(60) Provisional application No. 61/100,584, filed on Sep. 26, 2008.

(30) Foreign Application Priority Data

Feb. 22, 2008   (GB) .................................. 0803352.4

(51) Int. Cl.
| | | |
|---|---|---|
| A61K 38/16 | (2006.01) | |
| A61K 38/06 | (2006.01) | |
| A61M 1/16 | (2006.01) | |
| C07K 14/47 | (2006.01) | |
| G01N 33/68 | (2006.01) | |
| A61K 38/00 | (2006.01) | |

(52) U.S. Cl.
CPC ......... C07K 14/4738 (2013.01); *C07K 2319/10* (2013.01); *G01N 2800/56* (2013.01); G01N 33/6893 (2013.01); G01N 33/6872 (2013.01); *A61K 38/00* (2013.01)
USPC ......... 514/21.3; 530/324; 530/330; 514/21.8; 424/1.21; 424/9.321

(58) Field of Classification Search
None
See application file for complete search history.

(56) References Cited

U.S. PATENT DOCUMENTS

| | | | |
|---|---|---|---|
| 5,656,122 A | 8/1997 | Lenz et al. | |
| 5,888,762 A | 3/1999 | Joliot et al. | |
| 5,935,795 A | 8/1999 | Lin et al. | |
| 6,080,724 A | 6/2000 | Chassaing et al. | |
| 6,368,831 B1 | 4/2002 | Maurer et al. | |
| 6,472,507 B1* | 10/2002 | Fischer et al. | ................. 530/326 |
| 6,582,689 B1 | 6/2003 | Johnson | |
| 6,627,401 B2 | 9/2003 | Ralhan | |
| 6,645,501 B2 | 11/2003 | Dowdy | |
| 6,875,744 B2 | 4/2005 | Owen | |
| 6,902,931 B1 | 6/2005 | Toner et al. | |
| 6,992,169 B2 | 1/2006 | Fischer et al. | |
| 7,101,967 B2 | 9/2006 | Fischer et al. | |
| 7,153,931 B1 | 12/2006 | Fischer et al. | |
| 7,381,704 B2 | 6/2008 | Owen | |
| 2002/0137040 A1 | 9/2002 | Ralhan | |
| 2004/0029197 A1* | 2/2004 | Takimoto et al. | ............ 435/7.23 |
| 2007/0054401 A1 | 3/2007 | Prochiantz et al. | |
| 2007/0155668 A1 | 7/2007 | Prochiantz et al. | |
| 2007/0219139 A1 | 9/2007 | Sung-Ho et al. | |
| 2009/0286724 A1 | 11/2009 | Konishi | |

FOREIGN PATENT DOCUMENTS

| | | |
|---|---|---|
| EP | 0485578 B1 | 10/1996 |
| EP | 1004595 A2 | 5/2000 |
| JP | 2011-504933 A | 2/2011 |
| WO | WO 91/18981 A2 | 12/1991 |
| WO | WO 95/10297 A1 | 4/1995 |
| WO | WO 96/14334 A1 | 5/1996 |
| WO | WO 96/35715 A2 | 11/1996 |
| WO | WO 97/12912 A1 | 4/1997 |
| WO | WO 98/41873 A1 | 9/1998 |

(Continued)

OTHER PUBLICATIONS

Warbrick, Oncogene (2006) 25, 2850-2859.*

(Continued)

*Primary Examiner* — Satyanarayana R Gudibande
(74) *Attorney, Agent, or Firm* — Knobbe, Martens, Olson & Bear, LLP

(57) ABSTRACT

The present invention provides an oligopeptidic compound comprising a PCNA interacting motif, or a nucleic acid molecule comprising a sequence encoding said oligopeptidic compound, for use in therapy, wherein the PCNA interacting motif is $X_1X_2X_3X_3'X_1'$- (SEQ ID NO: 1), wherein $X_1$ and $X_1'$- are independently selected from the group of basic amino acids, $X_2$ is a lipophilic amino acid and $X_3$ and $X_3'$ are independently selected from the group of uncharged amino acids; and wherein the oligopeptidic compound is further characterized by at least one of the following: (i) the oligopeptidic compound comprises at least one signal sequence; (ii) the PCNA interacting motif is [K/R]-F-[L/I/V]-[L/I/V]-[K/R] (SEQ ID NO: 27). Particularly the therapy may be the treatment of a disorder or condition where it is desirable to inhibit the growth of cells, for example a hyperproliferative disorder, or a treatment which involves cytostatic therapy e.g., myeloablation. In certain aspects the compounds of the invention may be used as cytostatic agents in their own right. In other aspects of the invention oligopeptidic compounds comprising such a motif may be used in conjunction with cytostatic agents or with radiotherapy.

10 Claims, 8 Drawing Sheets

(56) References Cited

FOREIGN PATENT DOCUMENTS

| | | |
|---|---|---|
| WO | WO 00/00207 A1 | 1/2000 |
| WO | WO 00/01417 A1 | 1/2000 |
| WO | WO 00/29427 A2 | 5/2000 |
| WO | WO 00/75184 A1 | 12/2000 |
| WO | WO 01/21663 A1 | 3/2001 |
| WO | WO 01/40142 A2 | 6/2001 |
| WO | WO 01/40483 A1 | 6/2001 |
| WO | WO 01/55367 A1 | 8/2001 |
| WO | WO 01/64835 A2 | 9/2001 |
| WO | WO 02/079408 A2 | 10/2002 |
| WO | WO 02/100885 A2 | 12/2002 |
| WO | WO 03/051312 A2 | 6/2003 |
| WO | WO 03/074003 A2 | 9/2003 |
| WO | WO 2004/018503 * | 3/2004 |
| WO | WO 2004/031768 A2 | 4/2004 |
| WO | WO 2004/035732 A2 | 4/2004 |
| WO | WO 2004/069279 A1 | 8/2004 |
| WO | WO 2004/104030 A2 | 12/2004 |
| WO | WO 2005/087797 A1 | 9/2005 |
| WO | WO 2005/108421 A1 | 11/2005 |
| WO | WO 2007/019532 A2 | 2/2007 |
| WO | WO 2007/049695 A1 | 5/2007 |
| WO | WO 2007/098415 A2 | 8/2007 |
| WO | WO 2007/098719 A1 | 9/2007 |
| WO | WO 2008/000079 A1 | 1/2008 |
| WO | WO 2009/070642 A1 | 6/2009 |

OTHER PUBLICATIONS

Lu, 2002, JBC, 277, 24340-34345.*
Database Accession No. ABB03960, Jan. 8, 2002.
Fan, J. et al. 2004 "XRCCI co-localizes and physically interacts with PCNA" *Nucleic Acids Research* 32(7):2193-2201.
Kiyonari, S. et al. 2006 "Identification of a Novel Binding Motif in *Pyrococcus furiosus* DNA Ligase for the Functional Interaction with Proliferating Cell Nuclear Antigen" *The Journal of Biological Chemistry* 281(38):28023-28032.
Krag, D. N. et al. 2002 "Phage-Displayed Random Peptide Libraries in Mice: Toxicity After Serial Panning" *Cancer Chemotheraphy and Pharmacology* 50(4):325-332.
Lu, X. et al. 2002 "Direct Interaction of Proliferating Cell Nuclear Antigen with the Small Subunit of DNA Polymerase delta" *The Journal of Biological Chemistry* 277(27):24340-24345.
Pohler, J.R.G. et al. 2005 "An in vivo analysis of the localisation and interactions of human p66 DNA polymerase [delta] subunit" *BMC Molecular Biology* 6(1):17.
Warbrick, E. 2006 "A functional analysis of PCNA-binding peptides derived from protein sequence, interaction screening and rational design" *Onogene* 25 2850-2859.
Aas, P. A. et al. 2003 "Human and bacterial oxidative demethylases repair alkylation damage in both RNA and DNA" *Nature* 421: 859-863.
Bolton, S.J. et al 2000 "Cellular uptake and spread of the cell-permeable peptide penetratin in adult rat brain" *Eur J Neurosci* 12: 2847-55.
De Coupade, C. et al. 2005 "Novel human-derived cell-penetrating peptides for specific subcellular delivery of therapeutic biomolecules" *Biochem J* 390: 407-418.
Dingwall, C. et al. 1988 "The nucleoplasmin nuclear location sequence is larger and more complex than that of SV-40 large T antigen" *J Cell Biol* 107:841-849.
Drabløs, F. et al. 2004 "Alkylation damage in DNA and RNA—repair mechanisms and medical significance" *DNA Repair* 2; 1389-1407.
Duncan, T. et al. 2002 "Reversal of DNA alkylation damage by two human dioxygenases" *Proc Nati Acad Sci U S A* 24: 16660-5.
Elliott, G. et al.1997 "Intercellular trafficking and protein delivery by a herpesvirus structural protein" *Cell* 88:223-33.
Elmquist, A. et al. 2003 "In vitro uptake and stability study of pVEC and its all-D analog" *Biol Chem* 384:387-93.
Gilljam, M. K. 2006 Abstract title: "Identification of a novel PCNA interacting motif;" Presentation title: "hABH2 interactions with PCNA through a novel PCNA binding motif;" Conference title: Erling Seeberg Symposium on DNA repair; Conference location: Bodø and Henningsvær, Lofoten, Norway; Conference dates: May 28-Jun. 2, 2006.
Gilljam, M. K. 2007 Abstract title: "hABH2 interactions with PCNA through a novel PCNA binding motif;" Presentation title: "hABH2 interactions with PCNA through a novel PCNA binding motif;" Conference title: Young scientist: DNA damage response and repair mechanisms; Conference location: Ghent, Belgium; Conference date: May 14, 2007.
Gilljam, M. K. 2007 Abstract title: "Identification of a novel PCNA interacting motif;" Presentation title: Use of confocal microscopy to identify protein interactions: "Identification of a novel PCNA interacting motif in the N-terminus of hABH2;" Conference title: EMBO: EMBO practical course; Imaging in 3-D and the F-techniques: FRET, FCS, FLIM and FRAP; Conference location: Biopolis, Singapore; Conference date: Jun. 17, 2007.
Guinez, C. et al. 2005 "O-GlcNAc glycosylation: a signal for the nuclear transport of cytosolic proteins?" *Int J Biochem Cell Biol* 37:765-74.
Haracska, L. et al. 2005 "A single domain in human DNA polymerase iota mediates interaction with PCNA: implications for translesion DNA synthesis" *Mol Cell Biol* 25:1183-90.
Hoelz, D.J. et al. 2006 "The discovery of labile methyl esters on proliferating cell nuclear antigen by MS/MS" *Proteomics* 6:4808-16.
Holm, T. et al. 2005 "Uptake of cell-penetrating peptides in yeasts" *FEBS Lett.* 579:5217-22.
Ishii, T. et al. 2001 "Mechanism of cell transfection with plasmid/chitosan complexes" *Biochim Biophys Acta* 1514:51-64.
Jacquemont, C. et al. 2007 "The Fanconi anemia pathway and ubiquitin" *BMC Biochem* 22; Suppl 1:S10.
Järver, P. et al. 2006 "Cell-penetrating peptides—a brief introduction" *Biochim Biophys Acta* 1758:260-3.
Joliot, A. et al. 1991 "Antennapedia homeobox peptide regulates neural morphogenesis" *Proc Natl Acad Sci U S A* 88:1864-8.
Kaina, B. et al. 2007 "MGMT: key node in the battle against genotoxicity, carcinogenicity and apoptosis induced by alkylating agents" *DNA Repair* 6:1079-99.
Kamei, N. et al. 2008 "Usefulness of cell-penetrating peptides to improve intestinal insulin absorption" *J Control Release* 132:21-5.
Kim, J.H. et al. 2008 "Antitumor efficacy of cisplatin-loaded glycol chitosan nanoparticles in tumor-bearing mice" *J Control Release* 127:41-9.
Kondo, E. et al. 2004 "Highly efficient delivery of p16 antitumor peptide into aggressive leukemia/lymphoma cells using a novel transporter system" *Mol Cancer Ther* 3:1623-30.
Krauss, U. 2004 "In vitro gene delivery by a novel human calcitonin (hCT)-derived carrier peptide" *Bioorg Med Chem Lett* 14:51-4.
Lange, A. et al. 2007 "Classical nuclear localization signals: definition, function, and interaction with importin alpha" *J Biol Chem* 282:5101-5.
Leslie, D. M. et al. 2006 "Studying nuclear protein import in yeast" *Methods* 39:291-308.
Lou, Z. et al. 2005 "BRCA1 participates in DNA decatenation" *Nat Struct Mol Bio.* 12:589-93.
Lusk, C. P. et al. 2007 "Highway to the inner nuclear membrane: rules for the road" *Nat Rev Mol Cell Biol* 8:414-20.
Mäe, M. et al. 2006 "Cell-penetrating peptides as vectors for peptide, protein and oligonucleotide delivery" *Curr Opin Pharmacol* 6:509-14.
Maga, G. et al. 2003 "Proliferating cell nuclear antigen (PCNA): a dancer with many partners" *J Cell Sci* 116:3051-60.
Makkerh, J.P. et al. 1996 "Comparative mutagenesis of nuclear localization signals reveals the importance of neutral and acidic amino acids" *Curr Biol* 6:1025-7.
Malkas, L. H. et al. 2006 "A cancer-associated PCNA expressed in breast cancer has implications as a potential biomarker" *Proc Nati Acad Sci U S A* 103:19472-7.
Mo, Y.Y. et al. 1999 "Association of human DNA topoisomerase IIα with mitotic chromosomes in mammalian cells is independent of its catalytic activity" *Exp Cell Res.* 252:50-62.
Moldovan, G.-L. 2007 "PCNA, the maestro of the replication fork" *Cell* 129:665-79.

(56) References Cited

OTHER PUBLICATIONS

Morris, M.C. 2001 "A peptide carrier for the delivery of biologically active proteins into mammalian cells" *Nat Biotechnol* 19:1173-6.

Mosmann, T. 1983 "Rapid colorimetric assay for cellular growth and survival: application to proliferation and cytotoxicity assays" *J Immunol. Methods* 65:55-63.

Niimi, A. et al. 2001 "Co-localization of chicken DNA topoisomerase IIα, but not β, with sites of DNA replication and possible involvement of a C-terminal region of α through its binding to PCNA" *Chromosoma* 110:102-14.

Oehlke, J 1998 "Cellular uptake of an α-helical amphipathic model peptide with the potential to deliver polar compounds into the cell interior non-endocytically" *Biochim Biophys Acta* 1414:127-39.

Opresko, P. L. 2004 "The Werner syndrome helicase and exonuclease cooperate to resolve telomeric D loops in a manner regulated by TRF1 and TRF2" *Mol Cell* 14:763-74.

Pooga, M et al. 1998 "Cell penetration by transportan" *FASEB J* 12:67-77.

Potocky, T. B. 2003 "Cytoplasmic and nuclear delivery of a TAT-derived peptide and a β-peptide after endocytic uptake into HeLa cells" *J Biol Chem* 278:50188-94.

Potts, P. R. et al. 2006 "Human SMC5/6 complex promotes sister chromatid homologous recombination by recruiting the SMC1/3 cohesin complex to double-strand breaks" *EMBO J.* 25:3377-88.

Pujals, S. et al 2008 "Proline-rich, amphipathic cell-penetrating peptides" *Adv Drug Deliv Rev* 60:473-84.

Rademakers, S. et al 2003 "Xeroderma pigmentosum group A protein loads as a separate factor onto DNA lesions" *Mol Cell Biol* 23:5755-67.

Ringvoll, J. et al. 2006 "Repair deficient mice reveal mABH2 as the primary oxidative demethylase for repairing 1meA and 3meC lesions in DNA" *Embo J* 25:2189-98.

Rothbard, J. B. 2000 "Conjugation of arginine oligomers to cyclosporin A facilitates topical delivery and inhibition of inflammation" *Nat Med* 6:1253-7.

Rousselle, C et al. 2000 "New advances in the transport of doxorubicin through the blood-brain barrier by a peptide vector-mediated strategy" *Mol Pharmacol* 57:679-86.

Roy, A. L. 1993 "An alternative pathway for transcription initiation involving TFII-I" *Nature* 365:355-9.

Simbulan-Rosenthal, C.M. et al. 1999 "Involvement of PARP and poly(ADP-ribosyl)ation in the early stages of apoptosis and DNA replication" *Mol Cell Biochem* 193:137-48.

Snyder, E.L. 2004 "Treatment of terminal peritoneal carcinomatosis by a transducible p53-activating peptide" *PLoS Biol* 2:E36.

Soomets, U. et al. 2000 "Deletion analogues of transportan" *Biochem Biophys Acta* 1467:165-76.

Venturi, A. et al. 2008 "Human hepatocellular carcinoma expresses specific PCNA isoforms: an in vivo and in vitro evaluation" *Lab Invest* 88:995-1007.

Vivés, E. 1997 "A truncated HIV-1 Tat protein basic domain rapidly translocates through the plasma membrane and accumulates in the cell nucleus" *J Biol Chem* 272:16010-7.

Wagstaff, K. M. et al. 2006 "Protein transduction: cell penetrating peptides and their therapeutic applications" *Curr Med Chem* 13:1371-87.

Warbrick, E. 2000 "The puzzle of PCNA's many partners" *Bioessays* 22:997-1006.

Wyman, T. B. et al. 1997 "Design, synthesis, and characterization of a cationic peptide that binds to nucleic acids and permeabilizes bilayers" *Biochemistry* 36:3008-17.

Xu, H. et al. 2001 "A novel PCNA-binding motif identified by the panning of a random peptide display library" *Biochemistry* 40:4512-20.

Zorko, M. & Langel, U. 2005 "Cell-penetrating peptides: mechanism and kinetics of cargo delivery" *Adv Drug Deliv Rev* 57:529-45.

Definition of "Diamino" 1994 in McGraw-Hill Dictionary of Scientific and Technical Terms, Sybil P. Parker, Editor in Chief, New York.

\* cited by examiner

Figure 4

AlkB homolog 2

APIM

| | |
|---|---|
| Homo sapiens/1-10 | M D R F L V K G A Q |
| Bos taurus/1-10 | M D R F L V K G A V |
| Rattus norvegicus/1-10 | M D R F L V R P D R |
| Mus musculus/1-10 | M D K F L V R P D L |
| Gallus gallus/1-10 | M D R F V V K R S A |
| Strongy. purp./1-10 | M D K F I I K R K K |

Figure 5

TFIIS elongation factor like protein TFIIS-L

APIM

| | | |
|---|---|---|
| Homo sapiens/1-10 | M D K F V I R T P R |
| Mus musculus/1-10 | M D K F V I R T P R |
| Gallus gallus/1-10 | M E R F V V R R A R |
| Xenopus tropicalis/1-10 | M D R F V I R K Q K |

General transcription factor II TFII-I, isoform γ

| | |
|---|---|
| Homo sapiens/428-437 | R I R F V I K K H E |
| Mus musculus/428-437 | R I R F V I K K H E |
| Xenopus laevis/369-378 | R I R F V I K K P E |

| | |
|---|---|
| Homo sapiens/533-542 | R I K F V I K R P E |
| Mus musculus/533-542 | R I K F V I K R P E |
| Xenopus laevis/473-482 | R I K F V I K K P E |

| | |
|---|---|
| Homo sapiens/638-647 | K I K F V V K K P E |
| Mus musculus/638-647 | K I K F V V K K P E |
| Xenopus laevis/577-586 | K I K F I V K K P H |

| | |
|---|---|
| Homo sapiens/800-809 | K I K F I I K K P E |
| Mus musculus/800-809 | K I K F I I K K P E |
| Xenopus laevis/732-741 | K I K F V I K K P E |

DNA topoisomerase II alpha Topo II α

| | |
|---|---|
| Homo sapiens/965-974 | T V K F V V K M T E |
| Mus musculus/964-973 | T V K F V I K M T E |
| Gallus gallus/966-975 | T V K F V V K M S E |
| Xenopus laevis/963-972 | T V R F L V K M T E |

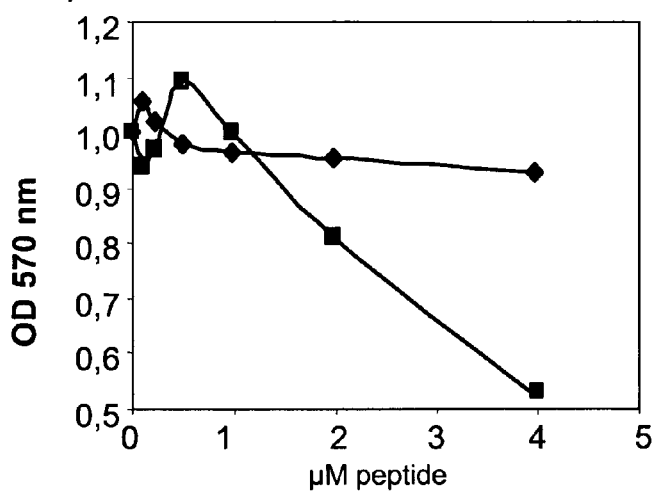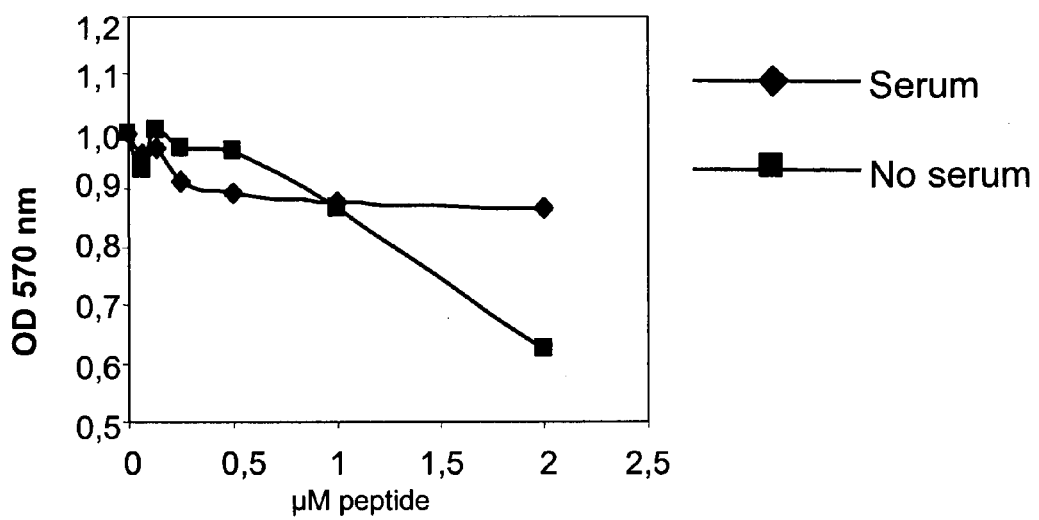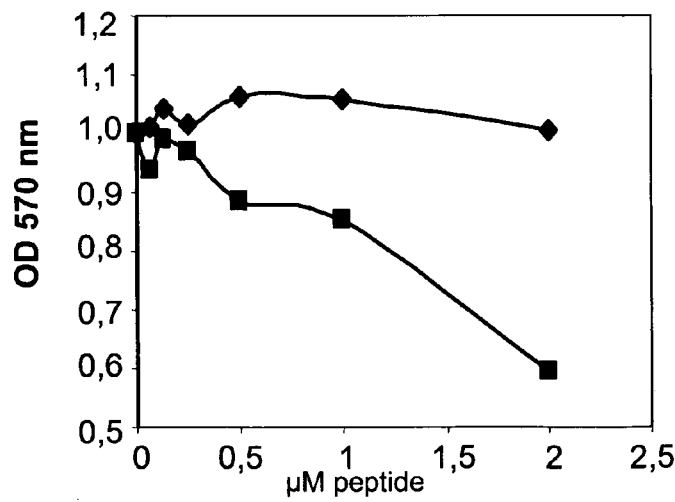
Figure 6 ns*US 8,871,724 B2*

SEQUENCE LISTING

<160> NUMBER OF SEQ ID NOS: 134

<210> SEQ ID NO 1
<211> LENGTH: 5
<212> TYPE: PRT
<213> ORGANISM: Artificial sequence
<220> FEATURE:
<223> OTHER INFORMATION: Consensus APIM
<220> FEATURE:
<221> NAME/KEY: VARIANT
<222> LOCATION: (1)..(1)
<223> OTHER INFORMATION: X may be any genetic or non-genetic basic amino acid and it may be modified

```
<220> FEATURE:
<221> NAME/KEY: VARIANT
<222> LOCATION: (2)..(2)
<223> OTHER INFORMATION: X may be any genetic or non-genetic lipophilic
      amino acid and it may be modified
<220> FEATURE:
<221> NAME/KEY: VARIANT
<222> LOCATION: (3)..(4)
<223> OTHER INFORMATION: X may be any genetic or non-genetic uncharged
      amino acid and it may be modified
<220> FEATURE:
<221> NAME/KEY: VARIANT
<222> LOCATION: (5)..(5)
<223> OTHER INFORMATION: X may be any genetic or non-genetic basic amino
      acid and it may be modified

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial sequence
<220> FEATURE:
<223> OTHER INFORMATION: PCNA Binding motif (APIM)

<400> SEQUENCE: 2

Arg Phe Leu Val Lys
1               5

<210> SEQ ID NO 3
<211> LENGTH: 5
<212> TYPE: PRT
<213> ORGANISM: Artificial sequence
<220> FEATURE:
<223> OTHER INFORMATION: APIM variant

<400> SEQUENCE: 3

Lys Phe Leu Leu Arg
1               5

<210> SEQ ID NO 4
<211> LENGTH: 5
<212> TYPE: PRT
<213> ORGANISM: Artificial sequence
<220> FEATURE:
<223> OTHER INFORMATION: APIM variant

<400> SEQUENCE: 4

Lys Tyr Leu Leu Arg
1               5

<210> SEQ ID NO 5
<211> LENGTH: 5
<212> TYPE: PRT
<213> ORGANISM: Artificial sequence
<220> FEATURE:
<223> OTHER INFORMATION: APIM variant

<400> SEQUENCE: 5

Lys Trp Leu Leu Arg
1               5

<210> SEQ ID NO 6
<211> LENGTH: 5
<212> TYPE: PRT
<213> ORGANISM: Artificial sequence
<220> FEATURE:
```

```
<223> OTHER INFORMATION: APIM variant

<400> SEQUENCE: 6

Lys Tyr Ile Leu Arg
1               5

<210> SEQ ID NO 7
<211> LENGTH: 5
<212> TYPE: PRT
<213> ORGANISM: Artificial sequence
<220> FEATURE:
<223> OTHER INFORMATION: APIM variant

<400> SEQUENCE: 7

Lys Tyr Val Leu Arg
1               5

<210> SEQ ID NO 8
<211> LENGTH: 5
<212> TYPE: PRT
<213> ORGANISM: Artificial sequence
<220> FEATURE:
<223> OTHER INFORMATION: APIM variant

<400> SEQUENCE: 8

Arg Phe Leu Leu Arg
1               5

<210> SEQ ID NO 9
<211> LENGTH: 5
<212> TYPE: PRT
<213> ORGANISM: Artificial sequence
<220> FEATURE:
<223> OTHER INFORMATION: APIM variant

<400> SEQUENCE: 9

Arg Tyr Leu Leu Arg
1               5

<210> SEQ ID NO 10
<211> LENGTH: 5
<212> TYPE: PRT
<213> ORGANISM: Artificial sequence
<220> FEATURE:
<223> OTHER INFORMATION: APIM variant

<400> SEQUENCE: 10

Arg Trp Leu Leu Arg
1               5

<210> SEQ ID NO 11
<211> LENGTH: 5
<212> TYPE: PRT
<213> ORGANISM: Artificial sequence
<220> FEATURE:
<223> OTHER INFORMATION: APIM variant

<400> SEQUENCE: 11

Arg Tyr Ile Leu Arg
1               5

<210> SEQ ID NO 12
<211> LENGTH: 5
<212> TYPE: PRT
<213> ORGANISM: Artificial sequence
<220> FEATURE:
<223> OTHER INFORMATION: APIM variant
```

```
<400> SEQUENCE: 12

Arg Tyr Val Leu Arg
1               5

<210> SEQ ID NO 13
<211> LENGTH: 5
<212> TYPE: PRT
<213> ORGANISM: Artificial sequence
<220> FEATURE:
<223> OTHER INFORMATION: APIM variant

<400> SEQUENCE: 13

Arg Phe Leu Ile Arg
1               5

<210> SEQ ID NO 14
<211> LENGTH: 5
<212> TYPE: PRT
<213> ORGANISM: Artificial sequence
<220> FEATURE:
<223> OTHER INFORMATION: APIM variant

<400> SEQUENCE: 14

Arg Tyr Leu Val Arg
1               5

<210> SEQ ID NO 15
<211> LENGTH: 5
<212> TYPE: PRT
<213> ORGANISM: Artificial sequence
<220> FEATURE:
<223> OTHER INFORMATION: APIM variant

<400> SEQUENCE: 15

Arg Trp Leu Met Arg
1               5

<210> SEQ ID NO 16
<211> LENGTH: 5
<212> TYPE: PRT
<213> ORGANISM: Artificial sequence
<220> FEATURE:
<223> OTHER INFORMATION: APIM variant

<400> SEQUENCE: 16

Arg Tyr Val Leu Arg
1               5

<210> SEQ ID NO 17
<211> LENGTH: 5
<212> TYPE: PRT
<213> ORGANISM: Artificial sequence
<220> FEATURE:
<223> OTHER INFORMATION: APIM variant

<400> SEQUENCE: 17

Arg Tyr Val Ile Arg
1               5

<210> SEQ ID NO 18
<211> LENGTH: 5
<212> TYPE: PRT
<213> ORGANISM: Artificial sequence
<220> FEATURE:
<223> OTHER INFORMATION: APIM variant
```

```
<400> SEQUENCE: 18

Arg Trp Leu Val Lys
1               5

<210> SEQ ID NO 19
<211> LENGTH: 5
<212> TYPE: PRT
<213> ORGANISM: Artificial sequence
<220> FEATURE:
<223> OTHER INFORMATION: APIM variant

<400> SEQUENCE: 19

Arg Tyr Leu Val Lys
1               5

<210> SEQ ID NO 20
<211> LENGTH: 5
<212> TYPE: PRT
<213> ORGANISM: Artificial sequence
<220> FEATURE:
<223> OTHER INFORMATION: APIM variant

<400> SEQUENCE: 20

Arg Trp Leu Ile Lys
1               5

<210> SEQ ID NO 21
<211> LENGTH: 5
<212> TYPE: PRT
<213> ORGANISM: Artificial sequence
<220> FEATURE:
<223> OTHER INFORMATION: APIM variant

<400> SEQUENCE: 21

Arg Trp Ile Val Lys
1               5

<210> SEQ ID NO 22
<211> LENGTH: 5
<212> TYPE: PRT
<213> ORGANISM: Artificial sequence
<220> FEATURE:
<223> OTHER INFORMATION: APIM variant

<400> SEQUENCE: 22

Arg Trp Val Val Lys
1               5

<210> SEQ ID NO 23
<211> LENGTH: 5
<212> TYPE: PRT
<213> ORGANISM: Artificial sequence
<220> FEATURE:
<223> OTHER INFORMATION: APIM variant

<400> SEQUENCE: 23

Arg Trp Ala Val Lys
1               5

<210> SEQ ID NO 24
<211> LENGTH: 5
<212> TYPE: PRT
<213> ORGANISM: Artificial sequence
<220> FEATURE:
<223> OTHER INFORMATION: APIM variant

<400> SEQUENCE: 24
```

```
Arg Tyr Val Val Lys
1               5

<210> SEQ ID NO 25
<211> LENGTH: 5
<212> TYPE: PRT
<213> ORGANISM: Artificial sequence
<220> FEATURE:
<223> OTHER INFORMATION: APIM variant

<400> SEQUENCE: 25

Arg Tyr Leu Ile Lys
1               5

<210> SEQ ID NO 26
<211> LENGTH: 5
<212> TYPE: PRT
<213> ORGANISM: Artificial sequence
<220> FEATURE:
<223> OTHER INFORMATION: APIM variant

<400> SEQUENCE: 26

Arg Tyr Leu Met Lys
1               5

<210> SEQ ID NO 27
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (1)..(1)
<223> OTHER INFORMATION: /REPLACE="Lys" or "Arg"
<220> FEATURE:
<221> NAME/KEY: VARIANT
<222> LOCATION: (3)..(4)
<223> OTHER INFORMATION: /REPLACE="Leu" or "Ile" or "Val"
<220> FEATURE:
<221> NAME/KEY: VARIANT
<222> LOCATION: (5)..(5)
<223> OTHER INFORMATION: /REPLACE="Lys" or "Arg"

<400> SEQUENCE: 27

Xaa Phe Xaa Xaa Xaa
1               5

<210> SEQ ID NO 28
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala" or
      "Met"
<220> FEATURE:
<221> NAME/KEY: variant
<222> LOCATION: (5)..(5)
<223> OTHER INFORMATION: /REPLACE= "Lys" or "Arg"
```

-continued

```
<400> SEQUENCE: 28

Xaa Xaa Xaa Xaa Xaa
1               5

<210> SEQ ID NO 29
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala" or
      "Met"
<220> FEATURE:
<221> NAME/KEY: variant
<222> LOCATION: (5)..(5)
<223> OTHER INFORMATION: /REPLACE= "Lys" or "Arg"

<400> SEQUENCE: 29

Xaa Xaa Xaa Xaa Xaa
1               5

<210> SEQ ID NO 30
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala"
<220> FEATURE:
<221> NAME/KEY: variant
<222> LOCATION: (5)..(5)
<223> OTHER INFORMATION: /REPLACE= "Lys" or "Arg"

<400> SEQUENCE: 30

Xaa Xaa Xaa Xaa Xaa
1               5

<210> SEQ ID NO 31
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
```

```
-continued

<223> OTHER INFORMATION: /REPLACE= "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala"
<220> FEATURE:
<221> NAME/KEY: variant
<222> LOCATION: (5)..(5)
<223> OTHER INFORMATION: /REPLACE= "Lys" or "Arg"

<400> SEQUENCE: 31

Xaa Xaa Xaa Xaa Xaa
1               5

<210> SEQ ID NO 32
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala" or
      "Met"
<220> FEATURE:
<221> NAME/KEY: variant
<222> LOCATION: (5)..(5)
<223> OTHER INFORMATION: /REPLACE= "Lys" or "Arg"

<400> SEQUENCE: 32

Xaa Xaa Xaa Xaa Xaa
1               5

<210> SEQ ID NO 33
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp"
<220> FEATURE:
<221> NAME/KEY: variant
<222> LOCATION: (3)..(4)
<223> OTHER INFORMATION: /REPLACE= "Leu" or "Ile" or "Val" or "Ala"
<220> FEATURE:
<221> NAME/KEY: variant
<222> LOCATION: (5)..(5)
<223> OTHER INFORMATION: /REPLACE= "Lys" or "Arg"

<400> SEQUENCE: 33

Xaa Xaa Xaa Xaa Xaa
1               5

<210> SEQ ID NO 34
<211> LENGTH: 5
<212> TYPE: PRT
<213> ORGANISM: Artificial sequence
```

```
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp"
<220> FEATURE:
<221> NAME/KEY: variant
<222> LOCATION: (3)..(4)
<223> OTHER INFORMATION: /REPLACE= "Leu" or "Ile" or "Val"
<220> FEATURE:
<221> NAME/KEY: variant
<222> LOCATION: (5)..(5)
<223> OTHER INFORMATION: /REPLACE= "Lys" or "Arg"

<400> SEQUENCE: 34

Xaa Xaa Xaa Xaa Xaa
1               5

<210> SEQ ID NO 35
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val"
<220> FEATURE:
<221> NAME/KEY: variant
<222> LOCATION: (5)..(5)
<223> OTHER INFORMATION: /REPLACE= "Lys" or "Arg"

<400> SEQUENCE: 35

Xaa Xaa Xaa Xaa Xaa
1               5

<210> SEQ ID NO 36
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Tyr" or "Trp"
<220> FEATURE:
<221> NAME/KEY: variant
<222> LOCATION: (3)..(4)
<223> OTHER INFORMATION: /REPLACE= "Leu" or "Ile" or "Val"
<220> FEATURE:
<221> NAME/KEY: variant
<222> LOCATION: (5)..(5)
<223> OTHER INFORMATION: /REPLACE= "Lys" or "Arg"

<400> SEQUENCE: 36
```

```
Xaa Xaa Xaa Xaa Xaa
1               5

<210> SEQ ID NO 37
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (3)..(4)
<223> OTHER INFORMATION: /REPLACE= "Leu" or "Ile" or "Val"
<220> FEATURE:
<221> NAME/KEY: variant
<222> LOCATION: (5)..(5)
<223> OTHER INFORMATION: /REPLACE= "Lys" or "Arg"

<400> SEQUENCE: 37

Xaa Phe Xaa Xaa Xaa
1               5

<210> SEQ ID NO 38
<211> LENGTH: 16
<212> TYPE: PRT
<213> ORGANISM: Artificial sequence
<220> FEATURE:
<223> OTHER INFORMATION: Penetratin

<400> SEQUENCE: 38

Arg Gln Ile Lys Ile Trp Phe Gln Asn Arg Arg Met Lys Trp Lys Lys
1               5                   10                  15

<210> SEQ ID NO 39
<211> LENGTH: 7
<212> TYPE: PRT
<213> ORGANISM: Artificial sequence
<220> FEATURE:
<223> OTHER INFORMATION: Penetratin derivative

<400> SEQUENCE: 39

Arg Arg Met Lys Trp Lys Lys
1               5

<210> SEQ ID NO 40
<211> LENGTH: 8
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (1)..(1)
<223> OTHER INFORMATION: Nle

<400> SEQUENCE: 40

Xaa Arg Arg Met Lys Trp Lys Lys
1               5

<210> SEQ ID NO 41
<211> LENGTH: 9
<212> TYPE: PRT
<213> ORGANISM: Artificial sequence
<220> FEATURE:
<223> OTHER INFORMATION: Penetratin derivative
<220> FEATURE:
```

```
<221> NAME/KEY: MOD_RES
<222> LOCATION: (2)..(2)
<223> OTHER INFORMATION: Nle

<400> SEQUENCE: 41

Gln Xaa Arg Arg Met Lys Trp Lys Lys
1               5

<210> SEQ ID NO 42
<211> LENGTH: 10
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Nle

<400> SEQUENCE: 42

Phe Gln Xaa Arg Arg Met Lys Trp Lys Lys
1               5                   10

<210> SEQ ID NO 43
<211> LENGTH: 7
<212> TYPE: PRT
<213> ORGANISM: Artificial sequence
<220> FEATURE:
<223> OTHER INFORMATION: Penetratin derivative

<400> SEQUENCE: 43

Arg Arg Glu Lys Trp Lys Lys
1               5

<210> SEQ ID NO 44
<211> LENGTH: 7
<212> TYPE: PRT
<213> ORGANISM: Artificial sequence
<220> FEATURE:
<223> OTHER INFORMATION: Penetratin derivative

<400> SEQUENCE: 44

Arg Arg Gln Lys Trp Lys Lys
1               5

<210> SEQ ID NO 45
<211> LENGTH: 7
<212> TYPE: PRT
<213> ORGANISM: Artificial sequence
<220> FEATURE:
<223> OTHER INFORMATION: Penetratin derivative

<400> SEQUENCE: 45

Lys Arg Met Lys Trp Lys Lys
1               5

<210> SEQ ID NO 46
<211> LENGTH: 7
<212> TYPE: PRT
<213> ORGANISM: Artificial sequence
<220> FEATURE:
<223> OTHER INFORMATION: Penetratin derivative

<400> SEQUENCE: 46

Arg Lys Met Lys Trp Lys Lys
1               5
```

```
<210> SEQ ID NO 47
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Orn

<400> SEQUENCE: 47

Arg Arg Xaa Lys Trp Lys Lys
1               5

<210> SEQ ID NO 48
<211> LENGTH: 7
<212> TYPE: PRT
<213> ORGANISM: Artificial sequence
<220> FEATURE:
<223> OTHER INFORMATION: Penetratin derivative

<400> SEQUENCE: 48

Arg Arg Met Lys Gln Lys Lys
1               5

<210> SEQ ID NO 49
<211> LENGTH: 7
<212> TYPE: PRT
<213> ORGANISM: Artificial sequence
<220> FEATURE:
<223> OTHER INFORMATION: Penetratin derivative

<400> SEQUENCE: 49

Arg Arg Met Lys Trp Phe Lys
1               5

<210> SEQ ID NO 50
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Orn

<400> SEQUENCE: 50

Arg Xaa Arg Lys Trp Lys Lys
1               5

<210> SEQ ID NO 51
<211> LENGTH: 7
<212> TYPE: PRT
<213> ORGANISM: Artificial sequence
<220> FEATURE:
<223> OTHER INFORMATION: Penetratin derivative

<400> SEQUENCE: 51

Arg Arg Met Trp Lys Lys Lys
1               5

<210> SEQ ID NO 52
<211> LENGTH: 7
<212> TYPE: PRT
<213> ORGANISM: Artificial sequence
<220> FEATURE:
<223> OTHER INFORMATION: Penetratin derivative
```

```
<400> SEQUENCE: 52

Arg Arg Met Lys Lys Trp Lys
1               5

<210> SEQ ID NO 53
<211> LENGTH: 16
<212> TYPE: PRT
<213> ORGANISM: Artificial sequence
<220> FEATURE:
<223> OTHER INFORMATION: D-penetratin

<400> SEQUENCE: 53

Arg Gln Ile Lys Ile Trp Phe Gln Asn Arg Arg Met Lys Trp Lys Lys
1               5                   10                  15

<210> SEQ ID NO 54
<211> LENGTH: 18
<212> TYPE: PRT
<213> ORGANISM: Artificial sequence
<220> FEATURE:
<223> OTHER INFORMATION: Pegelin (SynB)

<400> SEQUENCE: 54

Arg Gly Gly Arg Leu Ser Tyr Ser Arg Arg Arg Phe Ser Thr Ser Thr
1               5                   10                  15

Gly Arg

<210> SEQ ID NO 55
<211> LENGTH: 13
<212> TYPE: PRT
<213> ORGANISM: Artificial sequence
<220> FEATURE:
<223> OTHER INFORMATION: HIV-TAT

<400> SEQUENCE: 55

Gly Arg Lys Lys Arg Arg Gln Arg Arg Arg Pro Pro Gln
1               5                   10

<210> SEQ ID NO 56
<211> LENGTH: 11
<212> TYPE: PRT
<213> ORGANISM: Artificial sequence
<220> FEATURE:
<223> OTHER INFORMATION: Residues 47-57 of HIV-TAT

<400> SEQUENCE: 56

Tyr Gly Arg Lys Lys Arg Arg Gln Arg Arg Arg
1               5                   10

<210> SEQ ID NO 57
<211> LENGTH: 33
<212> TYPE: PRT
<213> ORGANISM: Artificial sequence
<220> FEATURE:
<223> OTHER INFORMATION: VP22

<400> SEQUENCE: 57

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
                20                  25                  30

Asp
```

-continued

```
<210> SEQ ID NO 58
<211> LENGTH: 18
<212> TYPE: PRT
<213> ORGANISM: Artificial sequence
<220> FEATURE:
<223> OTHER INFORMATION: MAP

<400> SEQUENCE: 58

Lys Leu Ala Leu Lys Leu Ala Leu Lys Ala Leu Lys Ala Ala Leu Lys
1               5                   10                  15

Leu Ala

<210> SEQ ID NO 59
<211> LENGTH: 27
<212> TYPE: PRT
<213> ORGANISM: Artificial sequence
<220> FEATURE:
<223> OTHER INFORMATION: Transportan

<400> SEQUENCE: 59

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 60
<211> LENGTH: 21
<212> TYPE: PRT
<213> ORGANISM: Artificial sequence
<220> FEATURE:
<223> OTHER INFORMATION: Transportan-10

<400> SEQUENCE: 60

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 61
<211> LENGTH: 30
<212> TYPE: PRT
<213> ORGANISM: Artificial sequence
<220> FEATURE:
<223> OTHER INFORMATION: KALA

<400> SEQUENCE: 61

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 62
<211> LENGTH: 21
<212> TYPE: PRT
<213> ORGANISM: Artificial sequence
<220> FEATURE:
<223> OTHER INFORMATION: Pep-1

<400> SEQUENCE: 62

Lys Glu Thr Trp Trp Glu Thr Trp Trp Thr Glu Trp Ser Gln Pro Lys
1               5                   10                  15

Lys Lys Arg Lys Val
            20
```

-continued

```
<210> SEQ ID NO 63
<211> LENGTH: 21
<212> TYPE: PRT
<213> ORGANISM: Artificial sequence
<220> FEATURE:
<223> OTHER INFORMATION: Pep-2

<400> SEQUENCE: 63

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 64
<211> LENGTH: 27
<212> TYPE: PRT
<213> ORGANISM: Artificial sequence
<220> FEATURE:
<223> OTHER INFORMATION: MPG

<400> SEQUENCE: 64

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 65
<211> LENGTH: 19
<212> TYPE: PRT
<213> ORGANISM: Artificial sequence
<220> FEATURE:
<223> OTHER INFORMATION: Vectocell peptide

<400> SEQUENCE: 65

Val Lys Arg Gly Leu Lys Leu Arg His Val Arg Pro Arg Val Thr Arg
1               5                   10                  15

Met Asp Val

<210> SEQ ID NO 66
<211> LENGTH: 14
<212> TYPE: PRT
<213> ORGANISM: Artificial sequence
<220> FEATURE:
<223> OTHER INFORMATION: Vectocell peptide

<400> SEQUENCE: 66

Ser Arg Arg Ala Arg Ser Pro Arg His Leu Gly Ser Gly
1               5                   10

<210> SEQ ID NO 67
<211> LENGTH: 16
<212> TYPE: PRT
<213> ORGANISM: Artificial sequence
<220> FEATURE:
<223> OTHER INFORMATION: Vectocell peptide

<400> SEQUENCE: 67

Leu Arg Arg Glu Arg Gln Ser Arg Leu Arg Arg Glu Arg Gln Ser Arg
1               5                   10                  15

<210> SEQ ID NO 68
<211> LENGTH: 22
<212> TYPE: PRT
<213> ORGANISM: Artificial sequence
<220> FEATURE:
<223> OTHER INFORMATION: Vectocell peptide
```

<400> SEQUENCE: 68

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 69
<211> LENGTH: 29
<212> TYPE: PRT
<213> ORGANISM: Artificial sequence
<220> FEATURE:
<223> OTHER INFORMATION: Wr-T transporter
<220> FEATURE:
<221> NAME/KEY: variant
<222> LOCATION: (22)..(29)
<223> OTHER INFORMATION: /REPLACE= D enantiomer arginine

<400> SEQUENCE: 69

Lys Glu Thr Trp Trp Glu Thr Trp Trp Thr Glu Trp Trp Thr Glu Trp
1               5                   10                  15

Ser Gln Gly Pro Gly Xaa Xaa Xaa Xaa Xaa Xaa Xaa
            20                  25

<210> SEQ ID NO 70
<211> LENGTH: 7
<212> TYPE: PRT
<213> ORGANISM: Artificial sequence
<220> FEATURE:
<223> OTHER INFORMATION: R7

<400> SEQUENCE: 70

Arg Arg Arg Arg Arg Arg Arg
1               5

<210> SEQ ID NO 71
<211> LENGTH: 9
<212> TYPE: PRT
<213> ORGANISM: Artificial sequence
<220> FEATURE:
<223> OTHER INFORMATION: HIV-TAT peptide

<400> SEQUENCE: 71

Arg Lys Lys Arg Arg Gln Arg Arg Arg
1               5

<210> SEQ ID NO 72
<211> LENGTH: 8
<212> TYPE: PRT
<213> ORGANISM: Artificial sequence
<220> FEATURE:
<223> OTHER INFORMATION: R8

<400> SEQUENCE: 72

Arg Arg Arg Arg Arg Arg Arg Arg
1               5

<210> SEQ ID NO 73
<211> LENGTH: 11
<212> TYPE: PRT
<213> ORGANISM: Artificial sequence
<220> FEATURE:
<223> OTHER INFORMATION: R11

<400> SEQUENCE: 73

Arg Arg Arg Arg Arg Arg Arg Arg Arg Arg Arg

```
1               5               10
```

<210> SEQ ID NO 74
<211> LENGTH: 10
<212> TYPE: PRT
<213> ORGANISM: Artificial sequence
<220> FEATURE:
<223> OTHER INFORMATION: QSR8

<400> SEQUENCE: 74

```
Gln Ser Arg Arg Arg Arg Arg Arg Arg Arg
1               5                   10
```

<210> SEQ ID NO 75
<211> LENGTH: 4
<212> TYPE: PRT
<213> ORGANISM: Artificial sequence
<220> FEATURE:
<223> OTHER INFORMATION: NLS

<400> SEQUENCE: 75

```
Arg Lys Arg His
1
```

<210> SEQ ID NO 76
<211> LENGTH: 7
<212> TYPE: PRT
<213> ORGANISM: Artificial sequence
<220> FEATURE:
<223> OTHER INFORMATION: SV40 large T antigen NLS

<400> SEQUENCE: 76

```
Pro Lys Lys Lys Arg Lys Val
1               5
```

<210> SEQ ID NO 77
<211> LENGTH: 16
<212> TYPE: PRT
<213> ORGANISM: Artificial sequence
<220> FEATURE:
<223> OTHER INFORMATION: Nucleoplasmin NLS

<400> SEQUENCE: 77

```
Lys Arg Pro Ala Ala Thr Lys Lys Ala Gly Gln Ala Lys Lys Lys Lys
1               5                   10                  15
```

<210> SEQ ID NO 78
<211> LENGTH: 4
<212> TYPE: PRT
<213> ORGANISM: Artificial sequence
<220> FEATURE:
<223> OTHER INFORMATION: NLS consensus sequence
<220> FEATURE:
<221> NAME/KEY: variant
<222> LOCATION: (2)..(2)
<223> OTHER INFORMATION: /REPLACE= "Arg" or "Lys"
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: variant
<222> LOCATION: (4)..(4)
<223> OTHER INFORMATION: /REPLACE= "Arg" or "Lys"

<400> SEQUENCE: 78

```
Lys Xaa Xaa Xaa
1
```

```
<210> SEQ ID NO 79
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: repeat
<222> LOCATION: (3)..(3)
<223> OTHER INFORMATION: X can be 5 to 20 residues

<400> SEQUENCE: 79

Lys Arg Xaa Lys Lys Lys Lys
1               5

<210> SEQ ID NO 80
<211> LENGTH: 16
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(12)
<223> OTHER INFORMATION: /REPLACE= any amino acid

<400> SEQUENCE: 80

Lys Arg Xaa Xaa Xaa Xaa Xaa Xaa Xaa Xaa Xaa Xaa Lys Lys Lys Lys
1               5                   10                  15

<210> SEQ ID NO 81
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(5)
<223> OTHER INFORMATION: /REPLACE= any amino acid
<220> FEATURE:
<221> NAME/KEY: repeat
<222> LOCATION: (5)..(5)
<223> OTHER INFORMATION: 2 to 10
<220> FEATURE:
<221> NAME/KEY: repeat
<222> LOCATION: (5)..(5)
<223> OTHER INFORMATION: X can be 2 to 10 residues

<400> SEQUENCE: 81

Arg Lys Arg His Xaa Lys Lys
1               5

<210> SEQ ID NO 82
<211> LENGTH: 8
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(6)
<223> OTHER INFORMATION: /REPLACE= any amino acid

<400> SEQUENCE: 82

Arg Lys Arg His Xaa Xaa Lys Lys
1               5
```

```
<210> SEQ ID NO 83
<211> LENGTH: 8
<212> TYPE: PRT
<213> ORGANISM: Artificial sequence
<220> FEATURE:
<223> OTHER INFORMATION: NLS variant

<400> SEQUENCE: 83

Arg Lys Arg His Ile Ile Lys Lys
1               5

<210> SEQ ID NO 84
<211> LENGTH: 9
<212> TYPE: PRT
<213> ORGANISM: Artificial sequence
<220> FEATURE:
<223> OTHER INFORMATION: Oncoprotein c-myc NLS

<400> SEQUENCE: 84

Pro Ala Ala Lys Arg Val Lys Leu Asp
1               5

<210> SEQ ID NO 85
<211> LENGTH: 4
<212> TYPE: PRT
<213> ORGANISM: Artificial sequence
<220> FEATURE:
<223> OTHER INFORMATION: NLS cluster of basic amino acids

<400> SEQUENCE: 85

Lys Lys Lys Lys
1

<210> SEQ ID NO 86
<211> LENGTH: 8
<212> TYPE: PRT
<213> ORGANISM: Artificial sequence
<220> FEATURE:
<223> OTHER INFORMATION: NLS variant

<400> SEQUENCE: 86

Pro Ala Ala Lys Lys Lys Leu Asp
1               5

<210> SEQ ID NO 87
<211> LENGTH: 8
<212> TYPE: PRT
<213> ORGANISM: Artificial sequence
<220> FEATURE:
<223> OTHER INFORMATION: NLS variant

<400> SEQUENCE: 87

Pro Lys Lys Lys Arg Lys Val Leu
1               5

<210> SEQ ID NO 88
<211> LENGTH: 5
<212> TYPE: PRT
<213> ORGANISM: Artificial sequence
<220> FEATURE:
<223> OTHER INFORMATION: NLS variant

<400> SEQUENCE: 88

Lys Lys Lys Arg Lys
1               5
```

```
<210> SEQ ID NO 89
<211> LENGTH: 6
<212> TYPE: PRT
<213> ORGANISM: Artificial sequence
<220> FEATURE:
<223> OTHER INFORMATION: NLS variant

<400> SEQUENCE: 89

Lys Lys Lys Arg Val Lys
1               5

<210> SEQ ID NO 90
<211> LENGTH: 7
<212> TYPE: PRT
<213> ORGANISM: Artificial sequence
<220> FEATURE:
<223> OTHER INFORMATION: NLS variant

<400> SEQUENCE: 90

Lys Lys Lys Arg Lys Val Leu
1               5

<210> SEQ ID NO 91
<211> LENGTH: 7
<212> TYPE: PRT
<213> ORGANISM: Artificial sequence
<220> FEATURE:
<223> OTHER INFORMATION: NLS variant

<400> SEQUENCE: 91

Arg Lys Lys Arg Lys Val Leu
1               5

<210> SEQ ID NO 92
<211> LENGTH: 14
<212> TYPE: PRT
<213> ORGANISM: Artificial sequence
<220> FEATURE:
<223> OTHER INFORMATION: HIV TAT derivative peptide

<400> SEQUENCE: 92

Gly Arg Lys Lys Arg Arg Gln Arg Arg Arg Pro Pro Gln Gln
1               5                   10

<210> SEQ ID NO 93
<211> LENGTH: 5
<212> TYPE: PRT
<213> ORGANISM: Artificial Sequence
<220> FEATURE:
<223> OTHER INFORMATION: SV40 protein derivative

<400> SEQUENCE: 93

Lys Lys Lys Arg Lys
1               5

<210> SEQ ID NO 94
<211> LENGTH: 5
<212> TYPE: PRT
<213> ORGANISM: Artificial Sequence
<220> FEATURE:
<223> OTHER INFORMATION: Linker

<400> SEQUENCE: 94

Ile Ile Leu Val Ile
1               5
```

```
<210> SEQ ID NO 95
<211> LENGTH: 7
<212> TYPE: PRT
<213> ORGANISM: Artificial sequence
<220> FEATURE:
<223> OTHER INFORMATION: Linker

<400> SEQUENCE: 95

Ile Ile Leu Val Ile Ile Ile
1               5

<210> SEQ ID NO 96
<211> LENGTH: 14
<212> TYPE: PRT
<213> ORGANISM: Artificial Sequence
<220> FEATURE:
<223> OTHER INFORMATION: APIM Oligopeptidic compound

<400> SEQUENCE: 96

Met Asp Arg Trp Leu Val Lys Arg Ile Leu Val Ala Thr Lys
1               5                   10

<210> SEQ ID NO 97
<211> LENGTH: 20
<212> TYPE: PRT
<213> ORGANISM: Artificial sequence
<220> FEATURE:
<223> OTHER INFORMATION: APIM Oligopeptidic compound

<400> SEQUENCE: 97

Met Asp Arg Trp Leu Val Lys Arg Ile Leu Lys Lys Arg Lys Val
1               5                   10                  15

Ala Thr Lys Gly
            20

<210> SEQ ID NO 98
<211> LENGTH: 34
<212> TYPE: PRT
<213> ORGANISM: Artificial sequence
<220> FEATURE:
<223> OTHER INFORMATION: MDR2
<220> FEATURE:
<221> NAME/KEY: mod_res
<222> LOCATION: (34)..(34)
<223> OTHER INFORMATION: 5-Carboxyfluorescein coupled by Aminohexanoic
      acid

<400> SEQUENCE: 98

Met Asp Arg Trp Leu Val Lys Gly Ala Gln Pro Lys Lys Arg Lys
1               5                   10                  15

Val Leu Arg Gln Ile Lys Ile Trp Phe Gln Asn Arg Arg Met Lys Trp
            20                  25                  30

Lys Lys

<210> SEQ ID NO 99
<211> LENGTH: 28
<212> TYPE: PRT
<213> ORGANISM: Artificial sequence
<220> FEATURE:
<223> OTHER INFORMATION: MDR27
<220> FEATURE:
<221> NAME/KEY: mod_res
<222> LOCATION: (28)..(28)
<223> OTHER INFORMATION: 5-Carboxyfluorescein coupled by Aminohexanoic
      acid

<400> SEQUENCE: 99
```

Met Asp Arg Trp Leu Val Lys Gly Ala Trp Lys Lys Arg Val Lys
1               5                   10                  15

Ile Ile Arg Lys Lys Arg Arg Gln Arg Arg Lys
            20                  25

<210> SEQ ID NO 100
<211> LENGTH: 27
<212> TYPE: PRT
<213> ORGANISM: Artificial sequence
<220> FEATURE:
<223> OTHER INFORMATION: MDR26-0

<400> SEQUENCE: 100

Met Asp Arg Trp Leu Val Lys Gly Ala Trp Lys Lys Arg Lys Ile
1               5                   10                  15

Ile Arg Lys Lys Arg Arg Gln Arg Arg Arg Gly
            20                  25

<210> SEQ ID NO 101
<211> LENGTH: 27
<212> TYPE: PRT
<213> ORGANISM: Artificial sequence
<220> FEATURE:
<223> OTHER INFORMATION: MDR26-1
<220> FEATURE:
<221> NAME/KEY: mod_res
<222> LOCATION: (27)..(27)
<223> OTHER INFORMATION: 5-Carboxyfluorescein coupled by Aminohexanoic
      acid

<400> SEQUENCE: 101

Met Asp Arg Trp Leu Val Lys Gly Ala Trp Lys Lys Arg Lys Ile
1               5                   10                  15

Ile Arg Lys Lys Arg Arg Gln Arg Arg Arg Lys
            20                  25

<210> SEQ ID NO 102
<211> LENGTH: 27
<212> TYPE: PRT
<213> ORGANISM: Artificial sequence
<220> FEATURE:
<223> OTHER INFORMATION: MDR26-2
<220> FEATURE:
<221> NAME/KEY: MOD_RES
<222> LOCATION: (27)..(27)
<223> OTHER INFORMATION: 5-Carboxyfluorescein coupled by Aminohexanoic
      acid

<400> SEQUENCE: 102

Met Asp Arg Trp Leu Val Lys Arg Ile Trp Lys Lys Arg Lys Ile
1               5                   10                  15

Ile Arg Lys Lys Arg Arg Gln Arg Arg Arg Lys
            20                  25

<210> SEQ ID NO 103
<211> LENGTH: 27
<212> TYPE: PRT
<213> ORGANISM: Artificial sequence
<220> FEATURE:
<223> OTHER INFORMATION: MDR26-3
<220> FEATURE:
<221> NAME/KEY: MOD_RES
<222> LOCATION: (27)..(27)
<223> OTHER INFORMATION: 5-Carboxyfluorescein coupled by Aminohexanoic
      acid

<400> SEQUENCE: 103

Met Asp Arg Trp Leu Val Lys Trp Trp Lys Lys Arg Lys Ile
1               5                   10                  15

Ile Arg Lys Lys Arg Arg Gln Arg Arg Arg Lys
            20                  25

<210> SEQ ID NO 104
<211> LENGTH: 27
<212> TYPE: PRT
<213> ORGANISM: Artificial sequence
<220> FEATURE:
<223> OTHER INFORMATION: MDR26-4
<220> FEATURE:
<221> NAME/KEY: MOD_RES
<222> LOCATION: (27)..(27)
<223> OTHER INFORMATION: 5-Carboxyfluorescein coupled by Aminohexanoic
      acid

<400> SEQUENCE: 104

Met Asp Arg Trp Leu Val Lys Trp Trp Arg Lys Arg His Ile Ile Lys
1               5                   10                  15

Lys Arg Lys Lys Arg Arg Gln Arg Arg Arg Lys
            20                  25

<210> SEQ ID NO 105
<211> LENGTH: 29
<212> TYPE: PRT
<213> ORGANISM: Artificial sequence
<220> FEATURE:
<223> OTHER INFORMATION: MDR26-7
<220> FEATURE:
<221> NAME/KEY: MOD_RES
<222> LOCATION: (29)..(29)
<223> OTHER INFORMATION: 5-Carboxyfluorescein coupled by Aminohexanoic
      acid

<400> SEQUENCE: 105

Met Asp Arg Trp Leu Val Lys Arg Ile Trp Lys Lys Arg Lys Ile
1               5                   10                  15

Ile Arg Arg Arg Arg Arg Arg Arg Arg Arg Arg Lys
            20                  25

<210> SEQ ID NO 106
<211> LENGTH: 33
<212> TYPE: PRT
<213> ORGANISM: Artificial sequence
<220> FEATURE:
<223> OTHER INFORMATION: MDR26-8
<220> FEATURE:
<221> NAME/KEY: MOD_RES
<222> LOCATION: (33)..(33)
<223> OTHER INFORMATION: 5-Carboxyfluorescein coupled by Aminohexanoic
      acid

<400> SEQUENCE: 106

Met Asp Arg Trp Leu Val Lys Arg Ile Trp Lys Lys Arg Lys Ile
1               5                   10                  15

Ile Arg Gln Ile Lys Ile Trp Phe Gln Asn Arg Met Lys Trp Lys
            20                  25                  30

Lys

<210> SEQ ID NO 107
<211> LENGTH: 28
<212> TYPE: PRT
<213> ORGANISM: Artificial sequence
<220> FEATURE:
<223> OTHER INFORMATION: MDr26-10
<220> FEATURE:

-continued

```
<221> NAME/KEY: MOD_RES
<222> LOCATION: (28)..(28)
<223> OTHER INFORMATION: 5-Carboxyfluorescein coupled by Aminohexanoic
      acid

<400> SEQUENCE: 107

Met Asp Arg Phe Leu Val Lys Gly Ala Trp Arg Lys Arg His Ile Ile
1               5                   10                  15

Lys Lys Arg Lys Lys Arg Arg Gln Arg Arg Lys
            20                  25

<210> SEQ ID NO 108
<211> LENGTH: 26
<212> TYPE: PRT
<213> ORGANISM: Artificial sequence
<220> FEATURE:
<223> OTHER INFORMATION: MDR26-72
<220> FEATURE:
<221> NAME/KEY: MOD_RES
<222> LOCATION: (26)..(26)
<223> OTHER INFORMATION: Coupled to fluorescein

<400> SEQUENCE: 108

Met Asp Arg Trp Leu Val Lys Trp Lys Lys Arg Lys Ile Arg Arg
1               5                   10                  15

Arg Arg Arg Arg Arg Arg Arg Arg Arg Lys
            20                  25

<210> SEQ ID NO 109
<211> LENGTH: 24
<212> TYPE: PRT
<213> ORGANISM: Artificial sequence
<220> FEATURE:
<223> OTHER INFORMATION: MDR26-32
<220> FEATURE:
<221> NAME/KEY: MOD_RES
<222> LOCATION: (24)..(24)
<223> OTHER INFORMATION: Coupled to fluorescein

<400> SEQUENCE: 109

Met Asp Arg Trp Leu Val Lys Trp Lys Lys Arg Lys Ile Arg Lys
1               5                   10                  15

Lys Arg Arg Gln Arg Arg Arg Lys
            20

<210> SEQ ID NO 110
<211> LENGTH: 23
<212> TYPE: PRT
<213> ORGANISM: Artificial sequence
<220> FEATURE:
<223> OTHER INFORMATION: MDR26-42
<220> FEATURE:
<221> NAME/KEY: MOD_RES
<222> LOCATION: (23)..(23)
<223> OTHER INFORMATION: Coupled to fluorescein

<400> SEQUENCE: 110

Met Asp Arg Trp Leu Val Lys Trp Arg Lys Arg His Ile Arg Lys Lys
1               5                   10                  15

Arg Arg Gln Arg Arg Arg Lys
            20

<210> SEQ ID NO 111
<211> LENGTH: 25
<212> TYPE: PRT
<213> ORGANISM: Artificial sequence
<220> FEATURE:
```

```
<223> OTHER INFORMATION: MDR24-43
<220> FEATURE:
<221> NAME/KEY: MOD_RES
<222> LOCATION: (25)..(25)
<223> OTHER INFORMATION: Coupled to fluorescein-5-isothiocyanate

<400> SEQUENCE: 111

Met Asp Arg Trp Leu Val Lys Gly Ala Trp Arg Lys Arg His Ile Arg
1               5                   10                  15

Lys Lys Arg Arg Gln Arg Arg Arg Lys
            20                  25

<210> SEQ ID NO 112
<211> LENGTH: 25
<212> TYPE: PRT
<213> ORGANISM: Artificial sequence
<220> FEATURE:
<223> OTHER INFORMATION: MDR26-72-0
<220> FEATURE:
<221> NAME/KEY: MOD_RES
<222> LOCATION: (1)..(1)
<223> OTHER INFORMATION: ACETYLATION

<400> SEQUENCE: 112

Met Asp Arg Trp Leu Val Lys Trp Lys Lys Arg Lys Ile Arg Arg
1               5                   10                  15

Arg Arg Arg Arg Arg Arg Arg Arg Arg
            20                  25

<210> SEQ ID NO 113
<211> LENGTH: 25
<212> TYPE: PRT
<213> ORGANISM: Artificial sequence
<220> FEATURE:
<223> OTHER INFORMATION: MDR26-72-A
<220> FEATURE:
<221> NAME/KEY: MOD_RES
<222> LOCATION: (1)..(1)
<223> OTHER INFORMATION: ACETYLATION

<400> SEQUENCE: 113

Met Asp Arg Ala Leu Val Lys Trp Lys Lys Arg Lys Ile Arg Arg
1               5                   10                  15

Arg Arg Arg Arg Arg Arg Arg Arg Arg
            20                  25

<210> SEQ ID NO 114
<211> LENGTH: 24
<212> TYPE: PRT
<213> ORGANISM: Artificial sequence
<220> FEATURE:
<223> OTHER INFORMATION: MDR26-72-011
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (24)..(24)
<223> OTHER INFORMATION: 5-Carboxyfluorescein coupled by Aminohexanoic
      acid

<400> SEQUENCE: 114

Met Asp Arg Trp Leu Val Lys Lys Lys Lys Arg Lys Arg Arg Arg
1               5                   10                  15

Arg Arg Arg Arg Arg Arg Arg Lys
            20
```

```
<210> SEQ ID NO 115
<211> LENGTH: 23
<212> TYPE: PRT
<213> ORGANISM: Artificial sequence
<220> FEATURE:
<223> OTHER INFORMATION: MDR26-01
<220> FEATURE:
<221> NAME/KEY: MOD_RES
<222> LOCATION: (1)..(1)
<223> OTHER INFORMATION: ACETYLATION

<400> SEQUENCE: 115

Met Asp Arg Trp Leu Val Lys Lys Lys Arg Lys Arg Arg Arg Arg
1               5                   10                  15

Arg Arg Arg Arg Arg Arg Arg
            20

<210> SEQ ID NO 116
<211> LENGTH: 35
<212> TYPE: PRT
<213> ORGANISM: Artificial sequence
<220> FEATURE:
<223> OTHER INFORMATION: MDR34
<220> FEATURE:
<221> NAME/KEY: MOD_RES
<222> LOCATION: (35)..(35)
<223> OTHER INFORMATION: 5-Carboxyfluorescein coupled by Aminohexanoic
      acid

<400> SEQUENCE: 116

Met Asp Arg Trp Leu Val Lys Arg Ile Trp Lys Lys Lys Arg Lys Ile
1               5                   10                  15

Ile Arg Trp Leu Val Lys Trp Trp Trp Arg Lys Lys Arg Arg Gln Arg
            20                  25                  30

Arg Arg Lys
        35

<210> SEQ ID NO 117
<211> LENGTH: 27
<212> TYPE: PRT
<213> ORGANISM: Artificial sequence
<220> FEATURE:
<223> OTHER INFORMATION: RI-MDR26-3
<220> FEATURE:
<221> NAME/KEY: MOD_RES
<222> LOCATION: (1)..(1)
<223> OTHER INFORMATION: Coupled to fluorescein-5-isothiocyanate

<400> SEQUENCE: 117

Lys Arg Arg Arg Gln Arg Arg Lys Lys Arg Ile Ile Lys Arg Lys Lys
1               5                   10                  15

Lys Trp Trp Trp Lys Val Leu Trp Arg Asp Met
            20                  25

<210> SEQ ID NO 118
<211> LENGTH: 7
<212> TYPE: PRT
<213> ORGANISM: Artificial sequence
<220> FEATURE:
<223> OTHER INFORMATION: APIM sequence

<400> SEQUENCE: 118

Met Asp Arg Trp Leu Val Lys
1               5

<210> SEQ ID NO 119
```

```
<211> LENGTH: 7
<212> TYPE: PRT
<213> ORGANISM: Artificial sequence
<220> FEATURE:
<223> OTHER INFORMATION: APIM sequence

<400> SEQUENCE: 119

Met Asp Arg Phe Leu Val Lys
1               5

<210> SEQ ID NO 120
<211> LENGTH: 7
<212> TYPE: PRT
<213> ORGANISM: Artificial sequence
<220> FEATURE:
<223> OTHER INFORMATION: APIM sequence
<220> FEATURE:
<221> NAME/KEY: MOD_RES
<222> LOCATION: (1)..(1)
<223> OTHER INFORMATION: ACETYLATION

<400> SEQUENCE: 120

Met Asp Arg Trp Leu Val Lys
1               5

<210> SEQ ID NO 121
<211> LENGTH: 7
<212> TYPE: PRT
<213> ORGANISM: Artificial sequence
<220> FEATURE:
<223> OTHER INFORMATION: APIM sequence
<220> FEATURE:
<221> NAME/KEY: MOD_RES
<222> LOCATION: (1)..(1)
<223> OTHER INFORMATION: ACETYLATION

<400> SEQUENCE: 121

Met Asp Arg Ala Leu Val Lys
1               5

<210> SEQ ID NO 122
<211> LENGTH: 7
<212> TYPE: PRT
<213> ORGANISM: Artificial sequence
<220> FEATURE:
<223> OTHER INFORMATION: APIM sequence

<400> SEQUENCE: 122

Lys Val Leu Trp Arg Asp Met
1               5

<210> SEQ ID NO 123
<211> LENGTH: 8
<212> TYPE: PRT
<213> ORGANISM: Artificial sequence
<220> FEATURE:
<223> OTHER INFORMATION: NLS

<400> SEQUENCE: 123

Pro Lys Lys Lys Arg Lys Val Leu
1               5

<210> SEQ ID NO 124
<211> LENGTH: 6
<212> TYPE: PRT
<213> ORGANISM: Artificial sequence
<220> FEATURE:
<223> OTHER INFORMATION: NLS#
```

-continued

```
<400> SEQUENCE: 124

Lys Lys Lys Arg Val Lys
1               5

<210> SEQ ID NO 125
<211> LENGTH: 5
<212> TYPE: PRT
<213> ORGANISM: Artificial sequence
<220> FEATURE:
<223> OTHER INFORMATION: NLS

<400> SEQUENCE: 125

Lys Lys Lys Arg Lys
1               5

<210> SEQ ID NO 126
<211> LENGTH: 8
<212> TYPE: PRT
<213> ORGANISM: Artificial sequence
<220> FEATURE:
<223> OTHER INFORMATION: NLS

<400> SEQUENCE: 126

Arg Lys Arg His Ile Ile Lys Lys
1               5

<210> SEQ ID NO 127
<211> LENGTH: 4
<212> TYPE: PRT
<213> ORGANISM: Artificial sequence
<220> FEATURE:
<223> OTHER INFORMATION: NLS

<400> SEQUENCE: 127

Arg Lys Arg His
1

<210> SEQ ID NO 128
<211> LENGTH: 5
<212> TYPE: PRT
<213> ORGANISM: Artificial sequence
<220> FEATURE:
<223> OTHER INFORMATION: NLS

<400> SEQUENCE: 128

Lys Arg Lys Lys Lys
1               5

<210> SEQ ID NO 129
<211> LENGTH: 15
<212> TYPE: PRT
<213> ORGANISM: Artificial sequence
<220> FEATURE:
<223> OTHER INFORMATION: CPP

<400> SEQUENCE: 129

Arg Gln Ile Lys Ile Trp Phe Gln Asn Arg Arg Met Lys Trp Lys
1               5                   10                  15

<210> SEQ ID NO 130
<211> LENGTH: 9
<212> TYPE: PRT
<213> ORGANISM: Artificial sequence
<220> FEATURE:
<223> OTHER INFORMATION: CPP
```

```
<400> SEQUENCE: 130

Arg Lys Lys Arg Arg Gln Arg Arg
1               5

<210> SEQ ID NO 131
<211> LENGTH: 10
<212> TYPE: PRT
<213> ORGANISM: Artificial sequence
<220> FEATURE:
<223> OTHER INFORMATION: CPP

<400> SEQUENCE: 131

Arg Lys Lys Arg Arg Gln Arg Arg Arg Gly
1               5                   10

<210> SEQ ID NO 132
<211> LENGTH: 11
<212> TYPE: PRT
<213> ORGANISM: Artificial sequence
<220> FEATURE:
<223> OTHER INFORMATION: CPP

<400> SEQUENCE: 132

Arg Arg Arg Arg Arg Arg Arg Arg Arg Arg Arg
1               5                   10

<210> SEQ ID NO 133
<211> LENGTH: 9
<212> TYPE: PRT
<213> ORGANISM: Artificial sequence
<220> FEATURE:
<223> OTHER INFORMATION: CPP

<400> SEQUENCE: 133

Arg Arg Arg Gln Arg Arg Lys Lys Arg
1               5

<210> SEQ ID NO 134
<211> LENGTH: 5
<212> TYPE: PRT
<213> ORGANISM: Artificial sequence
<220> FEATURE:
<223> OTHER INFORMATION: 2nd APIM sequence

<400> SEQUENCE: 134

Arg Trp Leu Val Lys
1               5
```

OLIGOPEPTIDIC COMPOUNDS AND USES THEREOF

RELATED APPLICATIONS

This application is a U.S. National Phase of International Application No. PCT/GB2009/000489, filed Feb. 20, 2009, designating the U.S. and published in English on Aug. 27, 2009 as WO 2009/104001 A2, which claims the benefit of Great Britain Application No. 0803352.4, filed Feb. 22, 2008 and U.S. Provisional Application No. 61/100,584, filed Sep. 26, 2008.

FIELD OF THE INVENTION

The present invention relates to novel agents, pharmaceutical compositions, and their use in therapy, particularly any therapy where it is desirable or advantageous to reduce or prevent the proliferation or growth of cells such as in the treatment of hyperproliferative diseases or indeed any condition which requires or is responsive to cytostatic therapy. The invention is based on the identification of novel interactions between the proliferating cell nuclear antigen (PCNA) and various proteins involved in DNA repair, maintenance and cell cycle regulation and the consequent identification of a novel pentapeptide motif responsible for such interactions, which we have termed APIM. Accordingly, the present invention more particularly relates to peptides or mimetics thereof comprising such a motif and which are capable of interacting with PCNA, pharmaceutical compositions comprising such agents, and the use of such agents in therapy, particularly therapies involving the reduction or prevention of cell proliferation, as indicated above. Also provided are therapeutic methods which comprise the use of an agent comprising a PCNA interacting motif, preferably in combination with a cytostatic agent.

BACKGROUND OF THE INVENTION

Human and animal cells are exposed to a variety of causes of DNA damage such as reactive oxygen species, UV light, x-rays and endogenous or exogenous cytostatic agents.

Cytostatic agents are agents which inhibit or suppress cellular growth and/or multiplication (proliferation/replication), for example by damaging DNA or by interfering with the cellular replication machinery. Alkylating agents are a class of cytostatic agents, some of which are used clinically or for research purposes.

Alkylating agents cause DNA damage by modifying bases at N or O atoms. The type of damage depends on the type of agent, with most agents causing a specific DNA modification. DNA damage includes alkylation adducts and inter strand cross-links which may lead to miscoding during replication and/or replication blocks followed by double strand breaks or translesion synthesis.

Human and animal cells possess various DNA repair systems including base excision repair, nucleotide excision repair and mismatch repair. An example is the human DNA oxidative demethylase, hABH2, which reconverts 3-methylcytosine (3meC) into cytosine and 1-methyladenine (1meA) into adenine by oxidative demethylation.

Close co-ordination between DNA repair and cell-cycle regulated DNA replication is essential for genome integrity. It is important that in the presence of damage, DNA replication is halted until the damage has been repaired, otherwise mutations arise and are propagated. One protein known to be involved in both DNA replication and DNA repair is proliferating cell nuclear antigen (PCNA).

PCNA is member of the sliding clamp family of proteins which are functionally conserved from bacteria to higher eukaryotes, and whose main function is to provide replicative polymerases with the high processivity needed for duplication of the genome. In live S-phase cells, PCNA tagged with green fluorescent protein (GRP) forms distinct foci representing sites of replication. It can therefore be used as an S-phase marker.

Numerous proteins involved in cellular processes such as DNA repair, chromatin assembly, epigenetic and chromatin remodelling, sister-chromatid cohesion, cell cycle control and survival are localised in so-called replication factories which contain more than a dozen replication forks. Many of these proteins interact with PCNA through the conserved PCNA interacting peptide sequence called the PIP-box (QxxL/I/MxxF/DF/Y), wherein x can be any amino acid. An alternative PCNA binding motif called the KAx box was identified using a peptide display library, but this motif has not been verified to be important for PCNA interactions in vivo.

Various proteins interact with PCNA and some of these proteins, including hABH2, have been shown to co-localise with PCNA in replication foci. However, co-localisation in itself does not imply that there is any direct or indirect interaction between co-localising proteins. Indeed, the absence in hABH2 of PCNA-binding motifs such as the PIP-box or the KAx box would suggest that hABH2 does not interact with PCNA.

DESCRIPTION OF THE INVENTION

In work leading up to the present invention, the inventors have surprisingly found that various proteins interact with PCNA via a novel PCNA interacting motif. In one of these proteins, hABH2, this motif is located at the N-terminus. The inventors established that this motif is both essential and sufficient for interaction with PCNA (see Example 1).

As explained in more detail in the Examples below, to explore the function of this PCNA interacting motif in DNA repair of alkylating damage, cell lines expressing a recombinant peptide comprising the motif were exposed to various doses of MMS (methyl methanesulfonate) which is an $S_N2$ alkylating agent that causes the formation of 3-methylcytosine and 1-methyladenine. It was found that expression of the recombinant peptide comprising the motif sensitised cells to DNA damage caused by MMS, indicating that the recombinant peptide comprising the motif competitively inhibited the interaction between PCNA and hABH2.

Other agents including BCNU, temozolomide (TZM) and mitomycin c (MMC) which cause other kinds of DNA damage were also tested and to their great surprise, the inventors found that the recombinant peptide comprising the motif also sensitised cells to the damage caused by these agents. This was entirely unexpected, because BCNU is an $O^6$-chloroethylating agent that mainly leads to interstrand crosslinks as well as some mono-base cyclic adducts (1,N(6)ethanoadenine), TZM is reported to be an $O^6G$ methylating agent, and MMC causes interstrand cross links via N-alkylation of guanine in CpGs, and hABH2 does not repair these types of DNA damage. Instead, there are other enzymes which repair this kind of damage, for example the damage by TZM is repaired directly by $O^6$-methylguanine-DNA transferase (MGMT). These findings indicate that the recombinant peptide comprising the motif does not merely inhibit the interaction between hABH2 and PCNA, and that other proteins may be involved, namely that other proteins may interact with PCNA via the novel motif.

The inventors also found that expression of the recombinant peptide comprising the motif increased the cytotoxic effect of cytostatic agents (specifically MMS) beyond that observed in cell lines from ABH2 knock-out mice, i.e. mice which do not possess ABH2, further indicating that the recombinant peptide comprising the motif has a wider-ranging effect, and likely inhibits other proteins in addition to hABH2.

These surprising findings have led the inventors to propose a therapeutic use for a peptide comprising a PCNA binding motif.

The novel PCNA binding motif of the invention, termed APIM, has been characterised and may be defined as follows:

$$X_1X_2X_3X_{3'}X_{1'}, \quad \text{(SEQ ID NO: 1)}$$

wherein $X_1$ and $X_{1'}$ are independently selected from the group of basic amino acids, $X_2$ is a lipophilic amino acid and $X_3$ and $X_{3'}$ are independently selected from the group of uncharged, preferably non-polar amino acids.

A peptide (or oligopeptidic compound) capable of interacting with PCNA may contain or comprise such a peptide (or sequence) motif. Thus, an oligopeptidic compound capable of interacting with PCNA and comprising such a motif is disclosed herein and may represent certain aspects of the present invention.

For example, in one embodiment, the present invention may provide an oligopeptidic compound which is capable of interacting with PCNA and which comprises the motif $X_1X_2X_3X_{3'}X_{1'}$ (SEQ ID NO: 1), wherein $X_1$ and $X_{1'}$ are independently selected from the group of basic amino acids, $X_2$ is a lipophilic amino acid and $X_3$ and $X_{3'}$ are independently selected from the group of uncharged, preferably non-polar amino acids, wherein the oligopeptidic compound is further characterised by at least one of the following:

(i) the oligopeptidic compound comprises at least 11 amino acids or equivalent subunits;
(ii) $X_2$ is not phenylalanine;
(iii) the oligopeptidic compound comprises at least one D-amino acid;
(iv) the oligopeptidic compound comprises at least one signal sequence, namely a sequence which directs the oligopeptidic compound to a particular location, for example into a cell (e.g. a cell penetrating sequence which directs the oligopeptidic compound into a cell) and/or into a particular cellular compartment (e.g. a nuclear localisation signal which directs the oligopeptidic compound into the nucleus); and
(iv) the oligopeptidic compound comprises the motif [K/R]-F-[L/I/V]-[L/I/V]-[K/R](SEQ ID NO: 27).

In particular, in such an embodiment the oligopeptidic compound comprises a nuclear localisation signal sequence. In another embodiment the oligopeptidic compound comprises a cell penetrating sequence (cell penetrating peptide). In a still further embodiment the oligopeptidic compound comprises a cell penetrating sequence and a nuclear localisation sequence.

Thus, it will be seen that in such embodiments the compound of the invention may take the form of a construct containing (i.e. comprising) an oligopeptidic compound which comprises a PCNA interacting motif as defined above, together with at least one signal sequence. In this aspect the invention may accordingly be seen to provide a construct comprising an oligopeptidic compound which is capable of interacting with PCNA and which comprises the motif $X_1X_2X_3X_{3'}X_{1'}$ (SEQ ID NO: 1), wherein $X_1$ and $X_{1'}$ are independently selected from the group of basic amino acids, $X_2$ is a lipophilic amino acid and $X_3$ and $X_{3'}$ are independently selected from the group of uncharged, preferably non-polar amino acids, together with at least one signal sequence.

As noted above the novel motif of the invention has been determined to mediate the interaction of an oligopeptidic compound (e.g. peptide) or protein containing such a motif with PCNA.

The interaction may be direct or indirect, and may involve direct binding of the motif to the PCNA, or the motif may bind indirectly, for example binding may be mediated by another molecule. This reference to "PCNA-interacting" or "PCNA-binding" can thus include any form of interaction, and both direct and indirect binding.

Any reference herein to a "motif" should be understood to mean $X_1X_2X_3X_{3'}X_{1'}$ as defined herein.

Preferably, $X_1$ and $X_{1'}$ are independently selected from lysine (K), arginine (R), histidine (H), ornithine (Orn), methyllysine (MeK) and acetyllysine (AcK), and more preferably K, R and H, or K and R;

$X_2$ is preferably an aromatic amino acid, more preferably it is selected from phenylalanine (F), tryptophan (W), tyrosine (Y), tert.-butylglycine, cyclohexylalanine, tert.-butylphenylalanine, biphenylalanine and tri tert-butyltryptophan (in certain embodiments this list may exclude F), particularly F, W and Y, or W and Y, F and Y, or F and W or in specific embodiments $X_2$ may be F, or W or Y;

$X_3$ and $X_{3'}$ are preferably aliphatic amino acids and may for example be independently selected from leucine (L), isoleucine (I), valine (V), alanine (A) methionine (M) and norleucine (Nor);

Preferably, $X_3$ and $X_{3'}$ are not both A, more preferably $X_3$ and $X_{3'}$ are selected from L, I, V and M, even more preferably from L, I and V.

The binding of the motif to PCNA may in certain embodiments be improved when $X_2$ is W or Y. Thus, in one embodiment, $X_2$ is not F. However, as indicated above, in other embodiments it may be F.

Thus, the invention may provide an oligopeptidic compound comprising the motif [K/R]-[F/Y/W]-[L/I/V/A/M]-[L/I/V/A/M]-[K/R] (SEQ ID NO: 28), wherein said oligopeptidic compound is capable of interacting with PCNA.

In another embodiment the motif may be defined as: [K/R]-[Y/W]-[L/I/V/A/M]-[L/I/V/A/M]-[K/R](SEQ ID NO: 29).

In another embodiment the motif may be defined as:

$$\text{[K/R]-[F/Y/W]-[L/I/V/A]-[L/I/V/A]-[K/R]}. \quad \text{(SEQ ID NO: 30)}$$

In another embodiment the motif may be defined as: [K/R]-[Y/W]-[L/I/V/A]-[L/I/V/A]-[K/R] (SEQ ID NO: 31).

In another embodiment the motif may be defined as: [K/R]-[F/W]-[L/I/V/A/M]-[L/I/V/A/M]-[K/R] (SEQ ID NO: 32).

In another embodiment the motif may be defined as:

$$\text{[K/R]-[F/W]-[L/I/V/A]-[L/I/V/A]-[K/R]}. \quad \text{(SEQ ID NO: 33)}$$

In another embodiment the motif may be defined as: [K/R]-[F/W]-[L/I/V]-[L/I/V]-[K/R] (SEQ ID NO: 34).

In another embodiment the motif may be defined as: [K/R]-[F/Y/W]-[L/I/V]-[L/I/V]-[K/R] (SEQ ID NO: 35).

In yet another embodiment the motif may be defined as: [K/R]-[Y/W]-[L/I/V]-[L/I/V]-[K/R] (SEQ ID NO: 36).

In yet another embodiment the motif may be defined as: [K/R]-F-[L/I/V]-[L/I/V]-[K/R] (SEQ ID NO: 37).

The oligopeptidic compound is preferably an isolated compound.

In a preferred embodiment, the oligopeptidic compound has or comprises the sequence RFLVK (SEQ ID NO: 2). In other preferred embodiments, the oligopeptidic compound has or comprises a sequence selected from KFLLR (SEQ ID NO: 3), KYLLR (SEQ ID NO: 4), KWLLR(SEQ ID NO: 5), KYILR (SEQ ID NO: 6), KYVLR (SEQ ID NO: 7), RFLLR (SEQ ID NO: 8), RYLLR (SEQ ID NO: 9), RWLLR (SEQ ID NO: 10), RYILR (SEQ ID NO: 11), RYVLR (SEQ ID NO: 12), RFLIR (SEQ ID NO: 13), RYLVR (SEQ ID NO: 14) RWLMR (SEQ ID NO: 15), RYVLR (SEQ ID NO: 16), RYVIR (SEQ ID NO: 17), RWLVK (SEQ ID NO: 18), RYLVK (SEQ ID NO: 19), RWLIK (SEQ ID NO: 20), RWIVK (SEQ ID NO: 21), RWVVK (SEQ ID NO: 22), RWAVK (SEQ ID NO: 23), RYVVK (SEQ ID NO: 24), RYLIK (SEQ ID NO: 25) or RYLMK (SEQ ID NO: 26). These specific sequences are listed by way of example and they are not intended to be limiting on the scope of the present invention.

In one preferred embodiment, the oligopeptidic compound of the invention also comprises a signal sequence which targets the motif to a specific cell type, facilitates entry of the compound into a cell, and/or localises the compound to a specific intracellular compartment, preferably the nucleus.

The signal sequence may thus be viewed as any sequence which acts to localise, or alternatively put, to direct, translocate or transport, the oligopeptidic compound to any desired location e.g. to any desired cellular or subcellular location. In preferred embodiments the desired location is a cell (i.e. the inside of a cell) and/or the nucleus of a cell.

Thus the signal sequence may be a sequence which acts to transport the oligopeptidic compound into a cell, or across a cell membrane (i.e. into the interior of a cell). It may thus be a so-called "cell penetrating" sequence (or more particularly "cell penetrating peptide") also known in the art as a protein transduction domain (PTD) or protein transduction sequence.

Accordingly, as noted above a preferred embodiment of the invention is a construct comprising (i) an oligopeptidic compound comprising an APIM motif (i.e. a PCNA-interacting motif) as defined herein, and (ii) a cell penetrating sequence (more particularly a cell penetrating peptide).

Cell penetrating peptide (CPP) technology has developed greatly over recent years and a wide variety of cell penetrating peptides are known and described in the art and indeed a range of such peptides are commercially available. Cell penetrating peptides may vary greatly in size, sequence and charge, and indeed in their mechanism of function (which is presently not known for some peptides and not fully elucidated for others), but share the common ability to translocate across the plasma membrane and deliver an attached or associated moiety (the so-called "cargo") into the cytoplasm, or even in some cases the nucleus, of a cell. CPPs are thus peptide-based delivery vectors.

CPPs may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and or they may be synthetically-derived, e.g. from chimeric proteins or synthetic polypeptides such as polyarginine. As noted above, there is not a single mechanism responsible for the transduction effect and hence the design of CPPs may be based on different structures and sequences. Cell penetrating peptides are reviewed in Jarver et al. 2006 Biochimica et Biophysica Acta 1758, pages 260-263 and Table 2 below lists various representative peptides. U.S. Pat. No. 6,645,501 further describes various cell penetrating peptides which might be used.

TABLE 2

| CPP | SEQUENCE | REFERENCE |
|---|---|---|
| Antp Class | | |
| Penetratin | RQIKIWFQNRRMKWKK (SEQ ID NO: 38) | Bolton (2000) Eur. J. Neuro. 12: 287 |
| Penatratin derivatives | RRMKWKK( SEQ ID NO: 39)<br>NRRMKWKK (SEQ ID NO: 40)<br>QNRRMKWKK (SEQ ID NO: 41)<br>FQNRRMKWKK (SEQ ID NO: 42)<br>RREKWKK (SEQ ID NO: 43)<br>RRQKWKK (SEQ ID NO: 44)<br>KRMKWKK (SEQ ID NO: 45)<br>RKMKWKK (SEQ ID NO: 46)<br>RROKWKK (SEQ ID NO: 47)<br>RRMKQKK (SEQ ID NO: 48)<br>RRMKWFK (SEQ ID NO: 49)<br>RORKWKK (SEQ ID NO: 50)<br>RRMWKKK (SEQ ID NO: 51)<br>RRMKKWK (SEQ ID NO: 52)<br>(using standard single amino acid notation, ornithine (O), diaminobutyric acid (B), norleucine (N)) | US 6472507<br>EP4855781<br>WO 97/12912 |
| D-Penetratin | rqikiwfqnrrmkwick (SEQ ID NO: 53) | Rouselle, C. et al. (2000) Mol. Pharm 57: 679 |
| Protegrin Class | | |
| Pegelin (SynB) | RGGRLSYSRRRFSTSTGR (SEQ ID NO: 54) | Rouselle, C. et al. (2000) Mol. Pharm 57: 679 |

TABLE 2-continued

| CPP | SEQUENCE | REFERENCE |
|---|---|---|
| HIV-TAT Class | | |
| HIV-TAT | GRKKRRQRRRPPQ (SEQ ID NO: 55) | Vives E. J Biol, Chem 1997, 272: 16010 Snyder (2004) PLOS 2: 186 |
| 47-57 OF HIV-TAT | YGRKKRRQRRR (SEQ ID NO: 56) | Potocky et al. (2003) JBC |
| VP22 | DAATATRGRSAASRPTERPRAPARSASRPRRVD (SEQ ID NO: 57) | Elliott g. Cell 1997, 88: 223-233 |
| Amphipathic peptides | | |
| MAP | KLALKLALKALKAALKLA (SEQ ID NO: 58) | Morris MC., Nat Biotechnol. 2001, 19: 1173-1176 |
| Transportan | GWTLNSAGYLLGKINLKALAALAKKIL (SEQ ID NO: 59) | Pooga M, FASEB J 1998, 12: 67-77 |
| Transportan-10 | AGYLLGKINLKALAALAKKIL (SEQ ID NO: 60) | Soomets U, Biochim Biophys Acta 2000, 1467: 165-176 |
| KALA | WEAKLAKALAKALAKHLAKALAKALKACEA (SEQ ID NO: 61) | Oehike J., Biochim Biophys Acta 1998, 1414: 127-139 |
| Pep-1 | KETWWETWWTEWSQPKKKRKV (SEQ ID NO: 62) | Wyman Biochemistry 1997, 36: 3008-3017 |
| Pep-2 | KETWFETWFTEWSQPKKKRKV (SEQ ID NO: 63) | |
| MPG | GALFLGFLGAAGSTMGAWSQPKSKRKV (SEQ ID NO: 64) | Wagstaff K M Curr Med Chem 2006, 13: 1371-1387 |
| Vectocell peptides | VKRGLKLRHVRPRVTRMDV (SEQ ID NO: 65)<br>SRRARRSPRHLGSG* (SEQ ID NO: 66)<br>LRRERQSRLRRERQSR* (SEQ ID NO: 67)<br>GAYDLRRRERQSRLRRRERQSR (SEQ ID NO: 68)<br>*indicates addition of cys for conjugation to cargo | Coupade (2005) Biochem. J. 407 |
| Wr-T transporter | KETWWETWWTEWWTEWSQ-GPG-rrrrrrrr (SEQ ID NO: 69)<br>r = D-enantiomer arginine | Kondo (2004) Mol. Can. Thera 1623 |
| Other peptides | | |
| R7 | RRRRRRR (SEQ ID NO: 70) | Rothbard et al., Nat. Med 6 (2000) 1253-1257 |

Antennapedia-derived CPPs (Antp class) represent a class of particular interest, based around the 16 amino acid Penetratin sequence as shown in Table 2, which corresponds to the third loop of antennapedia protein and was shown to be responsible for translocation of the protein. Penetratin has been extensively developed as a delivery vehicle, including particularly for pharmaceutical use, and a wide range of Penetratin derivatives and modified sequences have been proposed and described. Reference may be made in particular to WO 91/1891, WO 00/1417, WO 00/29427, WO 2004/069279 and U.S. Pat. No. 6,080,724. Thus, the 16 amino acid sequence of Penetratin may be modified and/or truncated, or the peptide may be chemically-modified or retro-, inverso- or retro-inverso analogues may be made whilst retaining cell-penetrating activity.

Another group of cell penetrating peptides which may advantageously be used are based on the HIV-TAT sequence and HIV-TAT and fragments thereof represent a preferred class of CPPs for use according to the present invention. Various TAT-based CPPs are described in U.S. Pat. No. 5,656,122. An exemplary HIV-TAT peptide as used in the Examples below is RKKRRQRRR (SEQ ID. No. 71) but it will readily be appreciated that longer or shorter TAT fragments may be used.

As mentioned above no particular structural features or sequence motifs are common to all CPPs. However, various classes of CPPs may be identified by particular features, such as for example peptides which are amphipathic and net positively charged. Other groups of CPPs may have a structure exhibiting high α-helical content. Another group may be peptides characterised by a high content of basic amino acids. CPPs may thus be or may comprise oligomers of basic amino acids such as arginine e.g. 5 to 20, 6 to 15 or 6 to 12 R residues e.g. $R_7$ (SEQ ID NO: 70), $R_8$ (SEQ ID NO: 72) or $R_{11}$ (SEQ ID NO: 73) or $QSR_8$ (SEQ ID NO: 74).

Proline-rich amphipathic peptides are another class of CPP and such peptides characterised by the presence of pyrrolidine rings from prolines are described in Pujals et al. 2008 Advanced Drug Delivery Reviews 60, pages 473-484.

Other successfully developed CPPs include pVEC (Elmquist et al. 2003 Biol. Chem 384, pages 387-393; Holm et al. 2005 Febs Lett. 579, pages 5217-5222) and calcitonin-derived peptides (Krauss et al. 2004 Bioorg. Med. Chem. Lett., 14, pages 51-54).

Commercially available CPPs include Chariot, based on the Pep-1 peptide (Active Motif, France), the Syn-B vectors based on the protegrin peptide PG-1 (Syntem, France), and Express-si Delivery based on the MPG peptide from Genospectra, USA.

In addition to publically available and reported CPPs, novel or derivative CPP peptides may be designed and synthesized based on known or reported criteria (e.g. known CPP sequences or features such as basic amino acid content, α-helical content etc as discussed above). Additionally, randomly-designed or other peptides may be screened for CPP activity, for example by coupling or attaching such a peptide containing a reporter molecule e.g. a detectable label or tag such as a fluorescent tag to the desired cargo (an oligopeptidic compound according to the present invention) and testing to see if the construct is translocated across the cell membrane, for example by adding these peptides to live cells followed by examination of cellular import e.g. using confocal microscopy.

Indeed, whilst it is generally the case that a CPP will penetrate or enter virtually any cell type, it may in some cases be observed that successful or efficient delivery may be dependent, or may vary depending, on the precise nature of the cargo (e.g. cargo peptide sequence) and/or the CPP used. It would be well within the routine skill of the person skilled in the art to determine optimum peptide sequences and combinations etc, and to test and/or modify cargo and/or CPP sequence or structure etc.

As mentioned above, the signal sequence which may be comprised within the oligopeptidic compounds (or constructs) of the invention may be a signal peptide which directs the compound (or construct) into a particular sub-cellular compartment, and in particular into the nucleus. Nuclear localisation signals (NLSs) are again well known in the art and widely described in the literature and any known or functional NLS may be used.

Accordingly, a further preferred embodiment of the invention is a construct comprising (i) an oligopeptidic compound comprising an APIM motif (i.e. a PCNA-interacting motif) as defined herein, and (ii) a nuclear localisation signal.

An NLS may vary in length and/or sequence and a wide range of specific NLS sequences have been described. In general, however, it has been found that peptides comprising positively charged amino acids (notably lysine (K), arginine (R) and/or histidine (H)) may function as an NLS. An exemplary NLS may thus be a peptide of e.g. 4-20, more particularly 4-15, 4-12, 4-10 or 4-8 amino acids, wherein at least 4 amino acids (and more particularly at least 60, 70, 75, 80, 85, or 90% of the amino acid residues in the NLS peptide) are positively charged amino acids, preferably selected from K, R or H. Such an exemplary NLS may for example have or comprise the sequence RKRH (SEQ ID NO: 75).

Nuclear localisation signals, including both actual experimentally-determined and predicted or proposed NLS sequences, and strategies for identifying NLSs are described in Lange et al., J. Biol. Chem. 2007, 282(8), 5101-5105; Makkerh et al., Current Biology 1996, 6(8), 1025-1027; Leslie et al., Methods 2006, 39, 291-308; and Lusk et al. Nature Reviews MCB 2007, 8, 414-420.

A classical NLS consists of either one (monopartite) or two (bipartite) stretches of basic amino acids. A monopartite NLS may be exemplified by the SV40 large T antigen NLS ($^{126}$PKKKRKV$^{132}$ [SEQ ID NO: 76]) and a bipartite NLS by the nucleoplasmin NLS ($^{155}$KRPAATKKAGQAKKKK$^{170}$ [SEQ ID NO: 77]). The monopartite NLS consensus sequence K-[K/R]-X-[K/R] (SEQ ID NO: 78) has been proposed and accordingly an NLS according to the present invention may in one embodiment comprise or consist of such a consensus sequence (where X is any amino acid).

A representative bipartite NLS according to the invention may have the sequence KR-[X]$_{5-20}$-KKKK (SEQ ID NO: 79), e.g. KR-X$_{10}$-KKKK (SEQ ID NO: 80) (where X is any amino acid).

An alternative exemplary bipartite NLS may take the form RKRH-[X]$_{2-10}$-KK (SEQ ID NO: 81) e.g. RKRH-X$_2$-KK (SEQ ID NO: 82), for example RKRH-II-KK (SEQ ID NO: 83).

The oncoprotein c-myc NLS differs from classical NLSs in that only 3 of 9 amino acid residues are basic (PAAKRVKLD [SEQ ID NO: 84]), indicating that an NLS need not necessarily conform to the consensus or classical sequences given above. Makkerh et al (supra) describe NLS sequences in which a cluster of basic amino acids (e.g. KKKK [SEQ ID NO: 85]) is flanked by neutral and acidic residues, for example PAAKKKKLD (SEQ ID NO: 86).

Other possible NLS sequences which may be given by way of example include: PKKKRKVL (SEQ ID NO: 87), KKKRK (SEQ ID NO: 88), KKKRVK (SEQ ID NO: 89), KKKRKVL (SEQ ID NO: 90) and RKKRKVL (SEQ ID NO:

91). Any NLS which is a derivative of a known NLS e.g. the SV40, nucleoplasmin, UNG2 or c-myc NLS may be used.

A putative, proposed or predicted NLS sequence can be tested for NLS activity using principles and assays known and described in the art. For example a candidate NLS sequence may be attached to the desired cargo (in this case an oligopeptide according to the invention as defined herein) and the construct may be provided with a detectable reporter molecule (e.g a tag or label which may be visualised, for example a fluorescent label) and contacted with a test cell. Distribution of the construct in the cell may then be determined.

Thus, by way of summary, the skilled person will be aware of suitable signal sequences, but by way of example the following are mentioned herein. Examples of cell-penetrating peptide sequences include Penetratin™, a 16-amino acid peptide corresponding to the third helix of the homeodomain of Antennapedia protein, R rich tags such as R6-Penetratin (in which arginine-residues were added to the N-terminus of Penetratin) and derivatives of the HIV Tat protein such as GRKKRRQRRRPPQQ (SEQ ID NO: 92). Examples of nuclear localisation sequences include the SV40 protein derivative KKKRK (SEQ ID NO: 93).

A preferred construct according to the present invention comprises (i) an oligopeptidic compound comprising an APIM motif as defined herein, (ii) a nuclear localisation signal, and (iii) a cell penetrating signal sequence.

The separate elements or components of a construct according to the present invention may be contained or presented in any order, but preferably in the orders indicated above (e.g APIM oligopeptidic compound-CPP; APIM oligopeptidic compound-NLS; APIM oligopeptidic compound-NLS-CPP).

Furthermore, an oligopeptidic compound or construct of the invention may contain more than one PCNA-interacting motif. Thus, alternatively put, a construct according to the present invention may contain more than one oligopeptidic compound comprising a PCNA-interacting motif. A construct or oligopeptidic compound may for example contain 1-10, e.g. 1-6, or 1-4 or 1-3 or one or two motifs. Within a construct also containing a signal sequence, such motifs may be spaced or located according to choice e.g they may be grouped together, or they may be separated by signal sequence elements e.g. motif-NLS-motif-CPP; or motif-NLS-motif-motif-CPP; or motif-motif-NLS-CPP etc The components or elements of a construct according to the invention may be attached or linked to one another in any desired or convenient way according to techniques well known in the art. Thus, the components or separate parts may be linked or conjugated chemically e.g. using known chemical coupling technologies, or the constructs may be formed as a single whole using genetic engineering techniques e.g. techniques for forming fusion proteins, or they may simply be synthesized as a whole e.g. using peptide synthesis techniques.

The separate parts or components may be linked directly to each other or they may be linked indirectly by means of one or more linker (or spacer) sequences. Thus, a linker sequence may interspace or separate two or more individual parts of a construct or separate motif elements in an oligopeptidic construct. The precise nature of the linker sequence is not critical and it may be of variable length and/or sequence, for example it may have 0-40, more particularly 0-20, 0-15, 0-12, 0-10, 0-8, or 0-6, 0-4 or 0-3 residues e.g 1, 2 or 3 or more residues. By way of representative example the linker sequence, if present, may have 1-15, 1-12, 1-10, 1-8, 1-6 or 1-4 residues etc. The nature of the residues is not critical and they may for example be any amino acid, e.g a neutral amino acid, or an aliphatic amino acid, or alternatively they may be hydrophobic, or polar or charged or structure-forming e.g. proline. A range of different linker sequences have been shown to be of use, including short (e.g. 1-6) sequences of neutral and/or aliphatic amino acids.

Exemplary linker sequences thus include any single amino acid residue e.g. A, I, L, V, G, R, Q, T, or W, or a di-, tri- tetra- penta- or hexa-peptide composed of such residues.

As representative linkers may be mentioned I, II, IL, R, W, WW, WWW, RIL, RIW, GAQ, GAW, VAT, IILVI (SEQ ID NO: 94), IILVIII (SEQ ID NO: 95) etc.

The linkers between different elements may be the same or different.

In one embodiment, there is provided an oligopeptidic compound having or comprising the sequence MDRWLVKRILVATK (SEQ ID NO: 96) or MDRWLVKRILKKKRKVATKG (SEQ ID NO: 97).

Other representative compounds (or more particularly constructs) of the invention include MDRWLVKGAQP-KKKRKVLRQIKIWFQNRRMKWKK (SEQ ID NO: 98), MDRWLVKGAWKKKRVKIIRKKRRQRRRK (SEQ ID NO: 99), MDRWLVKGAWKKKRKIIRICKRRQRRRG (SEQ ID NO: 100), MDRWLVKGAWKKKRKI-IRKKRRQRRRK (SEQ ID NO: 101), MDRWLVKRI-WKKKRKIIRKKRRQRRRK (SEQ ID NO: 102), MDRWLVKWWWKKKRKIIRKKRRQRRRK (SEQ ID NO: 103), MDRWLVKWWRKRHIIKKRKICRRQRRRK (SEQ ID NO: 104), MDRWLVKRIWKKKRKIIR-RRRRRRRRRK (SEQ ID NO: 105), MDRWLVKRI-WKKKRKIIRQIKIWFQNRRMKWKK (SEQ ID NO: 106), MDRFLVKGAWRKRHIIKKRKKRRQRRRK (SEQ ID NO: 107), MDRWLVKWKKKRKIRRRRRRRRRRRK (SEQ ID NO: 108), MDRWLVKWKKKRKIRKKRRQR-RRK (SEQ ID NO: 109), MDRWLVK-WRKRHIRKKRRQRRRK (SEQ ID NO: 110), Ac-MDRWLVKGAWRKRHIRKKRRQRRRK (SEQ ID NO: 111), Ac-MDRWLVKWKKKRKIRRRRRRRRRRR (SEQ ID NO: 112), Ac-MDRALVKWKKKRKIR-RRRRRRRRR (SEQ ID NO: 113), Ac-MDRWLVKKKKRKRRRRRRRRRRRK (SEQ ID NO: 114), Ac-MDRWLVKKKKRKRRRRRRRRRRR (SEQ ID NO: 115), MDRWLVKRIWKKKRKIIRWLVKWW-WRKKRRQRRRK (SEQ ID NO: 116), KRRRQRRKKRI-IKRKKKWWWKVLWRDM (SEQ ID NO: 117).

Oligopeptidic compounds having sequences as set out in SEQ ID NOS. 98 to 117 are shown in Table 3 in Example 6 below, which shows the separate components making up the constructs (i.e. motif-containing sequence, linker, NLS, CPP, etc.) Thus, it will be seen that SEQ ID NOS. 98 to 117 represent constructs comprising at least one motif-containing sequence, an NLS and a CPP, in some cases linked by linker sequences which may vary in sequence, as specified. SEQ ID NO. 117 (RI-MDR26-3) is a retro-inverse peptide made up of D-amino acids. NLS sequences based on the SV40 or UNG2 NLS sequences are used, and CPP sequences based on Penetratin, HIV-TAT or an R-rich peptide.

In a further aspect, the invention provides a nucleic acid molecule encoding a peptide having or comprising (e.g. of) SEQ ID NO: 1 as defined above. Also provided is the complement of such a nucleic acid molecule. Preferably, the nucleic acid molecule comprises a promoter sequence operably linked to the sequence encoding a peptide having or comprising (e.g. of SEQ ID NO: 1. In a preferred embodiment, the nucleic acid molecule also encodes a signal sequence as defined above.

The nucleic acid molecule of the invention comprises at least 15 nucleotides and preferably no more than 800 nucleotides, more preferably no more than 700, 650, 600, 550, 500, 450, 400, 350, 300, 250, 200, 150, 100 or 50 nucleotides. The nucleic acid molecule is preferably an isolated molecule.

A further aspect relates to a vector comprising a nucleic acid molecule as defined herein. The vector may also contain further elements typically found in a vector such as an origin of replication, a selectable marker such as antibiotic resistance, and/or a multiple cloning site. The vector may further be an expression vector, and may comprise further elements, e.g. transcriptional and/or translational control or regulatory elements for expression of the nucleic acid molecules. Such control elements, e.g. promoters, ribosome binding sites, enhancers, terminators etc. are well known and widely described in the art.

The vector may for example be a plasmid or a virus, preferably it is selected from a retrovirus, an adenovirus and an adenovirus-associated virus.

In another aspect, there is provided a recombinant host cell containing a nucleic acid molecule and/or vector as described above. The host cell is an animal cell, preferably a mammalian cell, most preferably a rat, murine or human cell.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

In a further aspect, there is provided a pharmaceutical composition comprising an oligopeptidic compound as defined herein, a nucleic acid molecule as defined herein and/or a vector as defined herein, together with a pharmacologically (or pharmaceutically) acceptable excipient.

The excipient may include any excipients known in the art, for example any carrier or diluent or any other ingredient or agent such as buffer, antioxidant, chelator, binder, coating, disintegrant, filler, flavour, colour, glidant, lubricant, preservative, sorbent and/or sweetener etc.

The excipient may be selected from, for example, lactic acid, dextrose, sodium metabisulfate, benzyl alcohol, polyethylene glycol, propylene glycol, microcrystalline cellulose, lactose, starch, chitosan, pregelatinized starch, calcium carbonate, calcium sulfate, dextrates, dextrin, dextrose, dibasic calcium phosphate dihydrate, tribasic calcium phosphate, magnesium carbonate, magnesium oxide, maltodextrin, mannitol, powdered cellulose, sodium chloride, sorbitol and/or talc.

The pharmaceutical composition may be provided in any form known in the art, for example as a tablet, capsule, coated tablet, liquid, suspension, tab, sachet, implant, inhalant, powder, pellet, emulsion, lyophilisate, effervescent, spray, salve, emulsion, balm, plaster or any mixtures thereof. It may be provided e.g. as a gastric fluid-resistant preparation and/or in sustained action form. It may be a form suitable for oral, parenteral, topical, rectal, genital, subcutaneous, transurethral, transdermal, intranasal, intraperitoneal, intramuscular and/or intravenous administration and/or for administration by inhalation.

In a representative embodiment, the pharmaceutical composition is in a form suitable for liposomal administration, so preferably liposomes containing the pharmaceutical composition are provided. When liposomes are used, it may not be necessary to include a further excipient, so also provided are liposomes containing an oligopeptidic compound as defined herein, a nucleic acid molecule as defined herein and/or a vector as defined herein.

Using a database search, the inventors discovered the presence of the new PCNA binding motif in more than 200 other proteins, many of which are involved in DNA repair, maintenance and cell cycle regulation, e.g. transcription, replication, phosphorylation, ubiquitinylation, translesion synthesis, sister chromatid cohesion and cell cycle regulation (see Table 1 and Example 4). These proteins include the following a protein of unknown function which contains the conserved N-terminal domain I found in TFIIS elongation factor, an important protein for the progression of stalled transcription, so the inventors named it TFIIS-like protein. This protein contains the motif within its 7 N-terminal amino acids.

the multifunctional transcription factor TFII-I, which is critical for cell cycle control and proliferation. Cells overexpressing TFII-I have increased persistence of γ-H2AX foci (a marker for DNA double strand breaks), suggesting a role for TFII-I in DNA repair. This protein contains 4 of the motifs.

DNA topoisomerase II alpha (Topo II α), which functions in post-replicative DNA decatenation and DNA segregation. This protein contains one motif the key nucleotide excision repair protein XPA which recognizes helical kinks. This protein contains one motif.

RAD51B, a homologous recombination protein which shown to be important for proper centrosome function and chromosome segregation. This protein contains one motif.

Fanconi anemia core complex protein, FANCC. The FA core complex is shown to be involved in the DNA damage-activated signalling pathway regulating DNA repair of crosslinking agents. This protein contains one motif.

Further proteins which have been found to contain at least one motif are listed in Table 1.

Without wishing to be bound by theory, the inventors findings indicate that by preventing PCNA from interacting with at least one of its usual partners, cells may be sensitised to the effect of cytostatic agents. Thus, the effect of the cytostatic agent may be modulated. For example, interaction of a repair protein with PCNA may be inhibited (e.g. hABH2) thereby inhibiting DNA repair, and as a consequence increasing the effect of the cytostatic agent in damaging the DNA.

Thus, in a further aspect, there is provided a method of treating a disorder or condition, particularly a disorder or condition where it is desirable to inhibit the growth of cells, for example a hyperproliferative disorder, or any condition which requires or is responsive to cytostatic therapy, said method comprising administering (particularly administering an effective amount of) an oligopeptidic compound as defined herein, a nucleic acid molecule as defined herein and/or a vector as defined herein, to a subject in need thereof.

In another aspect, there is provided an oligopeptidic compound as defined herein, a nucleic acid molecule as defined herein and/or a vector as defined herein, for use in therapy, particularly for use in the treatment of a disorder or condition where it is desirable to inhibit the growth of cells, for example a hyperproliferative disorder, or in any treatment which involves cytostatic therapy (i.e. the use of a cytostatic agent). Thus the compound etc. may be used in the treatment of any condition which requires or is responsive to cytostatic therapy.

In another aspect, there is provided the use of an oligopeptidic compound as defined herein, a nucleic acid molecule as defined herein and/or a vector as defined herein, in the manufacture of a medicament for use in the treatment of a disorder or condition where it is desirable to inhibit the growth of cells, for example a hyperproliferative disorder, or in a treatment which involves cytostatic therapy.

As noted above, one surprising finding leading up to this invention is that the effect of a range of different cytostatic drugs may be enhanced or potentiated by the use of a peptide having a PCNA-interacting motif, thereby to inhibit the interaction of PCNA with a presumably broad range of proteins, for example proteins involved in DNA repair and replication and cell cycle progression etc. This leads to the general proposal that any PCNA-interacting molecule may be used in combination with a cytostatic agent, in order to enhance the effect of that cytostatic agent, or to sensitise cells to its effect.

Accordingly, in yet another aspect, there is provided a method of treating a disorder or condition where it is desirable to inhibit the growth of cells, for example a hyperproliferative disorder, or a method of treatment which involves cytostatic therapy, said method comprising administration of an oligopeptidic compound capable of interacting with PCNA or a nucleic acid molecule which comprises a nucleotide sequence that encodes an oligopeptidic compound capable of interacting with PCNA, and separate, simultaneous or sequential administration of a cytostatic agent to a subject in need thereof.

Alternatively viewed, there is provided an oligopeptidic compound capable of interacting with PCNA or a nucleic acid molecule comprising a nucleotide sequence which encodes said oligopeptidic compound for use in combination with a cytostatic agent in the treatment of a disorder or condition where it is desirable to inhibit the growth of cells, for example a hyperproliferative disorder, or in a treatment which involves cytostatic therapy.

Thus, there is provided the use of an oligopeptidic compound capable of interacting with PCNA or a nucleic acid molecule comprising a nucleotide sequence which encodes said oligopeptidic compound in the manufacture of a medicament for use in combination with a cytostatic agent in the treatment of a disorder or condition where it is desirable to inhibit the growth of cells, for example a hyperproliferative disorder, or in a treatment which involves cytostatic therapy.

Thus, in one embodiment the medicament may further comprise a cytostatic agent.

The medicament may be in the form of a single composition comprising both the oligopeptidic compound or nucleic acid molecule and the cytostatic agent, or it may be in the form of a kit or product containing them for separate (e.g. simultaneous or sequential) administration.

There is thus also provided the use of an oligopeptidic compound capable of interacting with PCNA or a nucleic acid molecule comprising a nucleotide sequence which encodes said oligopetitic compound in the manufacture of a medicament for the treatment of a disorder of cells, for example a hyperproliferative disorder, or in a treatment which involves cytostatic therapy, wherein the medicament is administered separately, simultaneously or sequentially with a cytostatic agent.

In another aspect, the invention provides a product containing an oligopeptidic compound capable of interacting with PCNA or a nucleic acid molecule comprising a nucleotide sequence which encodes said oligopeptidic compound together with a cytostatic agent as a combined preparation for separate, simultaneous or sequential use in the treatment of a disorder or condition where it is desirable to inhibit the growth of cells, for example a hyperproliferative disorder, or in a treatment which involves cytostatic therapy.

The oligopeptidic compound capable of interacting with PCNA, preferably the oligopeptidic compound comprising or having SEQ ID NO: 1, may be used to modulate or potentiate the effect of a cytostatic agent.

The oligopeptidic compounds (including constructs) according to the invention thus have a therapeutic utility in any condition or clinical situation where it is desirable (or where it may be of benefit) to inhibit the growth of cells.

The term "inhibit" is used broadly to include any reduction or decrease in cell growth as well as the prevention or abolition of cell growth. "Inhibition" thus includes the reduction or prevention of cell growth. This may be determined by any appropriate or convenient means, such as determining or assessing cell number; size (e.g size of tissue in which the cells are contained), cell viability and/or cell death etc., as may be determined by techniques well known in the art.

"Growth" of cells as referred to herein is also used broadly to include any aspect of cell growth, including in particular the proliferation of cells.

The oligopeptidic compounds may thus be used in the treatment of any condition (used broadly herein to include any disorder or any clinical situation) which is responsive to reduction of cell growth (particularly cell proliferation). The oligopeptidic compounds accordingly find utility in any therapy (or treatment) which targets cell growth (or proliferation). In other words, the compounds may be used in any therapeutic application in which it desirable or advantageous to inhibit cell proliferation.

The term "treatment" as used herein refers broadly to any effect or step (or intervention) beneficial in the management of a clinical condition and thus includes both therapeutic and prophylactic treatments. Treatment may include reducing, alleviating, ameliorating, slowing the development of, or eliminating the condition or one or more symptoms thereof, which is being treated, relative to the condition or symptom prior to the treatment, or in any way improving the clinical status of the subject. A treatment may include any clinical step or intervention which contributes to, or is a part of, a treatment programme or regimen. A prophylactic treatment may include delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom. Treatment according to the invention thus includes killing, inhibiting or slowing the growth of cells, or the increase in size of a body or population of cells (e.g in a tissue, tumour or growth), reducing cell number or preventing spread of cells (e.g to another anatomic site), reducing the size of a cell growth etc. The term "treatment" does not imply cure or complete abolition or elimination of cell growth, or a growth of cells.

Since the therapeutic applications and utilities of the present invention may generally involve inhibiting cell proliferation, any proliferating cell may be targeted in the therapies and utilities disclosed and encompassed herein. Such proliferating cells may include healthy or diseased cells and cells of any tissue in which proliferation occurs. For example, such cells may include in particular neoplastic cells, including both malignant and non-malignant neoplastic cells and cells of the immune system (immune cells), cells of the haematopoietic system generally, or skin cells.

Disorders or conditions involving abnormal or unwanted cell growth may be treated with cytostatic agents, and cytostatic agents may be used in any situation where it is desired to reduce or prevent cell growth and proliferation, including situations where it is desired to kill or ablate cells. Accordingly, as alternatively stated above, the oligopeptidic compounds (including constructs) of the present invention may be used in any method of treatment which involves (or includes)

the use of a cytostatic agent. This may include the treatment of any condition responsive to a cytostatic agent or any condition which may be treated with or which requires the use of a cytostatic agent.

The treatment of hyperproliferative disorders represents an aspect of particular interest. The term "hyperproliferative disorder" is used broadly herein to include any disorder or condition which involves increased, undesired or unwanted proliferation of cells. Thus included are not only conditions in which proliferation of cells is increased, for example relative to normal or healthy cells, or cells in the absence of the condition in question (e.g. compared or relative to a healthy or control subject, or compared or relative to cells taken from healthy or unaffected tissue in the same subject), but also conditions in which cell proliferation is not increased (or not greatly or significantly increased) over normal, but in which the proliferation which occurs is unwanted or undesired, whether generally or in a particular context. This may include for example an unwanted or undesired proliferation of cells which may occur in a "normal" response, e.g. an immune response or an inflammatory response etc. (in other words a "normal" response which may occur in a particular (e.g. normal) context, but which may nonetheless be unwanted). Such an unwanted proliferative response may for example be the proliferation of cells resulting in an unwanted inflammatory response, or an unwanted immune response such as an autoimmune response or an allergic reaction etc.

Hyperproliferative disorders which may be treated according to the present invention thus explicitly include inflammation (more particularly inflammatory disorders or conditions, or conditions involving, or associated with, or characterised by, inflammation) and autoimmune disorders or conditions, or disorders or conditions which have an autoimmune component.

A hyperproliferative disorder may involve (but is not limited to) the proliferation of cells which have the capacity for autonomous growth i.e. cells which exist and reproduce independently of normal regulatory mechanisms. A hyperproliferative disorder may therefore be a neoplastic disorder, and as noted above, this may be a malignant or non-malignant disorder.

Hyperproliferative cells may be classified as pathological (i.e. deviating from normal cells and associated with a disease state) or non-pathological (i.e. deviating from normal but associated with a disease state).

Pathological hyperproliferative cells may be associated with, or characteristic of the following disease states or disorders: restenosis, diabetic nephropathy, thyroid hyperplasia, Grave's Disease, psoriasis, benign prostatic hypertrophy, Li-Fraumenti syndrome, and cancers (including any tumours or malignancies).

Examples of non-pathological hyperproliferative cells include mammary ductal epithelial cells during development of lactation and also cells associated with wound repair.

The compounds of the invention may be useful in the treatment of such disorders and diseases and others, including diabetic retinopathy and peripheral vascular diseases.

Hyperproliferative disorders may as noted above be malignant or non-malignant neoplastic disorders. Also included are pre-malignant and non-neoplastic disorders. Examples of pre-malignant or non-neoplastic or non-malignant hyperproliferative disorders include myelodysplastic disorders, cervical carcinoma-in-situ, familial intestinal polyposes (e.g. Gardner syndrome), oral leukoplasias, histiocytoses, keloids, hemangiomas, hyperproliferative arterial stenosis, inflammatory arthritis, hyperkeratoses, and papulosquamous eruptions, including arthritis. Also included are viral-induced hyperproliferative diseases such as warts and EBV-induced disease (e.g. infectious mononucleosis), scar formation and the like.

The hyperproliferative disorder may thus be any hyperproliferative disorder, for example selected from neoplastic disorders such as cancer, psoriatic arthritis, rheumatoid arthritis, gastric hyperproliferative disorders such as inflammatory bowel disease, skin disorders including psoriasis, Reiter's syndrome, pityriasis rubra pilaris, and hyperproliferative variants of the disorders of keratinization.

Cancer represents a hyperproliferative disorder of particular interest, and all types of cancers, including e.g. solid tumours and haematological cancers are included. Representative types of cancer include cervical cancer, uterine cancer, ovarian cancer, pancreatic cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, pancreatic cancer, endometrial cancer, plasmacytoma, lymphomas, retinoblastoma, Wilm's tumor, Ewing sarcoma, melanoma and other skin cancers.

Mention may be made also of sinus tumours, urethral and genito-urinary cancers, oesophageal cancer, myeloma, endocrine cancers, osteosarcoma, angiosarcoma, and fibrosarcoma, and any tumour of the peripheral or central nervous systems, malignant or benign, including gliomas and neuroblastomas.

Autoimmune disorders or diseases represent a further condition of particular interest, and include for example rheumatoid arthritis, multiple sclerosis, immune disorders such as systemic lupus erythematosus (SLE; lupus) or myasthenia gravis.

Also of interest, generally speaking, are haematological disorders, or diseases of the blood or bone marrow, which need not necessarily be malignant or cancerous (e.g various dyscrasias, or dysplasias, non-malignant hyperplasis, agranuloma or MGUS (Monoclonal Gammopathy of Unknown Significance). Thus, any condition which involves an unwanted, or undesired or abnormal proliferation of blood or bone marrow cells, or their precursors, may be treated according to the present invention.

Other conditions which may be particularly mentioned include neoplastic meningitis and myeloproliferative diseases e.g. polycythemia vera (which occurs when excessive red blood cells are produced).

Various conditions may also occur as a result of, or may be otherwise associated with, inflammation or with an autoimmune disease. Such conditions may also be treated according to the present invention. Particular mention may be made of scleromyxedema and papular mucinosis, amyloidosis and Wegener's granulomatosis.

As noted above, the compounds of the invention may augment or potentiate the effects of a cytostatic agent. Accordingly, they may find utility in any therapeutic application where a cytostatic agent may be used. This may include any situation where it is desired to kill or ablate cells, which may include not only diseased cells. In particular, such a situation arises where is it desirable to ablate bone marrow prior to transplantation. The compounds of the invention may thus be used in myeloablation, and particularly myeloablation preceding a transplant, which may for example be a bone marrow transplant, or more generally a haemopoietic stem cell transplant (HSCT), (as well as from bone marrow, haemopoietic stem cells may also be obtained or derived from blood, e.g. peripheral blood).

Stem cell transplantation may be used in the treatment of diseases or conditions of the blood or bone marrow (i.e. haematological conditions or disorders), which may be malignant or non-malignant, and certain other types of cancer, including solid tumour cancers such as neuroblastoma, Demoplastic small round cell cancer, Ewing's sarcoma and choriocarcinoma. Haematological malignancies include leukaemias, lymphomas (Hodgkin's and non-Hodgkin's) and myelomas. Non-malignant haematological disorders include phagocyte disorders (e.g. myelodysplasia), anaemias (e.g. severe aplasia or aplastic anaemia), and myeloproliferative disorders (e.g. polycythemia vera and essential thrombocytosis). Other acquired conditions which may be treated by stem cell transplantation include metabolic disorders such as amyloidosis, and environmentally-induced diseases such as radiation poisoning. Stem cell transplantation may also be used in the treatment of congenital disorders, including various lysosomal storage disorders, immunodeficiencies and non-malignant haematological disorders e.g. anaemias, cytopenias, haemophagocytic syndromes, haemoglobinopathies, sickle cell disease and β thalassemia major.

Radiotherapy (also known as radiation therapy and radiation oncology) may be used in the treatment of various conditions including the hyperproliferative disorders described above. By "radiotherapy" is meant the use of ionizing radiation which is capable of damaging the DNA of cells by directly or indirectly ionizing the atoms which make up the DNA chain. Indirect ionization happens as a result of the ionization of water, forming free radicals, notably hydroxyl radicals, which then damage the DNA. In the most common forms of radiotherapy, most of the radiation effect is through free radicals.

Radiotherapy is useful in the treatment of cancer and for ablation of pathologic tissues because of the cytotoxic effects which result from persistent DNA double strand breaks or activation of programmed cell death. Ionizing radiation causes hyperproliferating cells, such as tumour and cancer cells, to undergo cell death by apoptosis, both in vivo and in vitro.

Unfortunately radiotherapy is often unsuccessful at completely eradicating cancer cells from a patient because it is often not possible to deliver a sufficiently high dose of local radiation to kill tumour cells without an unacceptably high risk of damage to the surrounding normal tissue. It is also known that cells show widely varying susceptibilities to radiation-induced cell death and ionizing radiation can also activate a pro-survival response mechanism through phosphatidylinositol 3-kinase/Akt (PI3K/Akt) and mitogen-activated protein kinase (MAPK) signal transduction pathways. Thus, there is a need to enhance the efficacy of radiotherapy by sensitizing cells to the effects of ionizing radiation.

Accordingly, the compounds of the invention may be used to provide such a sensitizing effect, in other words to enhance (or alternatively put to increase, augment, or potentiate) the effects of radiotherapy, or to render a subject (or more particularly cells, which may be present in a subject) more susceptible to the effects of radiotherapy. Thus, they may find utility in any therapeutic application where radiotherapy is used. This may include any situation where it is desired to kill or ablate cells, which may include not only diseased cells.

The compounds of the invention may thus be used as a sensitizer of cells to the DNA damaging effects of ionizing radiation. By "sensitizer" is meant the use of the compounds of the invention to enhance the DNA damaging effect of ionizing radiation on cells. This may be achieved by the inhibition of the endogenous cellular DNA repair mechanisms.

Thus, the present invention encompasses an oligopeptidic compound comprising a PCNA interacting motif (more specifically an oligopeptidic compound comprising a PCNA interacting motif as defined herein), or a nucleic acid molecule comprising a sequence encoding said PCNA interacting motif, for use in combination with radiotherapy, wherein the compound is administered separately, simultaneously or sequentially with the radiotherapy. The radiotherapy, together with the compound, may be administered in the treatment of any condition which is responsive to, or which requires, radiotherapy. The compounds or constructs of the invention may thus be used in the treatment of a disorder or condition where it is desirable to inhibit growth of cells, for example a hyperproliferative disorder, or in any treatment which involves radiotherapy, Alternatively defined, the invention provides an oligopeptidic compound comprising a PCNA-interacting motif (more specifically an oligopeptidic compound comprising a PCNA interacting motif as defined herein) or a nucleic acid molecule comprising a sequence encoding said PCNA interacting motif, as a sensitizer for radiotherapy, wherein the compound is administered separately, simultaneously or sequentially with radiotherapy.

These aspects of the invention also provide a method of sensitizing a subject (or more particularly cells or tissue in said subject) to radiotherapy, which method comprises administering to said subject an oligopeptidic compound of the invention as defined herein, particularly an amount of said compound which is effective to sensitize said subject (or said cells or tissue) to the radiotherapy.

This aspect of the invention can also be seen to provide a method of treating a subject, said method comprising administering radiotherapy to said subject, in conjunction with an oligopeptidic compound of the invention as defined herein. More particularly such a method may be a method of treatment of a disorder or condition which is responsive to, or which requires, radiotherapy, or a disorder or condition in which it is desirable to inhibit the growth of cells, or a method of treatment which involves radiotherapy.

The invention contemplates all types of radiotherapy including, but not limited to Conventional external beam radiotherapy, Stereotactic Radiotherapy, Virtual simulation, 3-dimensional conformal radiotherapy, intensity-modulated radiotherapy and Radioisotope Therapy (RIT).

Thus in one preferred embodiment of any of the aspects listed herein, the oligopeptidic compound, nucleic acid molecule and/or vector as defined herein is/are used in conjunction (simultaneously, separately or sequentially) with a radiotherapy.

In a further preferred embodiment of any of the aspects listed herein, the oligopeptidic compound, nucleic acid molecule and/or vector as defined herein is/are used in conjunction (simultaneously, separately or sequentially) with a cytostatic agent.

By "cytostatic agent" is meant an agent which is capable of inhibiting or suppressing the growth and/or multiplication (replication/proliferation) of animal cells.

Included as cytostatic agents are cytotoxic agents, antineoplastic agents and any agent which may be indicated for an oncological or haematological application. Thus, included are agents used in chemotherapeutic treatment protocols ("chemotherapeutic agents").

Cytostatic agents are typically grouped into different classes according to their mechanism of action and all of these classes are contemplated herein. Thus, the cytostatic agent may be an alkylating agent, a cross-linking agent, an intercalating agent, a nucleotide analogue, an inhibitor of spindle formation, and/or an inhibitor of topoisomerase I and/or II. Other types or classes of agent include anti-metabolites, plant alkaloids and terpenoids, or an anti-tumour antibiotic. Preferably, it is an alkylating agent.

Alkylating agents modify DNA by alkylating nucleosides, which leads to the prevention of correct DNA replication. Nucleotide analogues become incorporated into DNA during replication and inhibit DNA synthesis. Inhibitors of spindle formation disturb spindle formation, leading to the arrest of mitosis during metaphase. Intercalating agents intercalate between DNA bases, thereby inhibiting DNA synthesis. Inhibitors of topoisomerase I or II affect the torsion of DNA, thereby interfering with DNA replication.

Suitable cytostatic agents are known in the art, but by way of example actinomycin D, BCNU (carmustine), carboplatin, CCNU, Campothecin (CPT), cantharidin, Cisplatin, cyclophosphamide, cytarabine, dacarbazine, daunorubicin, docetaxel, Doxorubicin, DTIC, epirubicin, Etoposide, gefinitib, gemcitabine, ifosamide irinotecan, ionomycin, Melphalan, Methotrexate, Mitomycin C (MMC), mitozantronemercaptopurine, Oxaliplatin, Paclitaxel (taxol), PARP-1 inhibitor, taxotere, temozolomide (TZM), teniposide, topotecane, treosulfane vinorelbine, vincristine, vinblastine, 5-Azacytidine, 5,6-Dihydro-5-azacytidine and 5-fluorouracil are named herein. The skilled person will be aware of suitable dosage ranges for any given cytostatic agent and in one embodiment, the cytostatic agent is present in the pharmaceutical composition, or administered to the subject, in its typical dose range. In an advantageous embodiment, a lower dose of the cytostatic agent may be present/used, because the oligopeptidic compound, nucleic acid molecule or vector of the invention sensitises the cells to the cytostatic agents and so when used in combination with the oligopeptidic compound, nucleic acid molecule or vector of the invention, a lower dose of the cytostatic agent will have the same or a comparable therapeutic effect as a higher dose of the cytostatic agent on its own. The oligopeptidic compound, nucleic acid molecule or vector of the invention therefore makes it possible to treat subjects which have a low, or lower than average, tolerance for cytostatic agents, such as old people, babies or young children, or people weakened e.g. through disease, malnutrition and the like.

One problem encountered when using cytostatic agents to treat a hyperproliferative disorder is that typically not all of the affected cells are killed. It is envisaged that when an cytostatic agent and the oligopeptidic compound, nucleic acid molecule or vector of the invention are used together, a higher percentage of affected cells are killed and in one embodiment, a higher than typical dose of the cytostatic agent is used together with the oligopeptidic compound, nucleic acid molecule or vector of the invention to achieve killing of a very high proportion of the diseased cells, e.g. at least 50, 60 70 or 80%, preferably at least 85, 90 or 95%, most preferably to kill substantially all of the diseased cells.

As noted above, when the oligopeptidic compound, nucleic acid molecule and/or vector as defined herein is used in conjunction with a cytostatic agent, then the two different agents may be present in the same pharmaceutical composition, or they may be administered separately. Separate administration may include administration at substantially the same time but via different routes of administration or by administration at different locations. Separate administration may also include administration at different times, e.g. up to 1, 2, 3, 4, 5, 6 or 12 hours apart.

The subject is an animal (i.e. any human or non-human animal), preferably a mammal, most preferably a human.

The skilled person will be well aware of suitable methods for introducing the oligopeptidic compound, nucleic acid molecule and/or vector into cells. By way of example, a few suitable methods are briefly discussed below. As discussed in detail above, peptide-mediated methods of delivery can be used, notably cell penetrating peptides (CPPs), which as discussed above, are short, in some cases polycationic, sequences which can facilitate cellular uptake of peptides, proteins or nucleotide molecules which contain CPPs or to which CPPs are linked, for example by enhancing uptake into endosomes of mammalian cells. Microencapsulation provides a simple and cost-effective way to enclose bioactive materials within a semi-permeable polymeric membrane for the purpose of protecting the bioactive materials and releasing the enclosed substances or their products in a controlled fashion. In photochemical internalisation (PCI) both the molecule of interest and a photosensitising compound are taken up by the cell into a lysosome or an endosome. The cells are then exposed to light of suitable wavelengths to activate the photosensitising compound, causing the photosensitising compound to disrupt the membrane of the lysosome or endosome, thereby releasing the molecule of interest into the cytosol of the cell.

Other methods include microinjection, red blood cell ghost-mediated fusion, liposome fusion, osmotic lysis of pinosomes, scrape loading, electroporation, calcium phosphate and virus-mediated transfection and the use of copolymeric carriers.

Chitosan and water-soluble chitosan derivatives, in particular glycol chitosan, are emerging as the drug carriers of choice because of their biocompatibility and biodegradability in vivo. A preferred example is glycol chitosan hydrophobically modified with 5 β-cholanic acid.

The standard amino acid one letter code is used herein, so K stands for lysine (Lys), I stands for isoleucine (Ile) and so on.

The oligopeptidic compound of the invention may incorporate one or more, e.g. at least 1, 2, 3, 4 or 5 amino acids which possess a side chain that is not coded for by the standard genetic code, termed herein "non-coded amino acids". These may be selected from amino acids which are formed through metabolic processes such as ornithine or taurine, and/or artificially modified amino acids such as 9H-fluoren-9-ylmethoxycarbonyl (Fmoc), (tert)-(B)utyl(o)xy(c)arbonyl (Boc), 2,2,5,7,8-pentamethylchroman-6-sulphonyl (Pmc) protected amino acids, or amino acids having the benzyloxycarbonyl (Z) group. Preferably, where such non-coded amino acids are present, they are not located within the motif, but in one embodiment one or more non-coded amino acids are present within the motif.

In vitro and/or in vivo stability of the oligopeptidic compound of the invention may be improved or enhanced through the use of stabilising or protecting means known in the art, for example the addition of protecting or stabilising groups, incorporation of amino acid derivatives or analogues or chemical modification of amino acids, Such protecting or stabilising groups may for example be added at the N and/or C-terminus. An example of such a group is an acetyl group and other protecting groups or groups which might stabilise a peptide are known in the art.

The oligopeptidic compounds of the invention will typically comprise only amino acids having the L-configuration, but one or more amino acids having the D configuration may be present. Preferably, the oligopeptidic compound contains at least 1, 2, 3, 4 or 5 D-amino acids and they are preferably found in the motif, but in another embodiment, D amino acids are present only outside of the motif. The oligopeptidic compound may be linear or cyclic.

Thus, included particularly are inverso oligopeptidic compounds or inverso analogues of the oligopeptidic compounds of the invention (and more particularly inverso peptides).

Also included are retro oligopeptidic compounds (or retro peptides) in which the residues (e.g. amino acid residues) are assembled in opposite direction to the parental or reference compound (e.g. peptide).

Retro-inverso oligopeptidic compounds include D-amino acids in reverse (opposite) order to the parental or reference compound sequence. A retro-inverso analogue thus has reversed termini and reversed order of e.g. peptide bonds, while approximately maintaining the topology of the side chains as in the parental or reference sequence.

The compounds of the invention may include partial inverso, retro or retro-inverso sequences.

By "oligopeptidic compound" is meant a compound which is composed of amino acids or equivalent subunits, which are linked together by peptide or equivalent bonds. Thus, the term "oligopeptidic compound" includes peptides and peptidomimetics.

By "equivalent subunit" is meant a subunit which is structurally and functionally similar to an amino acid. The backbone moiety of the subunit may differ from a standard amino acid, e.g. it may incorporate one or more nitrogen atoms instead of one or more carbon atoms.

By "peptidomimetic" is meant a compound which is functionally equivalent or similar to a peptide and which can adopt a three-dimensional structure similar to its peptide counterparts, but which is not solely composed of amino acids linked by peptide bonds. A preferred class of peptidomimetics are peptoids, i.e. N-substituted glycines. Peptoids are closely related to their natural peptide counterparts, but they differ chemically in that their side chains are appended to nitrogen atoms along the molecule's backbone, rather than to the α-carbons as they are in amino acids.

In a preferred embodiment, at least the motif part of the oligopeptidic compound comprises only peptide bonds and preferably it is composed solely of coded amino acids. Most preferably, the oligopeptidic compound is a peptide.

The oligopeptidic compound may incorporate di-amino acids and/or β-amino acids, but at least the motif part is preferably only composed of α-amino acids. Most preferably, the oligopeptidic compound consists of α-amino acids.

The prefix "oligo" is used to designate a relatively small number of subunits such as amino acids, i.e. less than 200, preferably less than 100, 90, 80, 70 60 or 50 subunits. The oligopeptidic compound of the invention may thus comprise at least 5 and no more than 200 subunits. Preferably, it comprises at least 6, 7, 8, 9, 10, 11, 12, 13, 14, 15, 16, 17, 18, 19 or 20 subunits. Alternatively defined it comprises no more than 40, 35, 30, 29, 28, 27, 26 or 25 subunits. Representative subunit ranges thus include 5-40, 5-35, 5-30, 5-25, 5-20, 5-15, 5-12, 5-10 etc, 5-20 and 5-30 being preferred.

When the oligopeptidic compound comprises more than 5 subunits, then the nature of the subunits outside of the motif is not critical, so the subunits outside of the motif may for example be those found in the native protein such as hABH2, or they may be alanine residues or any other suitable residues.

Peptidomimetics typically have a longer half life within a patient's body, so they are preferred in embodiments where a longer lasting effect is desired. This can help reduce the frequency at which the composition has to be re-administered. However, for bio-safety reasons a shorter half life may be preferred in other embodiments; in those embodiments peptides are preferred.

The oligopeptidic compound of the invention may form part of a larger unit, e.g. it may be fused to a polypeptide to form a recombinant fusion protein or attached to a scaffold to form a peptide aptamer. Thus, fusions proteins or aptamers incorporating the oligopeptidic compound of the invention form further aspects of the present invention. Yet further aspects include pharmaceutical compositions comprising such fusions proteins or aptamers and the use of such fusions proteins or aptamers in therapy or in a method of treatment as described above.

Without wishing to be bound by theory, it is believed that for optimum DNA repair, maintenance and/or cell cycle regulation, several proteins have to interact with PCNA and that the oligopeptidic compounds of the invention are able to compete with proteins which posses the consensus motif for interacting with PCNA. Examples of proteins which may have to interact with PCNA via the novel motif for optimum DNA repair, maintenance and/or cell cycle regulation are listed in Table 1, so the protein may be a DNA polymerase, DNA ligase, Topoisomerase, DNA repair protein, DNA repair associated/interacting proteins, a protein involved in Sister chromatid cohesion, Chromatin remodelling, DNA binding, Ubiquitin processing or SUMO processing, E3 ubiquitin ligase, Transcription factor, Cell cycle regulator, Protein kinase, Metyltransferase, Acetyl-transferase, Cancer associated antigen, Structural protein or Centrosome kinesin.

When a sufficient level of the oligopeptidic compound of the invention is present within a cell, then the activity of one or more of these proteins is reduced or even abolished due to this competitive inhibition.

The oligopeptidic compound, nucleic acid molecule or vector as defined herein on its own is believed to have no enzymatic activity and to be non-toxic to cells (see Example 2). Thus, it has been shown that expression of a peptide of the invention comprising a PCNA-interacting motif as defined herein has no effect, or only minor effects, on the growth of the cell in which it is expressed. This may be dependent on the expression level. However, in some situations it is believed that the oligopeptidic compounds of the invention may be cytotoxic and accordingly they may be used as cytotoxic (or cytostatic) agents in their own right. Thus, the compounds of the invention may be used as cytotoxic agents in the treatment of conditions as discussed herein, and not necessarily always in combination with a separate cytostatic agent, or with radiotherapy.

Experiments have shown that oligopeptidic compounds administered to cells may have a cytotoxic effect on the cell.

The cytotoxic effect may vary depending on the precise nature of the compound, for example its sequence or composition. In particular, the cytotoxic effect may be obtained with constructs comprising an NLS and/or CPP and has been observed with constructs containing both and NLS and CPP. Strong evidence of cytotoxicity has been observed with nuclear-localising constructs.

Oligopeptidic compounds which exhibit a cytotoxic effect may be inverso, retro or retro-inverso etc.

More particularly, it has further been observed that an increased cytotoxic effect may be obtained with compound or constructs which contain more than one PCNA-binding motif according to the present invention.

In a further aspect, there is provided herein a kit, or a pharmaceutical product, comprising (i) an oligopeptidic compound as defined herein, a nucleic acid molecule as defined herein, and/or a vector as defined herein; and (ii) a cytostatic agent.

In another aspect there is provided a product containing (i) an oligopeptidic compound as defined herein, a nucleic acid molecule as defined herein, and/or a vector as defined herein and (ii) a cytostatic agent as a combined preparation for simultaneous, sequential or separate use in the treatment of a disorder or condition where it is desirable to inhibit the growth of cells, for example a hyperproliferative disorder, or in a treatment which involves cytostatic therapy.

Also contemplated is the in vitro administration of an oligopeptidic compound, nucleic acid molecule and/or a vector as defined herein to a cell or cell culture. Such in vitro methods may be used to study DNA repair, maintenance and/or cell cycle regulation. In a preferred aspect, the in vitro method is used to identify novel cytostatic agents. This may allow the faster identification of cytostatic agents, or the identification of agents which are only weakly cytostatic when used on their own, but which have useful cytostatic activity when used in combination with the oligopeptidic compound, nucleic acid molecule or vector of the invention.

The novel PCNA interacting motif as defined herein may be used in the diagnosis or monitoring of a disorder or condition where it is desirable to inhibit the growth of cells, for example a hyperproliferative disorder, or a treatment which involves cytostatic therapy or radiotherapy.

The inventors have found that several cancer associated antigens possess the PCNA-binding motif (see Table 1). It is therefore envisaged that a hyperproliferative or other disorder as discussed above may be diagnosed or its progress may be monitored by detecting the level of expression and/or location of a protein containing the motif, wherein an aberrant level and/or location of the protein is indicative of the disorder, e.g. a hyperproliferative disorder.

By an "aberrant level" is meant an increased level of the protein, e.g. the level is more than 10, 20, 30 or 40% compared to the level in a healthy cell of the same cell type, or a decreased level of the protein, e.g. the level is less that 10, 20, 30 or 40% compared to the level in a healthy cell of the same cell type.

In a preferred embodiment, an increased level of a protein containing the motif is indicative of a disorder, e.g. hyperproliferative disorder.

The level of the motif-containing protein can be analyzed using any known protein detection method. Preferably, an antibody specific for the motif is used. The antibody must be sufficiently specific for the motif (as compared to a reference protein such as Bovine serum albumin) for it to be used in a diagnostic method.

The antibody can be a monoclonal or a polyclonal antibody and it may be a whole antibody, e.g. IgG, IgA, IgE, IgM, or IgD, or an antibody fragment such as Fab, Fab', F(ab')$_2$, scFv, Fv, dsFv, ds-scFv, Fd, dAbs.

The detection assay may be carried out in vivo or in vitro, e.g. in a tissue or cell or body fluid sample, e.g. a cellular lysate, serum or blood.

Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, NMR contrast agents and radioactive materials. Examples of suitable enzymes include horseradish peroxidase, alkaline phosphatase, luciferase, beta-galactosidase, acetylcholinesterase, glucose oxidase, lysozyme, malate dehydrogenase and the like; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H. In the case of a direct visual label, use may be made of a colloidal metallic or non-metallic particle.

Preferably there is provided a method of diagnosing or monitoring the progress in a subject of a disorder or condition in which it is desirable to inhibit the growth of cells, for example a hyperproliferative disorder, said method said method comprising the steps of:
(1) contacting a test sample taken from said subject (e.g. mammal) with an antibody specific for the motif under conditions that permit the formulation of an antibody-antigen complex;
(2) measuring the amount of antibody-antigen complex in the test sample; and
(3) comparing the amount of antibody-antigen complex in the test sample to a control.

The control may be a healthy cell taken from the same subject, e.g. a healthy fibroblast cell.

In another aspect, the invention relates to antibodies specific for the motif.

The invention further includes a kit for diagnosing or monitoring a disorder or condition where it is desirable to inhibit the growth of cells, for example a hyperproliferative disorder, said kit comprising an antibody specific for the motif and instructions for the use thereof to diagnose the disorder or condition. Preferably, the antibody is coupled to a detectable substance as described above, or the kit includes such a detectable substance.

An alternative method of diagnosis involves the detection of an aberrant level of a nucleic acid molecule which encodes the motif. In this method, the level of the nucleic acid is monitored using a suitable detection method such as the polymerase chain reaction (PCR) or hybridisation techniques using suitably labeled probes. The invention will now be further described with reference to the following non-limiting Examples and Figures in which FIG. 1 contains confocal microscope images which show that hABH2 and PCNA co-localise and that the 10 N-terminal amino acids of hABH2 are necessary and sufficient or this co-localisation. Various hABH2 constructs (full length hAHB2 having residues 1-261, truncated hABH2 having residues 11-261 and an N-terminal fragment of HABH2 consisting of residues 1-10) labelled with EYFP were tested for co-localisation with ECFP-labelled PCNA (see Example 1). The left lane shows cells transfected with hABH2 alone, while the three remaining lanes show cells co-transfected with a hABH2 construct and PCNA.

FIG. 2 is a graph showing the results of FRET analysis. Normalised FRET ($N_{FRET}$) measurements are shown between EYFP (yellow fluorescent protein)/ECFP (cyan fluorescent protein) (Lane 1, background due to dimerisation of the tags), EYFP-PCNA/ECFP-PCNA (Lane 2, positive control because PCNA binds to PCNA), hAHB2-EYFP/ECFP-PCNA (Lane 3) and 1-10N hABH2-EYFP/ECFP-PCNA (Lane 4).

FIG. 3 contains graphs showing the effect of various cytostatic agents on cells expressing hABH2$_{1-10}$-EYFP, or expressing EYFP as a control. Treatments are shown on the left, untreated cells on the right. Treatments were carried out with 10 μM MMS, 40 μM BCNU, 1 μM MMC or 600 μM TMZ for 4 days (FIGS. 3a-d respectively). Data presented is from one representative out of at least 3 experiments, the cell growth at different doses was tested in 8 parallel wells.

FIG. 4 shows a sequence alignment of the 10 N-terminal amino acids of ABH2-homologs from *Homo sapiens* (NP 001001655.1), *Bos Taurus* (NP 001019687.1), *Rattus norvegicus* (XP 222273.3), *Mus musculus* (NP 778181.2), *Gallus gallus* (XP 415188.2) and *Strongylocentrotus purpuratus* (XP 797704.1) using Clustal W. The sequences were obtained from a public database.

FIG. 5 shows an alignment of the sequences of the proteins identified in Example 4 from various different species.

Figure 6:
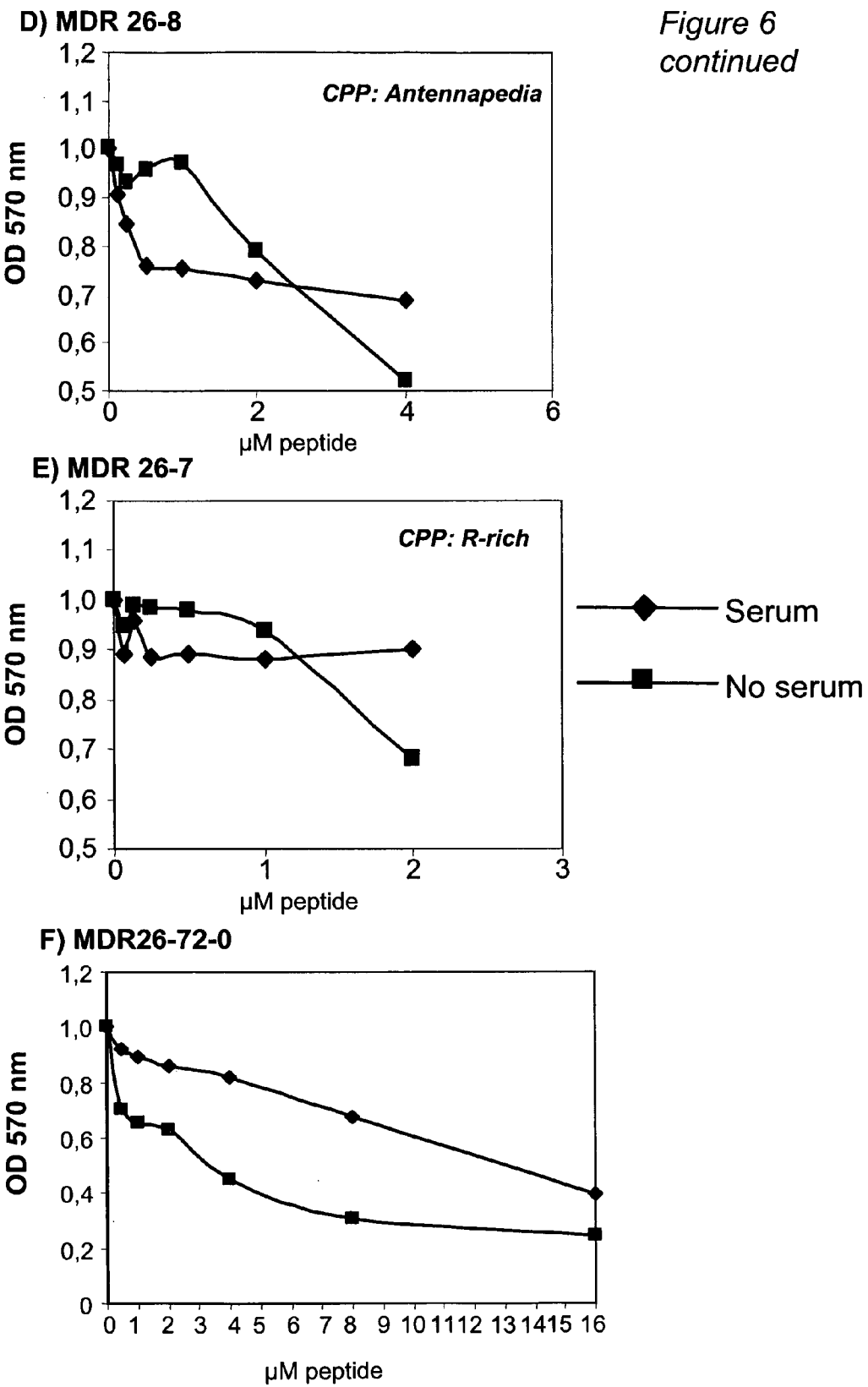
Figure 6:
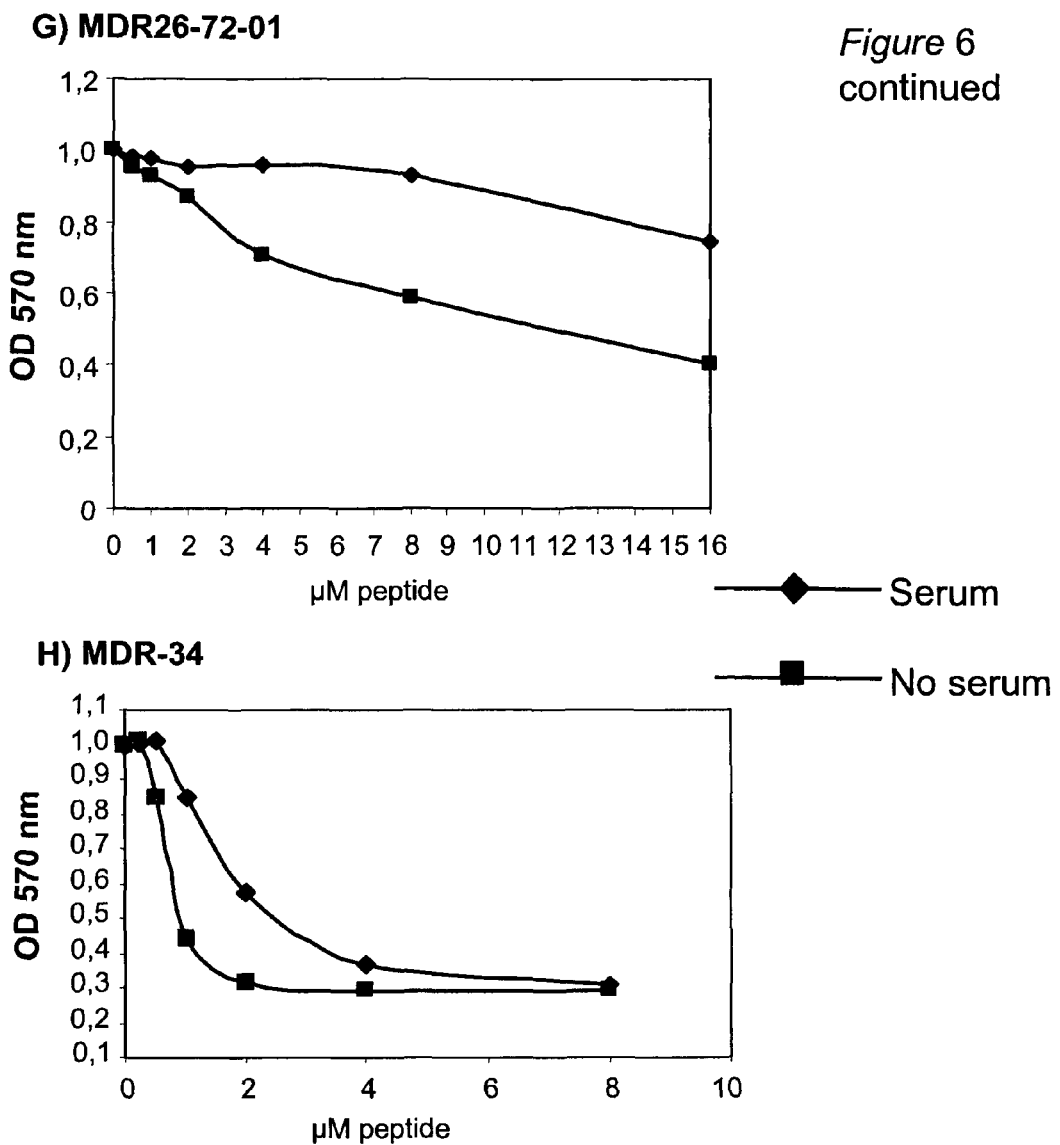

FIG. 6 presents graphs showing the results of cytotoxicity assays with various peptides as described in Example 7 (FIG. 6 (a) to (h)). HeLa cells were seeded into 96 well plates (6000 cells/well) and incubated for 3 hours. Various doses of peptides were added to the wells in presence (filled diamonds) or absence of serum (filled square) in the media. After 1 h equal volume media with 10% or 20% serum (to serum free media) were added to the wells. The cells were incubated for 48 hours before measurement of cell survival by the MTT assay. Graphs show cell growth (OD750 nm) against concentration of peptide (μM).

EXAMPLES

Experimental Procedures Used in the Examples
Expression Constructs.

Cloning of the fluorescently tagged expression constructs ECFP-PCNA and hABH2$_{1-261}$-EYFP has previously been described (Aas et al., 2003). Employing hABH2$_{1-261}$-EYFP as a template, hABH2$_{1-10}$-EYFP and hABH2$_{11-261}$-EYFP were generated by PCR. The amplicons were cloned into pEYFP-N1 (Clonetech) using NdeI/AgeI and AgeI/EcoRI respectively. The PCR product from EST (Image clone 5176979 (BC035374) RZPD) was cloned into pEYFP-C1 (HindIII/Acc651) to give EYFP-TFIIS-L. The EYFP-XPA construct was made by switching EYFP with EGFP (NheI/BsrGI fragment) in His9-HA-EGFP-XPA (Rademakers et al., 2003) generously provided by Dr. Wim Vermeulen (Department of Cell Biology and Genetics, Rotterdam). TFII-I-EYFP was generated by PCR amplification of TFII-I from pI3CX-TFII-I (Roy et al., 1993) generously provided by Dr. Robert G. Roeder (Laboratory of Biochemistry and Molecular Biology, The Rockefeller University, New York) and cloning into EYFP-N1 (SacI/ApaI). EYFP-Topo-IIα was made by switching the EGFP tag (EcoRI blunt/NheI) with the EYFP tag (XhoI blunt/NheI) from EGFP-Topo-IIα (pT104-1) (Mo and Beck, 1999) generously provided by William T. Beck (Division of Molecular Pharmacology, Department of Molecular Genetics, University of Illinois, Chicago). The hABH2$_{1-7}$-EYFP constructs including the F4 mutants, were made by annealing oligos with XhoI/EcoRI overhang followed by cloning into EYFP-N1 mutated in the ATG codon. All point mutations were made by site direct mutagenesis according to the QuickChange® II instruction manual. Restriction enzymes and Calf Intestinal Alkaline Phosphatase (CIP) were from New England Biolabs® Inc. and the oligonucleotides were from MedProbe, Eurogentech (Oslo, Norway). All constructs were verified by sequencing.

Confocal Imaging and FRET Measurements

Live HeLa cells were examined 16-24 hours after transient transfection (by Fugene 6 (Roche Inc.) according to the manufacturer's recommendations) of ECFP and EYFP fusion constructs. Fluorescent images were acquired using a Zeiss LSM 510 Meta laser scanning microscope equipped with a Plan-Apochromate 63×/1.4 oil immersion objective. Enhanced cyan fluorescent protein (ECFP) was excited at λ=458 nm and detected at λ=470-500 nm and enhanced yellow fluorescent protein (EYFP) was excited at λ=514 nm and detected at λ=530-600 nm, using consecutive scans. The thickness of the slice was 1 μm.

Fluorescent resonance energy transfer (FRET) occurs if the tags (EYFP and ECFP) are less than 100 Å (10 nm) apart. We detected FRET using the sensitised emission method, measuring acceptor (EYFP) emission upon donor (ECFP) excitation. We had FRET when the intensity of emitted light from EYFP after excitation of the ECFP fluorochrome was stronger than the light emitted by ECFP or EYFP-tagged proteins alone, after excitation with the EYFP and ECFP lasers respectively (bleed through), given by the equation: FRET=$I_2-I_1(I_{D2}/I_{D1})-I_3(I_{A2}/I_{A3})$ is >0. FRET was normalised for expression levels using the equation: $N_{FRET}$=FRET/$(I_1 \times I_3)^{1/2}$. $N_{FRET}$ was calculated from mean intensities (I) within a region of interest (ROI) containing more than 25 pixels where all pixels had intensities below 250 and the average intensities were between 100 and 200 for both the donor and the acceptor constructs. Channel 1 (ECFP) and 3 (EYFP) were measured as described above for imaging, and channel 2 (FRET) was excitated with λ=458 nm and detected at λ=530-600 nm. $I_{D1,D2,D3}$ and $I_{A1,A2,A3}$ were determined for cells transfected with ECFP and EYFP constructs only, with same settings and same fluorescence intensities as co-transfected cells ($I_1$ and $I_3$). ECFP-PCNA and EYFP-PCNA were included as positive controls, and due to dimerisation of co-expressed tags, ECFP and EYFP proteins expressed from empty vectors were included as negative controls in all experiments.

Culture of Cell Lines and Preparation of Cell Extracts

HeLa (cervical cancer) and HaCaT (spontaneously transformed keratinocyte) cells stably expressing the constructs of interest were prepared by transfection (by Fugene 6) followed by cell sorting or cloning by dilution, and prolonged culturing in selective (using genticine, G418, 400 μg/ml, Invitrogen) Dulbecco's modified Eagle's Medium high glucose 4.5 g/l (DMEM) (BioWhittaker®) supplemented with 10% Fetal Calf Serum (FCS), Amphotericin B (250 μg/ml, Sigma-Aldrich), gentamycin (100 μg/ml, Gibco) and glutamine (1 mM, BioWhittaker®). The cells were cultured at 37° C. in 5% carbon dioxide, humidified atmosphere. Fractionated cell extracts from HeLa were prepared by resuspending the cell pellets in 1× packed cell volume (PCV) in buffer I (10 mM Tris-HCl, pH 8.0 and 50 mM KCl) and 1× PCV in buffer II (10 mM Tris-HCl, 100 mM KCl, 20% glycerol, 0.5% Nonidet P-40, 10 mM EGTA, 10 mM MgCl$_2$, 1 mM DTT, 1× Complete protease inhibitor (Roche), phosphates inhibitor cocktail (PIC I and PIC II, Sigma). Cells were incubated under constant shaking for 30 min at 4° C. The supernatant (soluble fraction) was harvested. The pellet (containing nuclei) was resuspended in 1×PCV of buffer III (10 mM Tris-HCl, pH 8.0 and 100 mM KCl) and 1×PCV buffer II, and briefly sonicated until all nuclei were disrupted. 750 μg of the nucleoli-containing fraction was centrifuged and the pellet (chromatin bound fraction) was resuspended in buffer II and III. The chromatin bound fraction was incubated with DNAse/RNAse cocktail (2 μl Omnicleave® Endonuclease (200 U/μl, Epicentre® Biotecnologies, WI), 2 μl DNAse (10 U/μl, Roche Inc.), 2 μl Bensonase (250 U/μl, Novagene, Ge), 2 μl Micrococcal Nuclease (100-300 U/μl, Sigma-Aldrich) and 2 μl RNAse (10 mg/ml, Sigma-Aldrich) for 30 min at room temperature and 1 h at 37° C. 750 μg of the soluble fraction was incubated with additional 2 μl Omnicleave® over night at 4° C. during IP.

Co-Immuneprecipitation (co-IP) and Western Analysis (WB).

An in-house affinity purified rabbit polyclonal antibody raised against GFP protein, which also recognises EYFP and ECFP proteins, was covalently linked to protein-A paramagnetic beads (Dynal®) according to procedure from New England Biolabs® Inc (from now on called α-GFP beads). Each fraction was incubated with α-GFP beads (10 µl) during constant rotation at 4° C. over night (IP). After IP, the beads were washed 4 times with 200 µl 10 mM Tris-HCl, 50 mM KCl (pH 7.5), with 5 min incubation on ice in between. The beads were then resuspended in NuPAGE® (Invitrogen) loading buffer and 1 mM DTT, heated, and separated on 10% or 4-12% Bis-Tris-HCl (NuPAGE®) gels and transferred to PVDF membranes (Imrnobilon®, Millipore). The membranes were blocked for 1 h in 5% low fat dry milk in PBST (PBS with 0.1% Tween® 20). The primary antibodies, α-PCNA (PC10, Santa Cruz biotechnology Inc.) and α-GFP were diluted in 1% dry milk in PBST and incubated for 1 h, followed by 1 h incubation with secondary antibodies, Polyclonal Rabbit Anti-mouse IgG/HRP and Polyclonal Swine Anti-rabbit IgG/HRP, respectively (DakoCytomation, Denmark). The membranes were treated with chemiluminescence reagent (SuperSignal® West Femto Maximum, PIERCE), and the proteins visualised in Kodak Image Station 2000R.

Sequence Analysis

For initial sequence analysis the Swiss-Prot and TrEMBL databases were used to find proteins with similar sub-sequences as the sequence region of interest. The databases were queried with motifs in PROSITE format. Clustal W was used to align the sequences of interest. The conserved motifs listed in Supplementary File 1 were identified by comparison of gene orthologs. Data files for Inparanoid version 5.1 were downloaded from the Inparanoid web server <http://inparanoid.sbc.su.se/> for a representative subset of organisms. The human sequences were used as reference, and the Inparanoid processed fasta file was searched with a regular expression for the APIM motif, using a local tool. A slightly expanded motif definition was used, where Ala was allowed at either position 3 or 4 of the motif, in addition to Ile, Val and Leu, but not at both positions simultaneously. From a total of 22218 protein sequences there were 636 sequences with at least one hit against the APIM motif. These entries were matched against experimental and predicted subcellular localisation in the eSLDB database, downloaded from the web server <http://gpcr.biocomp.unibo.it/esldb/>, and 349 entries with no indication of targeting to the nucleus were removed. For the remaining 287 entries the corresponding Inparanoid, orthologs were identified, the corresponding sequences were extracted from the fasta files, and the resulting sequence libraries were aligned with Clustal W.

The 24 sequence entries without orthologs in Inparanoid were removed from the analysis. Two different procedures were used in parallel for identification of conserved sites. In the first procedure (Consensus) the consensus sequence was estimated from the multiple alignment for each hit position in the human sequence. When estimating the consensus equivalent symbols in the conservative APIM motif (without Ala) where treated as equivalent symbols for estimation of the consensus, so that e.g. Ile, Val and Leu were treated as a single residue type. The regular expression was tested again against the consensus before the hit position was accepted. In the alternative procedure (Individual) the regular expression was tested against each orthologous subsequence corresponding to a hit position in the human sequence, and only positions where at least 50% of the orthologs matched the expression were accepted. In this estimate subsequences consisting only of gaps were excluded, assuming that this could represent e.g. alternative splice variants. These two procedures gave almost identical results, and the combined output is shown in Supplementary File 1. In total 37 entries were removed by this procedure, the remaining 226 entries were listed and analysed. The protein descriptions used in the output were taken from the Inparanoid unprocessed human fasta file and Ensembl release 45. The output file is in html format and can be opened by a standard web browser.

Dot-Blot Analysis of Predicted PCNA-Binding Peptides

An Amino-PEG500-UC540 sheet (acid hardened with improved stability) containing dots of 28 nmol peptide (dyed with Ponceau to visualise the spots) was prepared at the peptide synthesis lab at The Biotechnology centre at University of Oslo, Norway. The membrane was probed with 1 µg/ml PCNA for 2 h, followed by probing with primary antibody (α-PCNA, PC10) and developed as described above for WB.

Cell Survival Assay

HeLa and HaCaT cells were seeded into 96 well plates (4000 cells/well) and incubated for 4 hours. Various doses of MMS (methyl methanesulfonate, Acros), BCNU (1,3-Bis(2-chloroethyl)-1-nitrosuream, Sigma), temozolomide (4-methyl-5-oxo-2,3,4,6,8-pentazabicyclo[4.3.0]nona-2,7,9-triene-9-carboxamide, TZM, Sigma) and mitomycin C (6-Amino-1,1a,2,8,8a,8b-hexahydro-8-(hydroxymethyl)-8a-methoxy-5-methyl-azirino[2',3':3,4]pyrrolo[1,2-a]indole-4,7-dione carbamate, MMC, Sigma) were added to the wells. The U2OS cells were exposed to MMS and TMZ only. The cells were exposed continuously until harvest. Cells were harvested every day for 4 days using the MTT assay (Mosmann, 1983). OD was measured at 570 nm, and the average from at least 6 wells was used to calculate cell survival. Data presented is growth from one representative experiment and has been reproduced at least 2 times.

Example 1

This work described in this Example investigates the localisation of hABH2 in replication foci and identifies direct interaction between hABH2 and PCNA, and the region of hABH2 responsible for such an interaction.

In living S-phase cells, PCNA tagged with green fluorescent protein (EGFP) forms distinct foci representing sites of replication and thus can be used as a S-phase marker.

Figure 1:
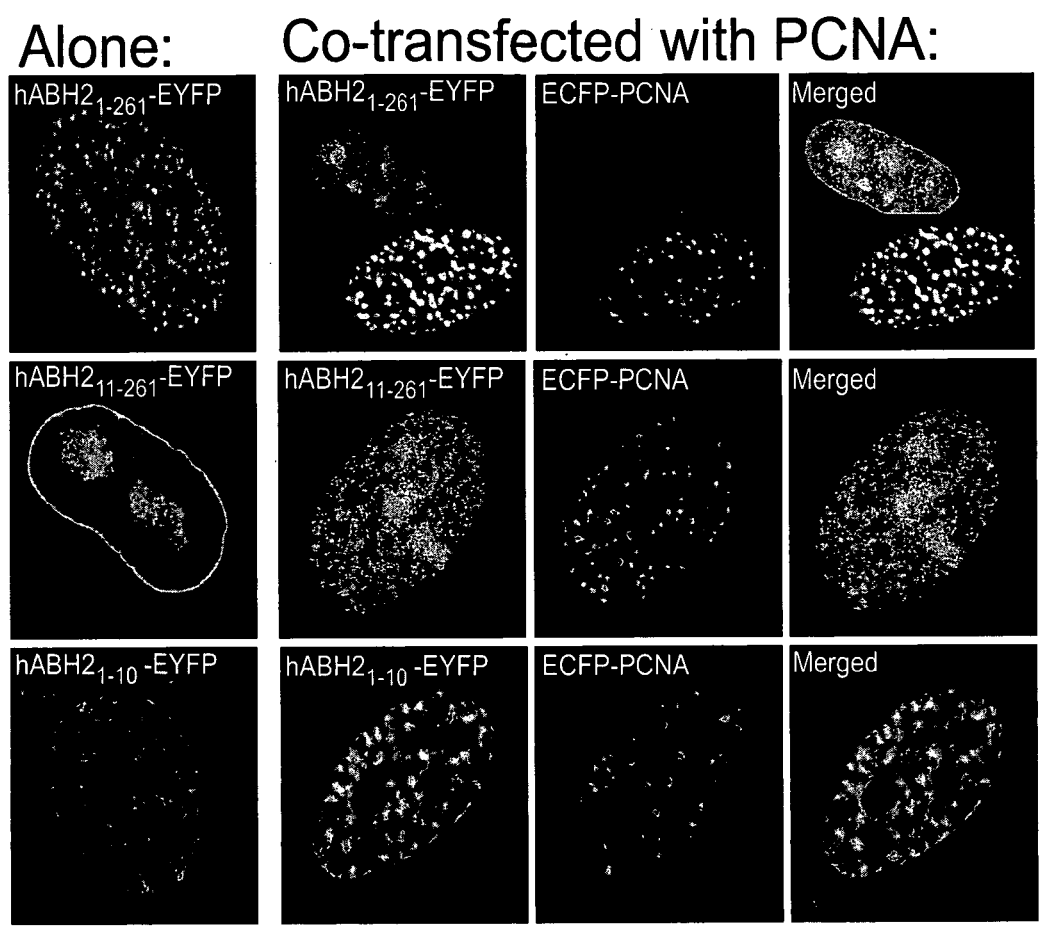

PCNA tagged with cyan fluorescent protein (ECFP) was co-expressed with various hABH2 deletion constructs fused with yellow fluorescent protein (EYFP). It was found that deletion of the 10 N-terminal amino acids in hABH2 (hABH2$_{11-261}$-EYFP) totally abolished the co-localisation with PCNA in replication foci. Remarkably, when these 10 amino acids were fused to EYFP (to give a construct called hABH2$_{1-10}$-EYFP), they were sufficient for co-localisation with PCNA. (FIG. 1). Notably, co-expression of ECFP-PCNA increased the localisation of full length hABH2 (hABH2$_{1-261}$-EYFP), as well as hABH2$_{1-10}$-EYFP, in nuclear foci, compared to cells expressing hABH2 constructs alone. This suggests a direct interaction between PCNA and hABH2 mediated by the 10 N-terminal amino acids of hABH2.

Figure 2:
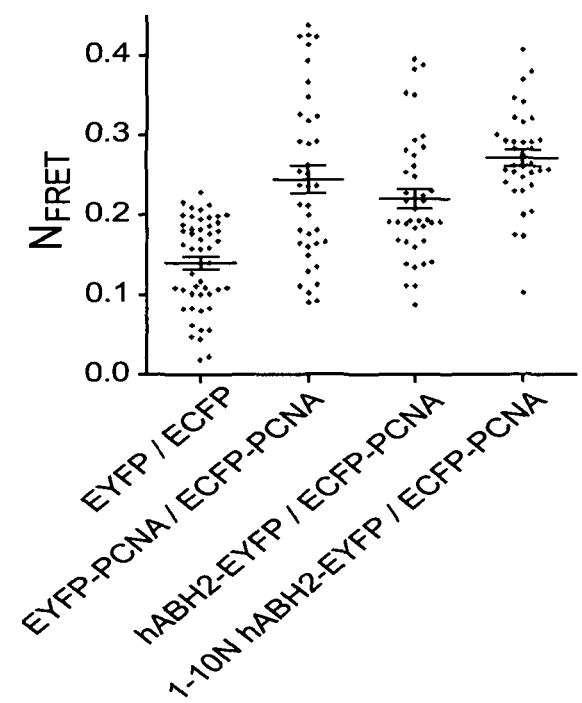

To examine the degree of proximity of hABH2 and PCNA, fluorescence resonance energy transfer (FRET) was measured. Both full length hABH2-EYFP and hABH2$_{1-10}$-EYFP generated positive FRET with ECFP-PCNA, demonstrating that the distance between the fluorescent tags is less than 100 Å. This suggests that the hABH2 variants directly interact with or are in the same complex as ECFP-PCNA (FIG. 2).

To confirm a direct interaction, co-immunoprecipitation studies were performed using protein extracts from cells stably expressing hABH2-EYFP, hABH2$_{11-261}$-EYFP, hABH2$_{1-10}$-EYFP or EYFP. Anti-GFP-antibodies were used to immunoprecipitate the respective fusion proteins. Subsequent western blot analyses revealed that the endogenous PCNA was pulled down by hABH2$_{1-216}$-EYFP and hABH2$_{1-10}$-EYFP, but not by hABH2$_{11-261}$-EYFP or EYFP. Taken together, these results suggest that hABH2 directly interacts with PCNA and that the binding sequence is contained within hABH2s 10 N-terminal amino acids.

Example 2

The ability of hABH2$_{1-10}$ to inhibit hABH2 was tested.
Cell lines expressing hABH2$_{1-10}$-EYFP or EYFP alone were exposed to the alkylating agents MMS (methyl methanesulfonate), BCNU (Carmustine), temozolomide (TZM) or mitomycin C (MMC). MMS is an $S_N2$ alkylating agent that leads to 3-methylcytosine (3meC) and 1-methyladenine (1meA) which are repaired by hABH2, while BCNU is an $O^6$-chloroethylating agent that mainly leads to interstrand crosslinks as well as some mono-base cyclic adducts (1,N(6) ethanoadenine). TZM is reported to be an $O^6G$ methylating agent, while MMC causes interstrand cross links via N-alkylation of guanine in CpG's.

Figure 3:
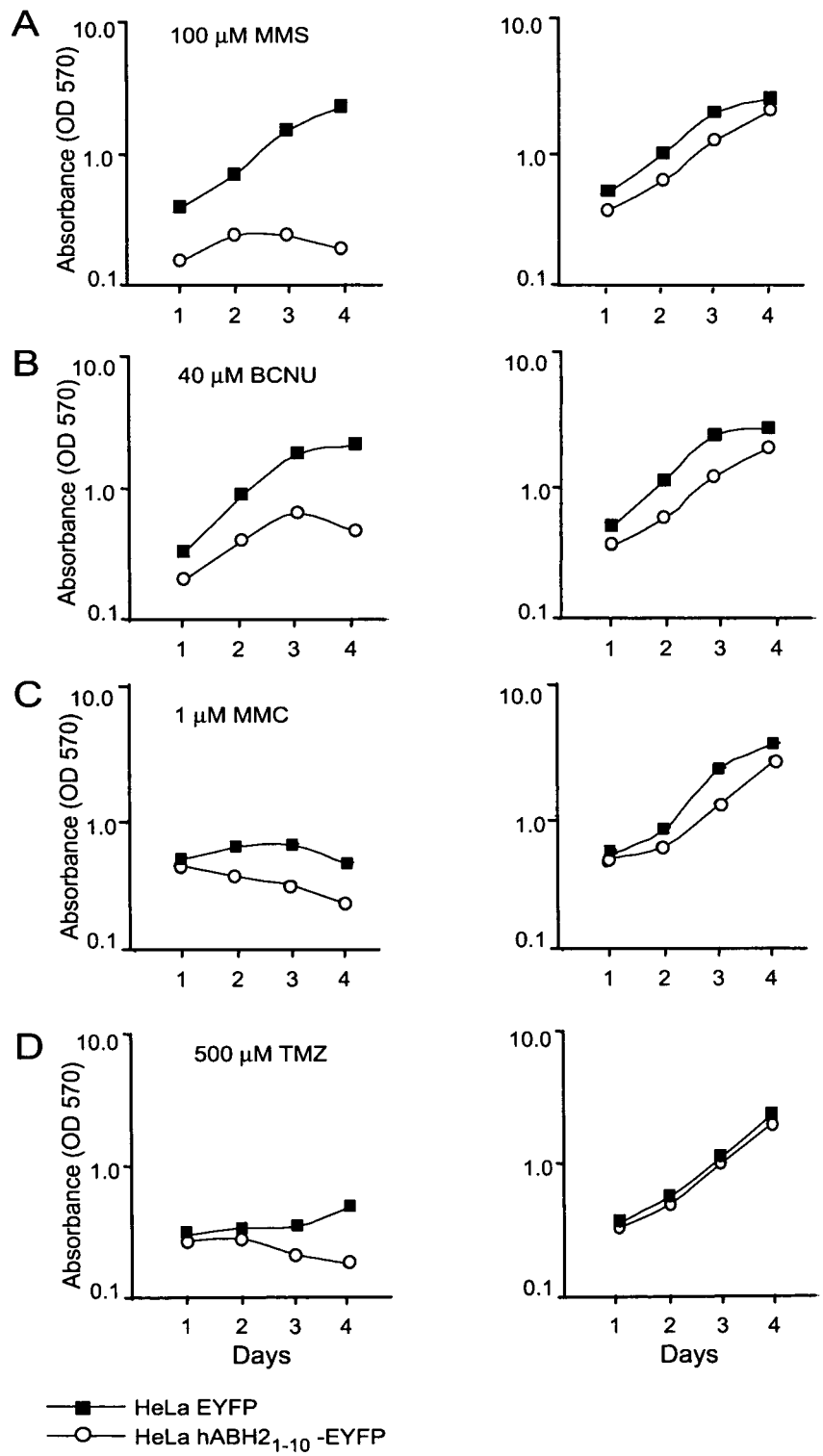

Over-expression of hABH2$_{1-10}$-EYFP or EYFP did not interfere with the growth rate of untreated cells; however it was found that expression of hABH2$_{1-10}$-EYFP sensitised HeLa cells to treatment with MMS. Surprisingly, it was also found that expression of hABH2$_{1-10}$-EYFP sensitised HeLa cells to all of the other cytostatic agents tested (FIG. 3). This indicates that the increased sensitivity was not only caused by inhibition of hABH2, which is believed mainly to repair 3meC and 1meA.

It is known from a previous study that mouse Abh2$^{-/-}$ cells, i.e. ABH2 knock-out cells, display increased sensitivity to MMS, but not to BCNU. Therefore, the increased sensitivity of cells expressing hABH2$_{1-10}$-EYFP to cytostatic agents such as BCNU cannot be explained solely by inhibition of hABH2.

HaCaT (spontaneously transformed keratinocyte) cells stably expressing hABH2$_{1-10}$-EYFP were also hypersensitive to MMS and TMZ.

Flow and comet assay analysis of the cells after treatment with the different alkylating agents showed that the drugs affected the cell cycle differently, and induced different levels and patterns of DNA repair intermediates (abasic sites, SSB, DSB) as detected by the comet assay. MMS lead to an S-phase arrest (day 1) and gave the highest levels of DNA repair intermediates after 4 hours. However, MMS treated cells showed normal cell cycle distribution and no increased levels of DNA repair intermediates on day 2. Similar to MMS, TMZ also lead to the highest levels of repair intermediates after 4 hours, however the cells were arrested in G2/M up to day 3 indicating a different damage and repair pattern. TMZ also induced more strand breaks than all the other three agents tested. This is surprising since TMZ is believed to induce mainly $O^6$methyl-G which is repair by a direct repair mechanism by MGMT, not involving removal of any bases or strand breaks. BCNU treatment lead to en transient G2/M arrest on day 1 and very low levels of repair intermediates, indicating that most cells containing crosslinks died. MMC treatment on the other hand, lead to an S-phase arrest on day 1 and 2, and this was more pronounced for the hABH2$_{1-10}$-EYFP expressing cells than for the control cells. The cells were still arrested in G2/M on day 3. No significant differences between the cells lines could be observed in the comet assay after MMC treatment, but the number of repair intermediates topped at day 2.

Generally, it was not possible to detect any significant differences in the amount of repair intermediates between the EYFP and hABH2$_{1-10}$-EYFP expressing cells by the comet assay. The comet and flow analysis show that the different agents used induces both different cell cycle responses and different patterns of repair. Still all agents had increased cytotoxicity in APIM expressing cells compared to EYFP expressing cells, thus supporting a role for several APIM containing proteins in the regulation between repair or cell death.

Example 3

An alignment of database sequences ABH2s from several different species revealed that the 7 N-terminal amino acids are highly conserved (FIG. 4). To identify a binding sequence, the importance of these amino acids for the peptide-PCNA interaction was examined using a dot blot assay. It was inter alia found that Arg3 and Lys7 could substitute each other and that Leu5 and Val6 could be substituted by each other or by other aliphatic amino acids such as Ile and Ala without affecting the apparent affinity towards PCNA. Furthermore, the completely conserved aromatic amino acid, Phe4 could be replaced by Tyr, whereas Ala in this position significantly reduced the PCNA binding.

Substitutions of amino acids 1-2 and 8-10 with Ala did not affect PCNA binding, suggesting the pentapeptide RFLVK (SEQ ID NO. 2) as the core interacting sequence.

Further assays revealed that this pentapeptide was by itself sufficient for PCNA binding, but additional flanking amino acids increased the interaction.

Next, amino acids 1-7 of hABH2, and variants of this sequence in which Phe4 was replaced by Tyr, Trp or Ala, were expressed in fusion with EYFP and tested for co-localisation with PCNA in vivo. Similar to what was found in the dot blot assay, fusion proteins containing an aromatic amino acid in position 4 co-localised with ECFP-PCNA, while proteins with Ala in this position did not.

Example 4

The Swiss-Prot and TrEMBL databases were used to find proteins with similar sub-sequences as the sequence which had been identified as being responsible for binding of hABH2 to PCNA. Using the consensus [KR]-[FYW]-[LIVA]-[LIVA]-[KR] (SEQ ID NO. 30) as the query, 226 hits were obtained (see Table 1 for a summary), of which several human proteins were chosen for further analysis.

One was a protein which like hABH2 contains the above consensus sequence within its 7 N-terminal amino acids. This protein also contains the conserved N-terminal domain I found in TFIIS elongation factor, an important protein for progression of stalled transcription. The inventors named this protein TFIIS-like protein (TFIIS-L). The function of this protein is unknown.

The second protein was the multifunctional transcription factor TFII-I, which contains 4 consensus sequences. TFII-I is critical for cell cycle control and proliferation, and cells over-expressing TFII-I have increased persistence of γ-H2AX foci (a marker for DNA double strand breaks), suggesting a role for TFII-I in DNA repair.

DNA topoisomerase II alpha (Topo II α) containing one consensus sequence was also examined. Topo II α functions in post-replicative DNA decatenation and DNA segregation.

A consensus sequence was also found internally in the key nucleotide excision repair protein (NER) XPA which recognizes helical kinks.

A consensus sequence was found in RAD51B, a homologous recombination protein which has been shown to be important for proper centrosom function and chromosome segregation.

Another protein was the Fanconi anemia core complex protein, FANCC, which was found to contain one consensus sequence. Fanconi anemia (FA) is a rare genetic disorder characterized by aplastic anemia, increased leukaemia susceptibility and hypersensitivity against crosslinking agents. The FA core complex has been shown to be involved in the DNA damage-activated signalling pathway regulating DNA repair of crosslinking agents.

In all these proteins the putative PCNA binding motif was found to be are conserved across different species (FIG. 5). Among these five proteins, only Topo II α and FANCC (after damage) has been reported to co-localise with BRCA1 in nuclear S-phase foci and Topo II α is the only protein containing a potential PIP-box (QttLaFkp, aa 1277-84). The inventors now showed that EYFP fusion proteins of each and every of these proteins co-localise with ECFP-PCNA in S-phase foci.

Other interesting APIM containing proteins found are members of the Poly(ADP-ribose) family (PARP-1, 2 and 4) involved in several DNA maintenance processes including DNA repair, the PARP-1 partner and Topo II α isoform DNA topoisomerase II beta involved in resolution of topological problems caused by replication forks. Furthermore, APIM is found in the REV3L subunit of the translesion polymerase ζ, involved in both point mutagenesis and larger scale genome stability, the DNA ligase I and IV involved in both DNA replication and repair, the four E3 ubiquitin-protein ligases (UHRF1 and UHRF2/NIRF, UBR1 and 2), all involved in regulation of the cell cycle, genome maintenance and integrity, as well as several other E3 ubiquitin ligases (Table 1). Interestingly, E3 ubiquitin ligase are frequently shown to be genetically and expressionally altered in breast tumorgenesis. Also containing APIM is the N-acetyltranferase ESCO1/EFO1, a protein which yeast orthologue bind PCNA through its truncated PIP-box and which is involved in proper sister chromatid cohesion, and the human structural maintenance of chromosome protein 5, hSMC5, which is shown to be involved in DNA repair of double strand breaks through HR and in maintenance of telomers in ALT cells. Finally, several subunits of the general transcription factors II and III, subunits of RNA polymerase II and serin/threonine protein kinases are found to contain the APIM motif (Table 1).

TABLE 1

| Type/group of proteins | Proteins containing APIM |
|---|---|
| DNA polymerase | Pol zeta catalytic subunit (hREV3L)[1] |
| DNA ligase | DNA ligase I[1], DNA ligase IV |
| Topoisomerase | Topo II alpha and Topo II beta[2] |
| DNA repair protein | hABH2*, XPA*, PARP-1[3], 2 and 4, RAD51B*, FANCC*[4] |
| DNA repair associated/ interacting proteins | XPA-binding protein 2, BRCA1/BRCA2-containing complex subunit 45 (prot-BRE), X-ray radiation resistance associated protein 1 |
| Sister chromatid cohesion | N-acetyltransferase ESCO1/EFO1[1], hSMC5[5] |
| Chromatin remodelling and DNA binding proteins | Chromodomain helicase-DNA-binding protein 3, 4 and 5, p325 subunit of RSF chromatin remodelling complex, Telomeric repeat-binding protein 2 (TRF2)[6] |
| E3 ubiquitin ligases | UHFR1, UHFR2, UBR1, UBR2, Ring finger proteins 3, 17 and 151, Probable E3 ubiquitin-protein ligase MYCBP2 |
| Ubiquitin processing | Ubiquitin-specific-processing protease (FAF-X) |
| SUMO processing | Sentrin/SUMO-specific protease SENP2 |
| Transcription factors | TFIIS-L*, TFII-I*, TFIIE-alpha, Sterol regulatory element binding transcription factor 2(SREBF2), TFIIIC subunit alpha, TFIID 100 kDa subunit (TAF5), TFIIIC 102 kDa subunit (TF3C gamma), Transcription factor-like protein MRG15 and X (Mortality factor 4-like protein 1 and 2), E2F transcription factor 7 |
| Cell cycle regulators | Cell division cycle associated 2, Bcl2-interacting mediator of cell death, Testis spermatocyte apoptosis-related gene 2 protein |
| Protein kinases | Serine/Threonine (S/T) -protein kinases SRPK1 and 2, 33 and MST4, Leucine-rich repeat S/T-protein kinase 1, STK23 (S/T protein kinase 23), S/T protein kinase PLK3, Microtubuli-associated S/T-protein kinase, Microtubuli-associated S/T-protein kinase 1, P13-kinase p110 subunit gamma, Interferon-inducible double stranded RNA-dependent protein kinase activator A, FYVE finger-containing phosphoinositide kinas, Phosphoinositide 3-Kinase-C2-beta, Phosphatidylinositol-4-phosphate 5-kinase type II alpha and beta, Phosphatidylinositol-4,5-bisphosphate 3-kinase catalytic subunit alpha isoform, MAPKAP kinase 2 and 5, Mitogen-activated protein kinase 15 (MAP 15) |
| Metyltransferase | H3 lysine-4 specific MLL3, H3-K9 methyltransferase 5, Putative rRNA methyltransferase 3 |

TABLE 1-continued

| Type/group of proteins | Proteins containing APIM |
|---|---|
| Acetyl-transferase | Diacetylglycerol O-acetyl transferase (DGAT1) |
| Cancer associated antigens | Melanoma associated antigen E1, MAGE E1, MAGE B18, MAGE-G1, NK-tumor recognition protein (NK-TR), Myc-binding protein associated protein, Myb binding protein 1A, Hepatoma-derived growth factor related protein 2 isoform 1, Serologically defined colon cancer antigen 1 |
| Structural proteins | Lamin-B1 and B2, Actin-like protein 2 |
| Centrosom, kinesins, | Centrosomal protein 110 kDA (Cep110), Centrosomal protein 192 kDa, Microtubule plus end directed kinesin motor 3 (KIF3A), Kinesin heavy chain (UKHC), kinetochore-associated protein 1 |

Bold: proteins localised in replication foci under normal conditions or after DNA damage. This study* or elsewhere:
[1] G. L. Moldovan, B. Pfander, and S. Jentsch, Cell 129 (4), 665 (2007).
[2] Z. Lou, K. Minter-Dykhouse, and J. Chen, Nat Struct Mol Biol 12 (7), 589 (2005); A. Niimi, N. Suka, M. Harata et al., Chromosoma 110 (2), 102 (2001).
[3] C. M. Simbulan-Rosenthal, D. S. Rosenthal, S. Iyer et al., Molecular and cellular biochemistry 193 (1-2), 137 (1999).
[4] C. Jacquemont and T. Taniguchi, BMC biochemistry 8 Suppl 1, S10 (2007).
[5] P. R. Potts, M. H. Porteus, and H. Yu, Embo J 25 (14), 3377 (2006).
[6] P. L. Opresko, M. Otterlei, J. Graakjaer et al., Mol Cell 14 (6), 763 (2004).

Example 5

The function of the consensus sequence in the proteins studied in Example 4 was experimentally examined. Because substitution of the aromatic amino acid Phe in the consensus sequence with Ala abolished PCNA interaction in vitro and co-localisation with PCNA in vivo, it was examined whether the corresponding mutation had similar effect on the full-length proteins. Mutation of Phe4 to Ala in full length hABH2 abolished co-localisation with PCNA. In TFII-I, containing 4 of the motifs, the Phe residues (F431A, F536A, F641A and F803A) were substituted individually and collectively to Ala. No single mutation reduced co-localisation with PCNA, but mutations in all of the consensus sequences in TFII-I strongly reduced the co-localisation with PCNA in replication foci, showing that several consensus sequence motifs present in the same protein may contribute to optimal PCNA interaction.

REFERENCES

Aas, P. A., Otterlei, M., Falnes, P. O., Vagbo, C. B., Skorpen, F., Akbari, M., Sundheim, O., Bjoras, M., Slupphaug, G., Seeberg, E., and Krokan, H. E. (2003). Human and bacterial oxidative demethylases repair alkylation damage in both RNA and DNA. Nature 421, 859-863.

Mo, Y. Y., and Beck, W. T. (1999). Association of human DNA topoisomerase IIalpha with mitotic chromosomes in mammalian cells is independent of its catalytic activity. Experimental cell research 252, 50-62.

Mosmann, T. (1983). Rapid colorimetric assay for cellular growth and survival: application to proliferation and cytotoxicity assays. Journal of immunological methods 65, 55-63.

Rademakers, S., Volker, M., Hoogstraten, D., Nigg, A. L., Mone, M. J., Van Zeeland, A. A., Hoeijmakers, J. H., Houtsmuller, A. B., and Vermeulen, W. (2003). Xeroderma pigmentosum group A protein loads as a separate factor onto DNA lesions. Mol Cell Biol 23, 5755-5767.

Roy, A. L., Malik, S., Meisterernst, M., and Roeder, R. G. (1993). An alternative pathway for transcription initiation involving TFII-I. Nature 365, 355-359.

Example 6

Preparation and Testing of Constructs Containing a Motif ("APIM")-Containing Peptide with Signal Sequences Peptides of SEQ ID NOS. 98 to 117 were synthesized using standard techniques, and fluorescent tags incorporated, where indicated, again using standard techniques. The peptides are shown in Table 3, which shows the amino acid sequence for each peptide, and also lists separately the individual components making up each peptide (motif ("APIM")-containing peptide, NLS, CPP, and linkers, as appropriate, and the tag used, where it is contained) Peptides of SEQ ID NOS. 98 to 116 are made up of L-amino acids. Peptide RI-MDR26-3 of SEQ ID NO. 117 is a retro-inverso peptide made up of D-amino acids. All of the peptides shown in Table 3 have at least one APIM peptide, an NLS and a CPP.

Various studies were undertaken to show the effect of the peptides on cells. Thus cells were incubated with the peptides to determine localisation of the peptides in the cells, using techniques based on those described in the Examples above. Briefly, the peptides indicated to be labelled with fluorescent tags were incubated with the cells (HeLa cells) and cellular import was examined using confocal microscopy.

The effects of the peptides in sensitising cells to the effects of cytostatic drugs were investigated using an MTT assay and a clonogenic assay (CFU assay) as described below.

Cytotoxicity of the peptides was investigated by an MTT assay as described below, using the peptides alone, in the absence of cytostatic drugs. Cytotoxicity data was also obtained from controls used in the cytostatic drug MTT assays (controls with peptide but without cytostatic drug), where the control peptides were followed for longer (4 days).

Membrane toxicity was investigated, again as described below.

Stability of the peptides was investigated by, MS analysis of the peptides after incubation of the peptides in serum-containing medium.

MTT Assay

HeLa cells were seeded into 96 well plates (6000 cells/well) and incubated for 3 hours. Various doses of MMS and Cisplatin were added to the wells. After 24 hours peptides were added to the cells in serum free media and incubated for 1 h. Fresh media with cytostatic drugs was added and the cells were harvested after additional 24, 48 and 72 hours. MTT was added to the cells (3-(4,5-Dimethylthiazol-2-yl)-2,5-diphenyltetrazolium bromide) and OD was measured at 570 nm [52], and the average from at least 6 wells was used to calculate cell survival. Data is presented as growth from one representative experiment and has been reproduced at least 2 times.

Clonogenic (CFU) Assay

750 HeLa cells were seeded out in 10 cm cell culture dishes in 11 ml growth media containing cytostatic drugs (MMS). The $2^{nd}$ day the cells were treated with peptides for one hour under serum free conditions. Fresh media containing fresh cytostatic drugs were added to the cells for further incubation for 10 days. The cells were then fixed in 6% glutaraldehyde in PBS for 15 min at room temperature, washed once in PBS and stained with crystal violet and colony forming units were counted. Only colonies consisting of at least 50 cells were included.

Cytotoxicity Assay

Cytotoxicity of the peptides after 48 hours are measured using the MTT assay. HeLa cells were seeded into 96 well plates (6000 cells/well) and incubated for 3 hours. Various doses of peptides were added to the wells in presence or absence of serum in the media. After 1 equal volume media with 1× or 2× (to serum free media) were added and the cells incubated for 48 hours before addition of MTT (see above)

Membrane Toxicity by Flow Cytometry

The cells were treated with different concentrations (2, 4 and 8 μM) of peptide for 1 hour. Next, propidium iodide (PI) (50 μg/ml in PBS) was added, this will stain DNA if the cell membranes are permeable. Analysis were done within the next 10 minutes on a FACS Canto flow cytometer (BD-Life Science).

The results are shown in Table 4. From this it can be seen that all tag-labelled peptides tested, which are essentially constructs of an APIM-containing peptide with a CPP and an NLS, localised to the nucleus. This effect was seen for peptides with different linker sequences linking the individual components of the construct, linkers of variable length, and peptides without linker sequences. This shows that the presence of linker sequences is not essential and the linker sequence can be varied.

The results of the MTT and CFU experiments with cytostatic agents show the effect of peptides in increasing the growth inhibitory effects of the cytostatic agents. Thus, the peptides are able to sensitise the cells to the effects of the cytostatic agents. This effect is analogous to that reported in Example 2 above for transfected cell-lines expressing an APIM-containing peptide.

Table 4 also shows a cytotoxic effect of a number of peptides. Further experimental work (data not shown) has indicated that a higher cytotoxic effect is observed with peptides which localise to the nucleus, compared with those that do not. A membrane toxicity experiment carried out with one peptide (MDR2; SEQ ID NO. 98) appears to indicate that membrane toxicity is low, which may suggest that the cytotoxic effect observed for the peptides is not due to a membrane effect. It has been observed that in some cases the cytotoxic effect may be seen only with increased peptide concentrations (for example, at 1 μM peptide cytotoxicity may not be seen (although an effect in sensitising cells to a cytostatic agent is seen), whereas at 2 μM peptide a cytotoxic effect of the peptide itself is seen, as well as the sensitising effect).

The results in Table 4 also show that the effects of the peptides in entering the cell and localising to the nucleus, in sensitising the cells to cytostatic agents, and in cytotoxicity may be obtained with different NLS and/or CPP sequences and, whilst the magnitude or extent of the effect may vary, the effects do not appear to be dependent on particular NLS and/or CPP sequences.

Certain peptides, as shown in Tables 3 and 4, incorporated an Ac group at the N-terminus. This was included with the aim of stabilising the peptides, both in serum and in the cytosol. Peptide MDR26-72-0 (SEQ ID NO. 112) showed good stability and good activity in the CFU and MTT assays, and the cytotoxicity tests. MDR26-72-0 contains an R-rich sequence as a CPP. It is believed that equally good results would be obtained with equivalent peptides in which the CPP is replaced by a CPP derived or based on Penetratin or HIV-TAT, in which the NLS may be SV40 or UNG2-derived).

TABLE 3

| SEQ ID NO: | Peptide # | Total Peptide Sequence | APIM sequence | Linker 1 | NLS | Linker 2 |
|---|---|---|---|---|---|---|
| 98 | MDR2 | MDRWLVKGAQPKKKRKVLRQIKIWFQNRRMKWKK-Ahx5-FAM)G | MDRWLVK (SEQ ID NO: 118) | GAQ | PKKKRKVL (SEQ ID NO: 123) | |
| 99 | MDR27 | MDRWLVKGAWKKKKRVKIIRKKRRORRRK-Ahx5-FAM)G | MDRWLVK (SEQ ID NO: 118) | GAW | KKKRVK (SEQ ID NO: 124) | II |
| 100 | MDR26-0 | MDRWLVKGAWKKKRKIIRKKRRQRRRG | MDRWLVK (SEQ ID NO: 118) | GAW | KKKRK' (SEQ ID NO: 125) | II |
| 101 | MDR26-1 | MDRWLVKGAWKKKRKIIRKKRRQRRRK-Ahx5-FAM)G | MDRWLVK (SEQ ID NO: 118) | GAW | KKKRK (SEQ ID NO: 125) | II |
| 102 | MDR26-2 | MDRWLVKRIWKKKRKIIRKKRRORRRK-Ahx5-FAM)G | MDRWLVK (SEQ ID NO: 118) | RIW | KKKRK (SEQ ID NO: 125) | II |
| 103 | MDR26-3 | MDRWLVKWWWKKKRKIIRKKRRQRRRK-Ahx5-FAM)G | MDRWLVK (SEQ ID NO: 118) | WWW | KKKRK (SEQ ID NO: 125) | II |

TABLE 3-continued

| | | | | | | |
|---|---|---|---|---|---|---|
| 104 | MDR26-4 | MDRWLVKWWRKRHIIKKRKKRRQRRRK-Ahx5-FAM)G | MDRWLVK (SEQ ID NO: 118) | WWW | RKRHIIKK (SEQ ID NO: 126) | |
| 105 | MDR26-7 | MDRWLVKRIWKKKKRKIIRRRRRRRRRRRK-Ahx5-FAM)G | MDRWLVK (SEQ ID NO: 118) | RIW | KKKRK (SEQ ID NO: 125) | II |
| 106 | MDR26-8 | MDRWLVKRIWKKKKRKIIRQIKIWFQNRRMKWKK-Ahx5-FAM)G | MDRFLVK (SEQ ID NO: 119) | RIW | KKKRK (SEQ ID NO: 125) | II |
| 107 | MDR26-10 | MDRFLVKGAWRKRHIIKKRKKRRQRRRK-Ahx5-FAM)G | MDRWLVK (SEQ ID NO: 118) | GAW | RKRHIIKK (SEQ ID NO: 126) | |
| 108 | MDR26-72 | MDRWLVKWKKKRKIRRRRRRRRRRRK-FAM)G | MDRWLVK (SEQ ID NO: 118) | W | KKKRK (SEQ ID NO: 125) | I |
| 109 | MDR26-32 | MDRWLVKWKKKRKIRKKRRQRRRK-FAM)G | Ac-MDRWLVK (SEQ ID NO: 120) | W | KKKRK (SEQ ID NO: 125) | I |
| 110 | MDR26-42 | MDRWLVKWRKRHIRKKRRQRRRK-FAM)G | Ac-MDRALVK (SEQ ID NO: 121) | W | RKRH (SEQ ID NO: 127) | I |
| 111 | MDR24-43 | MDRWLVKGAWRKRHIRKKRRQRRRK-FITC | Ac-MDRWLVK (SEQ ID NO: 120) | GAW | RKRH (SEQ ID NO: 127) | I |
| 112 | MDR26-72-0 | Ac-MDRWLVKWKKKRKIRRRRRRRRRRR | MDRWLVK (SEQ ID NO: 118) | W | KKKRK (SEQ ID NO: 125) | I |
| 113 | MDR26-72-A | Ac-MDRALVKWKKKRKIRRRRRRRRRRR | KVLWRDM (SEQ ID NO: 122) | W | KKKRK (SEQ ID NO: 125) | I |
| 114 | MDR26-72-011 | Ac-MDRWLVKKKKKRKRRRRRRRRRRK-Ahx5-FAM)G | MDRWLVK (SEQ ID NO: 118) | | KKKRK (SEQ ID NO: 125) | |
| 115 | MDR26-72-01 | Ac-MDRWLVKKKKKRKRRRRRRRRRRR | MDRWLVK (SEQ ID NO: 118) | | KKKRK (SEQ ID NO: 125) | |
| 116 | MDR34 | MDRWLVKRIWKKKKRKIIRWLVKWWWRKKRRQRRRK-Ahx5-FAM)G | MDRWLVK (SEQ ID NO: 118) | RIW | KKKRK (SEQ ID NO: 125) | II |
| 117 | RI-MDR26-3 | FITC-KRRRQRRKKRIIKRKKKWWWKVLWRDM | MDRWLVK (SEQ ID NO: 118) | WWW | KRKKK (SEQ ID NO: 128) | II |

| SEQ ID NO: | Peptide # | Total Peptide Sequence | 2nd APIM | Linker 3 | CPP | Tag |
|---|---|---|---|---|---|---|
| 98 | MDR2 | MDRWLVKGAQPKKKRKVLRQIKIWFQNRRMKWKK-Ahx5-FAM)G | | | RQIKIWFQNRRMKWK (SEQ ID NO: 129) | K-Ahx-5-FAM)G |
| 99 | MDR27 | MDRWLVKGAWKKKRVKIIRKKRRQRRRK-Ahx5-FAM)G | | | RKKRRQRRR (SEQ ID NO: 130) | K-Ahx-5-FAM)G |
| 100 | MDR26-0 | MDRWLVKGAWKKKRKIIRKKRRQRRRG | | | RKKRRQRRRG (SEQ ID NO: 131) | No tag |
| 101 | MDR26-1 | MDRWLVKGAWKKKRKIIRKKRRQRRRK-Ahx5-FAM)G | | | RKKRRQRRR (SEQ ID NO: 130) | K-Ahx-5-FAM)G |
| 102 | MDR26-2 | MDRWLVKRIWKKKKRKIIRKKRRQRRRK-Ahx5-FAM)G | | | RKKRRQRRR (SEQ ID NO: 130) | K-Ahx-5-FAM)G |
| 103 | MDR26-3 | MDRWLVKWWWKKKRKIIRKKRRQRRRK-Ahx5-FAM)G | | | RKKRRQRRR (SEQ ID NO: 130) | K-Ahx-5-FAM)G |

TABLE 3-continued

| | | | | | | |
|---|---|---|---|---|---|---|
| 104 | MDR26-4 | MDRWLVKWWRKRHIIKKRKKRRQRRRK-Ahx5-FAM)G | | | RKKRRQRRR (SEQ ID NO: 130) | K-Ahx-5-FAM)G |
| 105 | MDR26-7 | MDRWLVKRIWKKKRKIIRRRRRRRRRRK-Ahx5-FAM)G | | | RRRRRRRRRR (SEQ ID NO: 132) | K-Ahx-5-FAM)G |
| 106 | MDR26-8 | MDRWLVKRIWKKKRKIIRQIKIWFQNRRMKWKK-Ahx5-FAM)G | | | RQIKIWFQNRRMKWK (SEQ ID NO: 129) | K-Ahx-5-FAM)G |
| 107 | MDR26-10 | MDRFLVKGAWRKRHIIKKRKKRRQRRRK-Ahx5-FAM)G | | | RKKRRQRRR (SEQ ID NO: 130) | K-Ahx-5-FAM)G |
| 108 | MDR26-72 | MDRWLVKWKKKRKIRRRRRRRRRRK-FAM)G | | | RRRRRRRRRR (SEQ ID NO: 132) | K-FAMG |
| 109 | MDR26-32 | MDRWLVKWKKKRKIRKKRRQRRRK-FAM)G | | | RKKRRQRRR (SEQ ID NO: 130) | K-FAMG |
| 110 | MDR26-42 | MDRWLVKWRKRHIRKKRRQRRRK-FAM)G | | | RKKRRQRRR (SEQ ID NO: 130) | K-FAMG |
| 111 | MDR24-43 | MDRWLVKGAWRKRHIRKKRRQRRRK-FITC | | | RKKRRQRRR (SEQ ID NO: 130) | K-FITC |
| 112 | MDR26-72-0 | Ac-MDRWLVKWKKKRKIRRRRRRRRRR | | | RRRRRRRRRR (SEQ ID NO: 132) | No tag |
| 113 | MDR26-72-A | Ac-MDRALVKWKKKRKIRRRRRRRRRR | | | RRRRRRRRRR (SEQ ID NO: 132) | No tag |
| 114 | MDR26-72-011 | Ac-MDRWLVKKKKRKRRRRRRRRRRK-Ahx5-FAM)G | | | RRRRRRRRRR (SEQ ID NO: 132) | K-Ahx-5-FAM)G |
| 115 | MDR26-72-01 | Ac-MDRWLVKKKKRKRRRRRRRRRR | | | RRRRRRRRRR (SEQ ID NO: 132) | No tag |
| 116 | MDR34 | MDRWLVKRIWKKKRKIIRWLVKWWWRKKRRQRRRK-Ahx5-FAM)G | RWLVK (SEQ ID NO: 134) | WWW | RKKRRQRRR (SEQ ID NO: 130) | K-Ahx-5-FAM)G |
| 117 | RI-MDR26-3 | FITC-KRRRQRRKKRIIKRKKKWWWKVLWRDM | | | RRRQRRKKR (SEQ ID NO: 133) | K-FITC |

TABLE 4

| SEQ ID NO: | Peptide # | Total Peptide Sequence | Localization | CFU | MTT | Stability | Cytotoxicity | Membrane Toxicity |
|---|---|---|---|---|---|---|---|---|
| 98 | MDR2 | MDRWLVKGAQPKKKRKVLRQIKIWFQNRRMKWKK-Ahx5-FAM)G | nucleus | | + | +(+) | | Low |
| 99 | MDR27 | MDRWLVKGAWKKKRVKIIRKKRRQRRRK-Ahx5-FAM)G | nucleus | | + | + | | |
| 100 | MDR26-0 | MDRWLVKGAWKKKRKIIRKKRRQRRRG | unknown | +(+) | | | + | |
| 101 | MDR26-1 | MDRWLVKGAWKKKRKIIRKKRRQRRRK-Ahx5-FAM)G | nucleus | + | | + | | |
| 102 | MDR26-2 | MDRWLVKRIWKKKRKIIRKKRRQRRRK-Ahx5-FAM)G | nucleus | + | | + | | |
| 103 | MDR26-3 | MDRWLVKWWWKKKRKIIRKKRRQRRRK-Ahx5-FAM)G | nucleus | ++ | ++ | +(+) | +(+) | |
| 104 | MDR26-4 | MDRWLVKWWRKRHIIKKRKKRRQRRRK-Ahx5-FAM)G | nucleus | ++ | ++ | +(+) | +(+) | |
| 105 | MDR26-7 | MDRWLVKRIWKKKRKIIRRRRRRRRRRK-Ahx5-FAM)G | nucleus | ++ | ++ | + | +(+) | |
| 106 | MDR26-8 | MDRWLVKRIWKKKRKIIRQIKIWFQNRRMKWKK-Ahx5-FAM)G | nucleus | ++ | ++ | ++ | + | |

TABLE 4-continued

| SEQ ID NO: | Peptide # | Total Peptide Sequence | Localization | CFU | MTT | Stability | Cytotoxicity | Membrane Toxicity |
|---|---|---|---|---|---|---|---|---|
| 107 | MDR26-10 | MDRFLVKGAWRKRHIIKKRKKRRQRRRK-Ahx5-FAM)G | nucleus | +(+) | | | | |
| 108 | MDR26-72 | MDRWLVKWKKKRKIRRRRRRRRRRRK-FAM)G | nucleus | ++ | ++ | +(+) | | |
| 109 | MDR26-32 | MDRWLVKWKKKRKIRKKRRQRRRK-FAM)G | nucleus | ++ | ++ | +(+) | | |
| 110 | MDR26-42 | MDRWLVKWRKRHIRKKRRQRRRK-FAM)G | nucleus | ++ | ++ | +(+) | | |
| 111 | MDR24-43 | MDRWLVKGAWRKRHIRKKRRQRRRK-FITC | nucleus | ++ | | +(+) | | |
| 112 | MDR26-72-0 | Ac-MDRWLVKWKKKRKIRRRRRRRRRR | unknown | +++ | ++ | ++ | ++ | |
| 113 | MDR26-72-A | Ac-MDRALVKWKKKRKIRRRRRRRRRR | unknown | – | (+) | ++ | (+) | |
| 114 | MDR26-72-011 | Ac-MDRWLVKKKKRKRRRRRRRRRRK-Ahx5-FAM)G | nucleus | – | +(+) | +++ | (+) | |
| 115 | MDR26-72-01 | Ac-MDRWLVKKKKRKRRRRRRRRRR | unknown | – | (+) | +++ | (+) | |
| 116 | MDR34 | MDRWLVKRIWKKKRKIIRWLVKWWWRKKRRQRRRK-Ahx5-FAM)G | nucleus | – | – | ++ | ++ | |

Example 7

Further Cytoxicity Data

In this Example more detailed data from cytotoxicity tests is presented. The cytotoxicity assay was performed as described in Example 6 above. Results are presented in FIG. 6 which shows the results of the MTT cytotoxicity assay for peptides MDR26-0 (SEQ ID NO. 100), MDR26-3 (SEQ ID NO. 103), MDR26-4 (SEQ ID NO. 104), MDR26-8 (SEQ ID NO. 106), MDR26-7 (SEQ ID NO. 105), MDR26-72-0 (SEQ ID NO. 112), MDR26-72-01 (SEQ ID NO. 115) and MDR34 (SEQ ID NO. 116).

It will be seen that cytotoxicity of the peptides can be observed, with a greater effect being seen in the absence of serum. Cytotoxicity is seen with all the MDR26 variant peptides, which have one APIM motif. Increased cytotoxicity is seen with MDR34 variants which have two APIM motifs. Similar results showing cytotoxicity are obtained with peptides corresponding to MDR34 (SEQ ID NO. 116) which have no tag (MDR34-0), or which are the inverso (I-MDR-34) or retroinverso (RI-MDR-34) equivalents of MDR34. MDR34-2 which does not have an NLS sequence, and which instead had an extended linker sequence IILVIII (SEQ ID. NO. 95) as linker 2, shows reduced cytotoxicity.

Example 8

Further experiments have been done which support the interaction between PCNA and APIM-containing peptides. Co-immunoprecipitation (co-IP) experiments have showed that both endogenous PCNA and EYFP-PCNA from cells stably expressing EYFP-PCNA were able to pull down hABH2. More interaction seen between hABH2 and PCNA in chromatin-enriched fractions indicates post-translational modifications on PCNA or hABH2. In these experiments co-IP of hABH2 from cells stably expressing EYFP-PCNA was demonstrated using magnetic beads coupled with antibodies against α-EYFP. The membrane was probed with α-hABH2 and re-probed with α-PCNA antibody. Co-IP was also demonstrated of hABH2 from cells only expressing endogenous proteins using magnetic beads coupled with antibodies against α-PCNA. The membrane was probed with α-hABH2 and reprobed with α-PCNA antibody.

Further experiments showing in vivo cross-linking support direct binding between APIM and PCNA. Crosslinked and reversed crosslinked FLAG fusion proteins from cells stably expressing hABH21-7-EYFP 3×FLAG and hABH21-7-F4A-EYFP 3×FLAG were immunoprecipitated using α-FLAG Affinity Gel. The IP elution fractions were analyzed by Western Blots using α-PCNA or α-FLAG antibodies.

The invention claimed is:

1. An oligopeptidic compound capable of interacting with proliferating cell nuclear antigen (PCNA), wherein the compound comprises a PCNA interacting motif as set forth in SEQ ID NO: 18, a nuclear localization signal sequence as set forth in SEQ ID NO: 125 and a cell penetrating signal sequence as set forth in SEQ ID NO: 73.

2. A pharmaceutical composition comprising an oligopeptidic compound according to claim 1 together with at least one pharmacologically acceptable carrier or excipient.

3. The pharmaceutical composition of claim 2, wherein the pharmaceutical composition is provided in a form suitable for oral, parenteral, topical, rectal, genital, subcutaneous, transurethral, transdermal, intranasal, intraperitoneal, intramuscular and/or intravenous administration and/or for administration by inhalation.

4. A kit comprising
(i) an oligopeptidic compound according to claim 1; and
(ii) a cytostatic agent.

5. A kit according to claim 4, wherein said oligopeptidic compound and said cytostatic agent are provided as a combined preparation for simultaneous, sequential or separate use in the treatment of a disorder or condition where it is desirable to inhibit the growth of cells, or in a treatment which involves cytostatic therapy.

6. A liposome containing the oligopeptidic compound according to claim 1 capable of interacting with proliferating cell nuclear antigen (PCNA).

7. The oligopeptidic compound of claim 1, wherein said oligopeptidic compound is part of a fusion protein or aptamer.

8. The kit of claim 4, wherein said cytostatic agent is selected from the group consisting of actinomycin D, BCNU (carmustine), carboplatin, CCNU, Campothecin (CPT), cantharidin, Cisplatin, cyclophosphamide, cytarabine, dacarbazine, daunorubicin, docetaxel, Doxorubicin, DTIC, epirubicin, Etoposide, gefinitib, gemcitabine, ifosamide irinotecan, ionomycin, Melphalan, Methotrexate, Mitomycin C (MMC), mitozantronemercaptopurine, Oxaliplatin, Paclitaxel (taxol), PARP-I inhibitor, taxotere, temozolomide (TZM), teniposide, topotecane, treosulfane vinorelbine, vincristine, vinblastine, 5-Azacytidine, 5,6-Dihydro-5-azacytidine and 5-fluorouracil.

9. The kit of claim 4, wherein said cytostatic agent is an alkylating agent.

10. The oligopeptidic compound of claim 1, wherein the compound comprises the sequence as set forth in SEQ ID NO: 112.

* * * * *

UNITED STATES PATENT AND TRADEMARK OFFICE
CERTIFICATE OF CORRECTION

PATENT NO. : 8,871,724 B2
APPLICATION NO. : 12/918797
DATED : October 28, 2014
INVENTOR(S) : Marit Otterlei It is certified that error appears in the above-identified patent and that said Letters Patent is hereby corrected as shown below:

Title page

In column 1 (page 2, item 56) at line 32, Under Other Publications, change "XRCCI" to --XRCC1--.

In column 1 (page 2, item 56) at line 39, Under Other Publications, change "Chemotheraphy" to --Chemotherapy--.

In column 1 (page 2, item 56) at line 49, Under Other Publications, change "Onogene" to --Oncogene--.

In column 1 (page 2, item 56) at line 65, Under Other Publications, change "Nati" to --Natl--.

In column 2 (page 2, item 56) at line 67, Under Other Publications, change "Nati" to --Natl--.

Specification

In column 2 at line 8, Change "(GRP)" to --(GFP)--.

In column 2 at lines 59-60, Change "ethanoadenine)," to --ethenoadenine),--.

In column 2 at line 60, Change "0$^6$G" to --O$^6$G--.

In column 3 at line 52, Change "(iv)" to --(v)--.

In columns 5-6 (TABLE 2) at line 6 (approx.), Change "Penatratin" to --Penetratin--.

In columns 5-6 (TABLE 2) at line 22 (approx.), Change "rqikiwfqnrrmkwick" to --rqikiwfqnrrmkwkk--.

In column 9 at line 47, Change "(Syntem, France)," to --(System, France),--.

In column 11 at line 44, Change "etc" to --etc.--.

In column 11 at line 50, Change "technologies," to --technologies--.

In column 12 at line 22, Change "MDRWLVKGAWKKKRKIIRICKRRQRRRG" to --MDRWLVKGAWKKKRKIIRKKRRQRRRG--.

Signed and Sealed this
Twentieth Day of October, 2015

Michelle K. Lee
*Director of the United States Patent and Trademark Office*

Specification

In column 12 at line 27, Change "MDRWLVKWWRKRHIIKKRKICRRQRRRK" to --MDRWLVKWWRKRHIIKKRKKRRQRRRK--.

In column 13 at line 50, Change "lyophilisate," to --lyophylisate,--.

In column 14 at line 20, Change "motif" to --motif.--.

In column 15 at line 47, Change "oligopeptitic" to --oligopeptidic--.

In column 16 at line 8, Change "number;" to --number,--.

In column 17 at line 50, Change "Fraumenti" to --Fraumeni--.

In column 17 at line 64, Change "leukoplasias," to --leukoplakias,--.

In column 18 at lines 42-43, Change "agranuloma" to --granuloma--.

In column 19 at line 10, Change "Demoplastic" to --Desmoplastic--.

In column 20 at line 20, Change "radiotherapy," to --radiotherapy.--.

In column 21 at line 22, Change "Campothecin" to --Camptothecin--.

In column 21 at line 25, Change "ifosamide" to --ifosfamide--.

In column 21 at lines 26-27, Change "mitozantronemercaptopurine," to --mitoxantronemercaptopurine,--.

In column 21 at lines 28-29, Change "topotecane, treosulfane" to --topotecan, treosulfan--.

In column 24 at line 20, Change "posses" to --possess--.

In column 24 at line 30, Change "Metyltransferase," to --Methyltransferase,--.

In column 25 at line 40, Change "that" to --than--.

In column 27 at line 35, Change "(Clonetech)" to --(Clontech)--.

In column 28 at line 1, Change "Plan-Apochromate" to --Plan-Apochromat--.

In column 28 at line 39, Change "genticine," to --geneticin,--.

In column 28 at line 62, Change "Biotecnologies," to --Biotechnologies,--.

In column 28 at line 63, Change "Bensonase" to --Benzonase--.

In column 28 at line 63, Change "Novagene," to --Novagen,--.

In column 29 at line 1, Change "Immuneprecipitation" to --Immunoprecipitation--.

In column 29 at line 15, Change "(Imrnobilon®," to --(Immobilon®,--.

In column 30 at line 23, Change "nitrosuream," to --nitrosourea,--.

In column 31 at line 24, Change "ethanoadenine)." to --ethenoadenine).--.

In column 31 at line 24, Change "$0^6G$" to --$O^6G$--.

In column 31 at line 59, Change "$0^6$methyl-G" to --$O^6$methyl-G--.

In column 33 at line 6, Change "centrosom" to --centrosome--.

In column 34 at line 15 (approx.), Change "tumorgenesis." to --tumorigenesis.--.

In column 34 at line 16 (approx.), Change "N-acetyltranferase" to --N-acetyltransferase--.

CERTIFICATE OF CORRECTION (continued)
U.S. Pat. No. 8,871,724 B2

Specification

In column 34 at line 22 (approx.), Change "telomers" to --telomeres--.

In columns 33-34 (TABLE 1) at line 45 (approx.), Change "Metyltransferase" to --Methyltransferase--.

In columns 35-36 (TABLE 1) at line 10 (approx.), Change "Centrosom," to --Centrosome,--.

In column 36 at line 58, Change "by," to --by--.

In column 37 at line 22, Change "1" to --1 h--.

In column 37 at line 24, Change "above)" to --above).--.

In column 38 at line 36, Change "cytoxicity" to --cytotoxicity--.

In column 43 at line 30, Change "Cytoxicity" to --Cytotoxicity--.

Claims

In column 100 at line 67, In Claim 8, change "Campothecin" to --Camptothecin--.

In column 101 at line 3, In Claim 8, change "ifosamide" to --ifosfamide--.

In column 101 at line 5, In Claim 8, change "mitozantronemercaptopurine," to --mitoxantronemercaptopurine,--.

In column 101 at line 7, In Claim 8, change "topotecane, treosulfane" to --topotecan, treosulfan--.